Figure 1A:
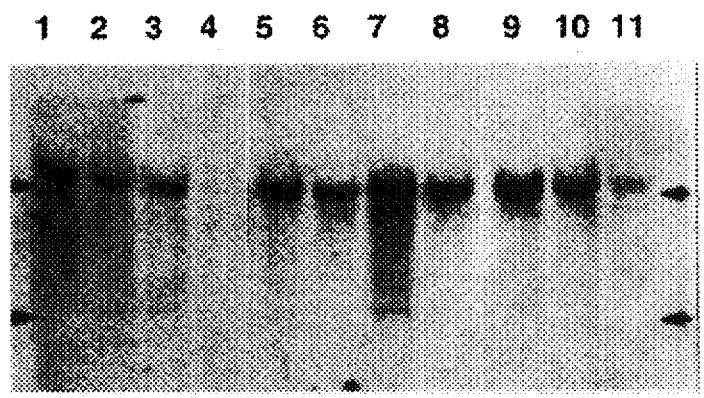

United States Patent [19]

Wilks et al.

[11] Patent Number: 5,821,069
[45] Date of Patent: Oct. 13, 1998

[54] METHOD FOR DETERMINING TYROSINE KINASE IN A SAMPLE

[75] Inventors: Andrew Frederick Wilks, Doneaster East, Australia; Andrew Ziemiecki, Berne, Switzerland; Ailsa Harpur, Mooroolbark, Australia

[73] Assignee: Ludwig Institute for Cancer Research, New York, N.Y.

[21] Appl. No.: 805,445

[22] Filed: Feb. 25, 1997

Related U.S. Application Data

[62] Division of Ser. No. 446,038, May 19, 1995, Pat. No. 5,658,791, which is a division of Ser. No. 64,067, Jun. 30, 1993.

[51] Int. Cl.⁶ .................. G01N 33/53; G01N 33/577; C07K 16/18
[52] U.S. Cl. .................. 435/7.21; 350/387.9; 350/388.1; 350/388.25; 350/388.26; 350/388.85; 350/389.1
[58] Field of Search .................. 435/7.21; 530/387.9, 530/388.1, 388.25, 388.26, 388.85, 389.1

[56] References Cited

U.S. PATENT DOCUMENTS 5,658,791  8/1997  Wilks .

OTHER PUBLICATIONS

Hunter, Cell 50:823, 1987.

*Primary Examiner*—Toni R. Scheiner
*Assistant Examiner*—Nancy A. Johnson
*Attorney, Agent, or Firm*—Felfe & Lynch

[57] ABSTRACT

The invention relates to a method of determining the presence of a tyrosine kinase in a sample using antibodies that specifically bind to kinase active proteins. The proteins have more than one tyrosine kinase domain and no SH2 domains. Exemplary proteins are the Janus Kinases, or "JAK1" and "JAK2." Both polyclonal and monoclonal antibodies are used in the detection method.

6 Claims, 34 Drawing Sheets

FIG. 2A

```
TGGCCGCCTA GCGAGCTGCC GGTCGACCCC AGCCAGCCCC AGCCAGCCCC GCGACGGGCG CTGCCTGGCC 60
CAGGGCACAC GGAAGTGCGC TTCTCTGAAG TAGCTTTGGA AAGTAGAGAA GAAAATCCAG120
```

```
TTTGCTTCTT GGAGAACACT GGACAGCTGA ATAA ATG CAG TAT CTA AAT
169                                     Met Gln Tyr Leu Asn
                                                    -10

ATA AAA GAG GAC TGC AAT GCC ATG GCT TTC TGT GCT AAA ATG AGG    214
Ile Lys Glu Asp Cys Asn Ala Met Ala Phe Cys Ala Lys Met Arg
         -5                  +1                  5

AGC TCC AAG AAG ACT GAG GTG AAC CTG GAG GCC CCT GAG CCA GGG    259
Ser Ser Lys Lys Thr Glu Val Asn Leu Glu Ala Pro Glu Pro Gly
              10                  15                  20

GTG GAA GTG ATC TTC TAT CTG TCG GAC AGG GAG CCC CTC CGG CTG    304
Val Glu Val Ile Phe Tyr Leu Ser Asp Arg Glu Pro Leu Arg Leu
              25                  30                  35

GGC AGT GGA GAG TAC ACA GCA GAG GAA CTG TGC ATC AGG GCT GCA    349
Gly Ser Gly Glu Tyr Thr Ala Glu Glu Leu Cys Ile Arg Ala Ala
              40                  45                  50
```

FIG. 2B

```
CAG GCA TGC CGT ATC TCT CCT CTT TGT CAC AAC CTC TTT GCC CTG      394
Gln Ala Cys Arg Ile Ser Pro Leu Cys His Asn Leu Phe Ala Leu
    55                  60                  65

TAT GAC GAG AAC ACC AAG CTC TGG TAT GCT CCA AAT CGC ACC ATC      439
Tyr Asp Glu Asn Thr Lys Leu Trp Tyr Ala Pro Asn Arg Thr Ile
    70                  75                  80

ACC GTT GAT GAC AAG ATG TCC CTC CGG CTC CAC TAC CGG ATG AGG      484
Thr Val Asp Asp Lys Met Ser Leu Arg Leu His Tyr Arg Met Arg
    85                  90                  95

TTC TAT TTC ACC AAT TGG CAT GGA ACC AAC GAC AAT GAG CAG TCA      529
Phe Tyr Phe Thr Asn Trp His Gly Thr Asn Asp Asn Glu Gln Ser
    100                 105                 110

GTG TGG CGT CAT TCT CCA AAG CAG AAA AAT GGC TAC GAG AAA          574
Val Trp Arg His Ser Pro Lys Gln Lys Asn Gly Tyr Glu Lys
    115                 120                 125

AAA AAG ATT CCA GAT GCA ACC CCT CTC CTT GAT GCC AGC TCA CTG      619
Lys Lys Ile Pro Asp Ala Thr Pro Leu Leu Asp Ala Ser Ser Leu
    130                 135                 140

GAG TAT CTG TTT GCT CAG GGA CAG TAT GAT TTG GTG AAA TGC CTG      664
Glu Tyr Leu Phe Ala Gln Gly Gln Tyr Asp Leu Val Lys Cys Leu
    145                 150                 155
```

FIG. 2C

```
GCT CCT ATT CGA GAC CCC AAG ACC GAG CAG GAT GGA CAT GAT ATT    709
Ala Pro Ile Arg Asp Pro Lys Thr Glu Gln Asp Gly His Asp Ile
    160                 165                 170

GAG AAC GAG TGT CTA GGG ATG GCT GTC CTG GCC ATC TCA CAC TAT    754
Glu Asn Glu Cys Leu Gly Met Ala Val Leu Ala Ile Ser His Tyr
    175                 180                 185

GCC ATG AAG AAG ATG CAG TTG CCA GAA CTG CCC AAG GAC ATC        799
Ala Met Lys Lys Met Gln Leu Pro Glu Leu Pro Lys Asp Ile
    190                 195                 200

AGC TAC AAG CGA TAT ATT CCA GAA ACA TTG AAT AAG TCC ATC AGA    844
Ser Tyr Lys Arg Tyr Ile Pro Glu Thr Leu Asn Lys Ser Ile Arg
    205                 210                 215

CAG AGG AAC CTT CTC ACC AGG ATG CGG ATA AAT GTT TTC AAG        889
Gln Arg Asn Leu Leu Thr Arg Met Arg Ile Asn Val Phe Lys
    220                 225                 230

GAT TTC CTA AAG GAA TTT AAC AAC AAG ACC ATT TGT GAC AGC AGC    934
Asp Phe Leu Lys Glu Phe Asn Asn Lys Thr Ile Cys Asp Ser Ser
    235                 240                 245
```

FIG. 2D

```
GTG TCC ACG CAT GAC CTG AAG GTG AAA TAC TTG GCT ACC TTG GAA      979
Val Ser Thr His Asp Leu Lys Val Lys Tyr Leu Ala Thr Leu Glu
250             255             260

ACT TTG ACA AAA CAT TAC GGT GCT GAA ATA TTT GAG ACT TCC ATG     1024
Thr Leu Thr Lys His Tyr Gly Ala Glu Ile Phe Glu Thr Ser Met
265             270             275

TTA CTG ATT TCA TCA GAA ATG AAT GAG ATG AAT TGG TTT CAT TCG AAT 1069
Leu Leu Ile Ser Ser Glu Met Asn Glu Met Asn Trp Phe His Ser Asn
280             285             290

GAC GGT GGA AAC GTT CTC TAC TAC GAA GTG ATG GTG ACT GGG AAT     1114
Asp Gly Gly Asn Val Leu Tyr Tyr Glu Val Met Val Thr Gly Asn
295             300             305

CTT GGA ATC CAG TGG AGG CAT AAA CCA AAT GTT TCT GTT GAA         1159
Leu Gly Ile Gln Trp Arg His Lys Pro Asn Val Ser Val Glu
310             315             320

AAG GAA AAA AAT AAA CTG AAG CGG AAA AAA CTG GAA AAT AAA GAC     1204
Lys Glu Lys Asn Lys Leu Lys Arg Lys Lys Leu Glu Asn Lys Asp
325             330             335

AAG AAG GAT GAG GAG AAA AAC AAG ATC CGG GAA GAG TGG AAC AAT     1249
Lys Lys Asp Glu Glu Lys Asn Lys Ile Arg Glu Glu Trp Asn Asn
340             345             350
```

FIG. 2E

```
TTT TCA TTC TTC CCT GAA ATC ACT CAC ATT GTA ATA AAG GAG TCT    1294
Phe Ser Phe Phe Pro Glu Ile Thr His Ile Val Ile Lys Glu Ser
        355                 360                 365

GTG GTC AGC ATT AAC AAG CAG GAC AAC AAG AAA ATG GAA CTG AAG    1339
Val Val Ser Ile Asn Lys Gln Asp Asn Lys Lys Met Glu Leu Lys
        370                 375                 380

CTC TCT TCC CAC GAG GAG GCC TTG TCC TTT GTG TCC CTG GTA GAT    1384
Leu Ser Ser His Glu Glu Ala Leu Ser Phe Val Ser Leu Val Asp
        385                 390                 395

GGC TAC TTC CGG CTC ACA GCA GAT GCC CAT TAC CTC TGC ACC        1429
Gly Tyr Phe Arg Leu Thr Ala Asp Ala His His Tyr Leu Cys Thr
        400                 405                 410

GAC GTG GCC CCC CCG TTG ATC GTC CAC AAC ATA CAG AAT GGC TGT    1474
Asp Val Ala Pro Pro Leu Ile Val His Asn Ile Gln Asn Gly Cys
        415                 420                 425

CAT GGT CCA ATC TGT ACA GAA TAC GCC ATC AAT AAA TTG CGG CAA    1519
His Gly Pro Ile Cys Thr Glu Tyr Ala Ile Asn Lys Leu Arg Gln
        430                 435                 440
```

FIG. 2F

```
GAA AGC GAG GAG GGG ATG TAC GTG CTG AGG TGG AGC TGC ACC    1564
Glu Gly Ser Glu Glu Gly Met Tyr Val Leu Arg Trp Ser Cys Thr
    445                 450                 455

GAC TTT GAC AAC ATC CTC ATG ACC GTC ACC TGC TTT GAG AAG TCT    1609
Asp Phe Asp Asn Ile Leu Met Thr Val Thr Cys Phe Glu Lys Ser
    460                 465                 470

GAG CAG GTG CAG GGT GCC CAG AAG CAG TTC AAG AAC TTT CAG ATC    1654
Glu Gln Val Gln Gly Ala Gln Lys Gln Phe Lys Asn Phe Gln Ile
    475                 480                 485

GAG GTG CAG AAG GGC CGC TAC AGT CTG CAC GGT TCG GAC CGC AGC    1699
Glu Val Gln Lys Gly Arg Tyr Ser Leu His Gly Ser Asp Arg Ser
    490                 495                 500

TTC CCC AGC TTG GGA GAC CTC ATG AGC CAC CTC AAG AAG CAG ATC    1744
Phe Pro Ser Leu Gly Asp Leu Met Ser His Leu Lys Lys Gln Ile
    505                 510                 515

CTG CGC ACG GAT AAC ATC AGC TTC ATG CTA AAA CGC TGC TGC CAG    1789
Leu Arg Thr Asp Asn Ile Ser Phe Met Leu Lys Arg Cys Cys Gln
    520                 525                 530
```

FIG. 2G

```
CCC AAG CCC CGA GAA ATC TCC AAC CTG CTG GTG GCT ACT AAG AAA    1834
Pro Lys Pro Arg Glu Ile Ser Asn Leu Leu Val Ala Thr Lys Lys
    535                 540                 545

GCC CAG GAG TGG CAG CCC TAC GTC TAC CCC ATG AGC CAG CTG AGT TTC    1879
Ala Gln Glu Trp Gln Pro Val Tyr Pro Met Ser Gln Leu Ser Phe
    550                 555                 560

GAT CGG ATC CTC AAG AAG AAG GAT CTG GTG CAG GGC GAG CAC CTT GGG    1924
Asp Arg Ile Leu Lys Lys Lys Asp Leu Val Gln Gly Glu His Leu Gly
    565                 570                 575
        Iₐ

AGA GGC ACG AGA ACA CAC ATC TAT TCT GGG ACC CTG ATG GAT TAC    1969
Arg Gly Thr Arg Thr His Ile Tyr Ser Gly Thr Leu Met Asp Tyr
    580                 585                 590

AAG GAT GAC GAA GGA ACT TCT GAA GAG AAG ATA AAA GTG ATC    2014
Lys Asp Asp Glu Gly Thr Ser Glu Glu Lys Ile Lys Val Ile
    595             600                 605
    IIₐ

CTC AAA GTC TTA GAC CCC AGC CAC AGG GAT ATT TCC CTG GCC TTC    2059
Leu Lys Val Leu Asp Pro Ser His Arg Asp Ile Ser Leu Ala Phe
    605                 615                 620
```

FIG. 2H

```
     IIIa
TTC GAG GCA GCC AGC ATG ATG AGA CAG GTC TCC CAC AAA CAC ATC    2104
Phe Glu Ala Ala Ser Met Met Arg Gln Val Ser His Lys His Ile
        625                 630                 635
                                                          IVa
GTG TAC CTC TAT GGC GTC TGT GTC CGC GAC GTG GAG AAT ATC ATG    2149
Val Tyr Leu Tyr Gly Val Cys Val Arg Asp Val Glu Asn Ile Met
        640                 645                 650
                      Va
GTG GAA GAG TTT GTG GAA GGG GGT CCT CTG GAT CTC TTC ATG CAC    2194
Val Glu Glu Phe Val Glu Gly Gly Pro Leu Asp Leu Phe Met His
        655                 660                 665

CGG AAA AGT GAT GTC CTT ACC ACA CCA TGG AAA TTC AAA GTT GCC    2239
Arg Lys Ser Asp Val Leu Thr Thr Pro Trp Lys Phe Lys Val Ala
        670                 675                 680

AAA CAG CTG GCC AGT GCC CTG AGC TAC TTG GAG GAT AAA GAC CTG    2284
Lys Gln Leu Ala Ser Ala Leu Ser Tyr Leu Glu Asp Lys Asp Leu
        685                 690                 695
      VIa
GTC CAT GGA AAT GTG TGT ACT AAA AAC CTC CTC CTG GCC CGT GAG    2329
Val His Gly Asn Val Cys Thr Lys Asn Leu Leu Leu Ala Arg Glu
        700                 705                 710
```

FIG. 21

```
                                              VIIa
GGA ATC GAC AGT GAG TGT GGC CCA TTC ATC AAG CTC AGT GAC CCC       2374
Gly Ile Asp Ser Glu Cys Gly Pro Phe Ile Lys Leu Ser Asp Pro
715                 720                 725

GGC ATC CCC ATT ACG GTG CTG TCT AGG CAA GAA TGC ATT GAA CGA       2419
Gly Ile Pro Ile Thr Val Leu Ser Arg Gln Glu Cys Ile Glu Arg
    730                 735                 740
        VIIIa
ATC CCA TGG ATT GCT CCT GAG TGT GTT GAG GAC TCC AAG AAC CTG       2464
Ile Pro Trp Ile Ala Pro Glu Cys Val Glu Asp Ser Lys Asn Leu
745                 750                 755
                        IXa
AGT GTG GCT GCT GAC AAG TGG AGC TTT GGA ACC ACG CTC TGG GAA       2509
Ser Val Ala Ala Asp Lys Trp Ser Phe Gly Thr Thr Leu Trp Glu
    760                 765                 770

ATC TGC TAC AAT GGC GAG ATC CCC TTG AAA GAC AAG ACG CTG ATT       2554
Ile Cys Tyr Asn Gly Glu Ile Pro Leu Lys Asp Lys Thr Leu Ile
775                 780                 785
                                        Xa
GAG AAA GAG AGA TTC TAT GAA AGC CGG TGC AGG CCA GTG ACA CCA       2599
Glu Lys Glu Arg Phe Tyr Glu Ser Arg Cys Arg Pro Val Thr Pro
    790                 795                 800
                                                        XIa
TCA TGT AAG GAG CTG GCT GAC CTC ATG ACC CGC TGC ATG AAC TAT       2644
Ser Cys Lys Glu Leu Ala Asp Leu Met Thr Arg Cys Met Asn Tyr
805                 810                 815
```

FIG. 2J

```
GAC CCC AAT CAG AGG CCT TTC TTC CGA GCC ATC ATG AGA GAC ATT      2689
Asp Pro Asn Gln Arg Pro Phe Phe Arg Ala Ile Met Arg Asp Ile
    820                 825                 830

AAT AAG CTT GAA GAG CAG AAT CCA GAT ATT GTT TCC AGA AAA AAA      2734
Asn Lys Leu Glu Glu Gln Asn Pro Asp Ile Val Ser Arg Lys Lys
    835                 840                 845

AAC CAG CCA ACT GAA GTG GAC CCC ACA CAT TTT GAG AAG CGC TTC      2779
Asn Gln Pro Thr Glu Val Asp Pro Thr His Phe Glu Lys Arg Phe
    850                 855                 860
                                    I

CTA AAG AGG ATC CGT GAC TTG GGA GAG GGC CAC TTT GGG AAG GTT      2824
Leu Lys Arg Ile Arg Asp Leu Gly Glu Gly His Phe Gly Lys Val
    865                 870                 875

GAG CTC TGC AGG TAT GAC TAT GAC CCC GAA GAC AAT ACA GGG GAG CAG GTG      2869
Glu Leu Cys Arg Tyr Asp Tyr Asp Pro Glu Asp Asn Thr Gly Glu Gln Val
    880                 885                 890
    II

GCT GTT AAA TCT CTG AAG CCT GAG AGT GGA GGT AAC CAC ATA GCT      2914
Ala Val Lys Ser Leu Lys Pro Glu Ser Gly Gly Asn His Ile Ala
    895                 900                 905

GAT CTG AAA AAG GAA ATC TTA GAG ATC TTA AGG AAC CTC TAT CAT GAG      2959
Asp Leu Lys Lys Glu Ile Leu Glu Ile Leu Arg Asn Leu Tyr His Glu
    910                 915                 920
    III
```

FIG. 2K

```
     IV
AAC ATT GTG AAG TAC AAA GGA ATC TGC ACA GAA GAC GGA GGA AAT    3004
Asn Ile Val Lys Tyr Lys Gly Ile Cys Thr Glu Asp Gly Gly Asn
            925                 930                 935
                                                     V
GGT ATT AAG CTC ATC ATG GAA TTT CTG CCT TCG GGA AGC CTT AAG    3049
Gly Ile Lys Leu Ile Met Glu Phe Leu Pro Ser Gly Ser Leu Lys
            940                 945                 950

GAA TAT CTT CCA AAG AAT AAA ATA AAC CTC AAA CAG CAG CAG        3094
Glu Tyr Leu Pro Lys Asn Lys Ile Asn Leu Lys Gln Gln Gln
            955                 960                 965

CTA AAA TAT GCC GTT CAG ATT TGT AAG GGG ATG GAC TAT TTG GGT    3139
Leu Lys Tyr Ala Val Gln Ile Cys Lys Gly Met Asp Tyr Leu Gly
            970                 975                 980
                        VI
TCT CGG CAA TAC GTT CAC CGG GAC TTG GCA GCA AGA AAT GTC CTT    3184
Ser Arg Gln Tyr Val His Arg Asp Leu Ala Ala Arg Asn Val Leu
            985                 990                 995
                                             VII
GTT GAG AGT GAA CAC CAA AAA GTG AAA ATT GGA GAC TTC GGT TTA ACC 3229
Val Glu Ser Glu His Gln Lys Val Lys Ile Gly Asp Phe Gly Leu Thr
            1000                1005                1010

AAA GCA ATT GAA ACC GAT AAG GAG TAT TAC ACC GTC AAG GAT GAC    3279
Lys Ala Ile Glu Thr Asp Lys Glu Tyr Tyr Thr Val Lys Asp Asp
            1015                1020                1025
```

FIG. 2L

```
    VIII
CGG GAC AGC CCT GTG TTT TGG TAT GCT CCA GAA TGT TTA ATG CAA    3319
Arg Asp Ser Pro Val Phe Trp Tyr Ala Pro Glu Cys Leu Met Gln
1030                    1035                    1040
                                                     IX
TCT AAA TTT TAT ATT GCC TCT GAC GTC TGG TCT TTT GGA GTC ACT    3364
Ser Lys Phe Tyr Ile Ala Ser Asp Val Trp Ser Phe Gly Val Thr
1045                    1050                    1055

CTG CAT GAG CTG CTG ACT TAC TGT GAT TCA GAT TCT AGT CCC ATG    3409
Leu His Glu Leu Leu Thr Tyr Cys Asp Ser Asp Ser Ser Pro Met
1060                    1065                    1070

GCT TTG TTC CTG AAA ATG ATA GGC CCA ACC CAT GGC CAG ATG ACA    3454
Ala Leu Phe Leu Lys Met Ile Gly Pro Thr His Gly Gln Met Thr
1075                    1080                    1085
                                                X
GTC ACA AGA CTT GTG AAT ACG TTA AAA GAA GGA GGG AAA CGC CTG CCG    3499
Val Thr Arg Leu Val Asn Thr Leu Lys Glu Gly Lys Arg Leu Pro
1090                    1095                    1100

TGC CCA CCT AAC TGT CCA GAT GAG GTT TAT CAG CTT ATG AGA AAA    3544
Cys Pro Pro Asn Cys Pro Asp Glu Val Tyr Gln Leu Met Arg Lys
1105                    1110                    1115
```

FIG. 2M

XI

```
TGC TGG GAA TTC CAA CCA TCC AAT CGG ACA AGC TTT CAG AAC CTT      3589
Cys Trp Glu Phe Gln Pro Ser Asn Arg Thr Ser Phe Gln Asn Leu
    1120                        1125                  1130

ATT GAA GGA TTT GAA GCA CTT TTA AAA TAAGAAGCAT GAATAACATT
3636
Ile Glu Gly Phe Glu Ala Leu Leu Lys
        1135                1140

TAAATTCCAC AGATTATCAA GTCCTTCTCC TGCAACAAAT GCCCAAGTCA TTTTTAAAA3696
ATTTCTAATG AAAGAAGTTT GTGTTCTGTC CAAAAAGTCA CTGAACTCAT ACTTCAGTAC3756
ATATACATGT ATAAGGCACA CTGTAGTGCT TAATATGTGT AAGGACTTCC TCTTTAAATT3816
TGCACCAGTA ACTTAGTGAC ACATAATGAC AACCAAAATA TTTGAAAGCA CTTAAGCACT3876
CCTCCCTGTG GAAAGAATAT ACCACCATTT CATCTGGCTA GTTCACCATC ACAACTGCAT3936
TACCAAAAGG GGATTTTTGA AAACGAGGAG TTGACCAAAA TAATATCTGA AGATGATTGC3996
TTTTCCCTGC TGCCAGCTGA CTGAAATGTT TTCCTGGCAC ATTAATCATA GATAAAGAAG4056
ATTGATGGAC TTAGCCCTCA AACAGTATCT ATACAGTACT AGACCATGCA TTCTTAAAAT4116
ATTAGATACC AGGTAGTATA TATTGTTTCT GTACAAAAAT GACTGTATTC TCTCACCAGT4176
AGGACTTAAA CTTTGTTTCT CCAGTGGCTT AGCTCCCTGTT CCTTTGGGTG ATCACTAG 4234
```

FIG. 3A

```
              I                                    II                      III
Domain 1  HLGRGTRTHIYSGTLMDYKDDEGTSEEKKIKVLLRVLDPS...HRDISLAGGEAASM    -60aa-
Domain 2  DLGEGHFGKVELCRT.DPEDNTGE........QVAVKSLKPES.GGNHIADLKKEEIL    -63aa-
CDC2-H    KIGEGTYGVVYKGRH....KYYG......QVVAMKKIRLESEEGVPSTAIREISLL     -55aa- VII
Domain 1  SYLEDKDLVEGNVCTKNLLLAREGIDSECGPFIKLSDPGIPITVLS......RQECIERIPW.IAPECVEDSKNLSVAADKWSFGTTLWEIC  -20aa-
Domain 2  DYLGSRQYVHRDLAARNVLVESE......VKIGDFGLTKAIETDKEYYTVKDRDSPCFW.YAPECLMQSKF.YIASDVWSFGVTLHELL      -38aa-
CDC2-H    VEHCSRRVLHRDLKPQNLLIDDKG......TIKLADGGLARAFGIPIRVYTHE...VVT.LWYRSPEVLLGSARYSTPVDIWSIGTIFAELA   -50aa-
                VI                                            VI                          IX XI
Domain 1  SRCRPVTPSCKELADLMTRCMNYDPNQRPF
Domain 2  LPCPPNCPDEVYQ..LMRKCWEFQPSNRTS
CDC2-H    LASHHVKNLDENGLDLLSKMLIYDPAKRIS
```

FIG. 4B
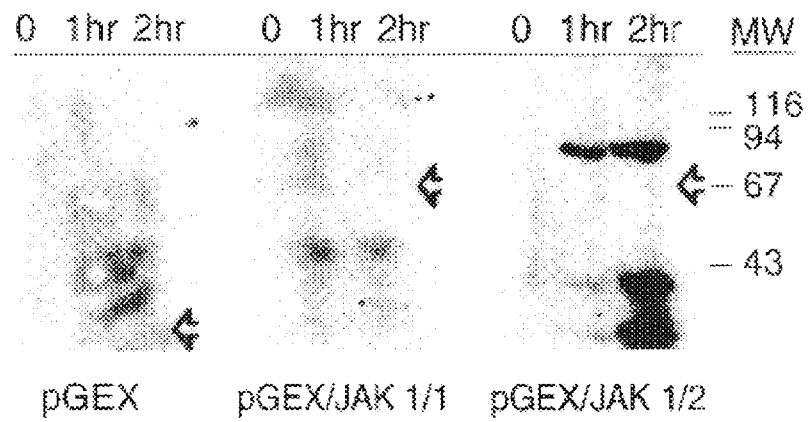
FIG. 4C
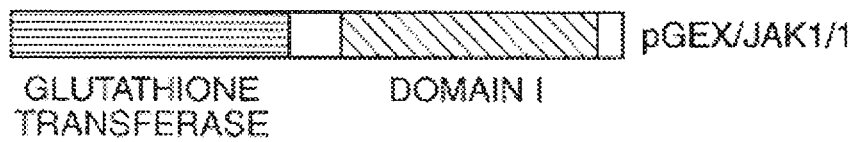

FIG. 5

```
              Ia                                        IIa          IIIa      70
VFHKIRNEDL IFNESLGQGT FTKIFKGVRR EVGDYGQLHE TE...VLLKV LDKAHRNYSE SFFEAASMMS  MJAK2
 *$*    **  $  * ** **  * *$ *    $  *   *    *$*** **  **   *    ********
SFDRILKKDL VQGEHLGRGT RTHIYSGTLM DYKDDEGTSE EKKIKVILKV LDPSHRDISL AFFEAASMMR  HJAK1

IVa                  Va                                                 140
QLSHKHLVLN YGVCVCGEEN ILVQEFVKFG SLDTYLKKNK NSINILWKLG VAKQLAWAMH FLEEKSLIHG  MJAK2
 *$****$*   *r***    ** * ***  *   ** $   $   $   **   ****** *  $**$* *$**
QVSHKHIVYL YGVCVRDVEN IMVEEFVEGG PLDLFMHRKS DVLTTPWKFK VAKQLASALS YLEDKDLVHG  HJAK1

VIa         VIIa                             VIIIa              210
NVCAKNILLI REEDRRTGNP PFIKLSDPGI SITVLPKDIS SCCFQVLQER IPWVPPECIE NPKNLTLATD  MJAK2
 *** **$** **        *  ********* ****  $      *   ** ***$ ***$* ***$$* *
NVCTKNLLLA REGIDSECGP .FIKLSDPGI PITVLSR... ....QECIER IPWIAPECVE DSKNLSVAAD  HJAK1

IXa                 Xa                        XIa               280
KWSFGTTLWE ICSGGDKPLS ALDSQRKLQF YEDKHQLPAP KWTELANLIN NCMDYEPDFR PAFRAVIRDL  MJAK2
**********  **  *$ **       *  * ** $    *    *** *   ** *$*  *  * ***$ **$
KWSFGTTLWE ICYNGEIPLK DKTLIEKERF YESRCRPVTP SCKELADLMT RCMNYDPNQR PFFRAIMRDI  HJAK1

I              350
NSLFTPDYEL LTENDMLPNM RIGALGFSGA FEDRDPTQFE ERHLKFLQQL GKGNFGSVEM CRYDPLQDNT  MJAK2
 * *     $ $$  *                 *** *  * ** $ * * * ** ** *****  ***
NKLEEQNPDI VSRKKNQPTE V.......... ....DPTHFT KRFLKRIRDL GEGHFGKVEL CRYDPE.DNT HJAK1

II              III        IV                            V         420
GEVVAVKKLQ H.STEEHLRD FEREIEILKS LQHDNIVKYK GVCYSAGRRN LRLIMEYLPY GSLRDYLQKH  MJAK2
 ** **** *     *  *$ *  $*****$  * *$****** *$*   *    $$****$** ***$$** *
GEQVAVKSLK PESGGNHIAD LKKEIEILRN LYHENIVKYK GICTEDGGNG IKLIMEFLPS GSLKEYLPKN  HJAK1

VI         VII                    490
KERIDHKKLL QYTSQICKGM EYLGTKRYIH RDLATRNILV ENENRVKIGD FGLTKVLPQD KEYYKVKEPG  MJAK2
 * $*  *  *  *  ****** $***$$ *$* ****  **$**  * *  ***** *****$$  *  **** **$
KNKINLKQQL KYAVQICKGM DYLGSRQYVH RDLAARNVLV ESEHQVKIGD FGLTKAIETD KEYYTVKDDR  HJAK1

VIII              IX                                             560
ESPIFWYAPE SLTESKFSVA SDVWSFGVVL YELFTYIEKS KSPPVEFMRM IGNDKQGQMI VFHLIELLKS  MJAK2
$**$******   *** $* ********  *   ** ** $   ** $ * $* **   ***  *  *$  **
DSPVFWYAPE CLMQSKFYIA SDVWSFGVTL HELLTYCDSD SSPMALFLKM IGPTH.GQMT VTRLVNTLKE  HJAK1

X               XI           600
NGRLPRPEGC PDEIYVIMTE CWNNNVSQRP SFRDLSFGWI KSGTV          MJAK2
 *** *  *  ***$* $*  **   *  *  ** **  *  *
GKRLPCPPNC PDEVYQLMRK CWEFQPSNRT SFQNLIEGFE ALLK           HJAK1
```

FIG. 8A

| | | | | | | | | | | | | | | | |
|---|---|---|---|---|---|---|---|---|---|---|---|---|---|---|---|
| CTG | CTT | GAT | GAC | TTT | GTC | ATG | TCT | TAC | CTT | TCC | CCT | CAG | TGG | CGG | 45 |
| Leu | Leu | Asp | Asp | Phe | Val | Met | Ser | Tyr | Leu | Ser | Pro | Gln | Trp | Arg | |
| 1 | | | | 5 | | | | | 10 | | | | | 15 | |

| | | | | | | | | | | | | | | | |
|---|---|---|---|---|---|---|---|---|---|---|---|---|---|---|---|
| CAT | GAT | TTT | GTT | CAC | GGA | TGG | ATA | AAA | GTA | CCT | GTG | ACT | CAT | GAA | 90 |
| His | Asp | Phe | Val | His | Gly | Trp | Ile | Lys | Val | Pro | Val | Thr | His | Glu | |
| | | | | 20 | | | | | 25 | | | | | 30 | |

| | | | | | | | | | | | | | | | |
|---|---|---|---|---|---|---|---|---|---|---|---|---|---|---|---|
| ACT | CAG | GAA | GAG | TGT | CTT | GGG | ATG | GCG | GTG | TTA | GAC | ATG | ATG | AGA | 135 |
| Thr | Gln | Glu | Glu | Cys | Leu | Gly | Met | Ala | Val | Leu | Asp | Met | Met | Arg | |
| | | | | 35 | | | | | 40 | | | | | 45 | |

| | | | | | | | | | | | | | | | |
|---|---|---|---|---|---|---|---|---|---|---|---|---|---|---|---|
| ATA | GCT | AAG | GAG | AAA | GAC | CAG | ACT | CCA | CTG | GCT | GTC | TAT | AAC | TCT | 180 |
| Ile | Ala | Lys | Glu | Lys | Asp | Gln | Thr | Pro | Leu | Ala | Val | Tyr | Asn | Ser | |
| | | | | 50 | | | | | 55 | | | | | 60 | |

| | | | | | | | | | | | | | | | |
|---|---|---|---|---|---|---|---|---|---|---|---|---|---|---|---|
| GTC | AGC | TAC | AAG | ACA | TTC | TTA | CCA | AAG | TGC | GTT | CGA | GCG | AAG | ATC | 225 |
| Val | Ser | Tyr | Lys | Thr | Phe | Leu | Pro | Lys | Cys | Val | Arg | Ala | Lys | Ile | |
| | | | | 65 | | | | | 70 | | | | | 75 | |

| | | | | | | | | | | | | | | | |
|---|---|---|---|---|---|---|---|---|---|---|---|---|---|---|---|
| CAA | GAC | TAT | CAC | ATT | TTA | ACC | CGG | AAG | CGA | ATC | AGG | TAC | AGA | TTT | 270 |
| Gln | Asp | Tyr | His | Ile | Leu | Thr | Arg | Lys | Arg | Ile | Arg | Tyr | Arg | Phe | |
| | | | | 80 | | | | | 85 | | | | | 90 | |

| | | | | | | | | | | | | | | | |
|---|---|---|---|---|---|---|---|---|---|---|---|---|---|---|---|
| CGC | AGA | TTC | ATT | CAG | CAA | TTC | AGT | CAA | TGT | AAA | GCC | ACT | GCC | AGG | 315 |
| Arg | Arg | Phe | Ile | Gln | Gln | Phe | Ser | Gln | Cys | Lys | Ala | Thr | Ala | Arg | |
| | | | | 95 | | | | | 100 | | | | | 105 | |

| | | | | | | | | | | | | | | | |
|---|---|---|---|---|---|---|---|---|---|---|---|---|---|---|---|
| AAC | CTA | AAA | CTT | AAG | TAT | CTT | ATA | AAC | CTG | GAA | ACC | CTG | CAG | TCT | 360 |
| Asn | Leu | Lys | Leu | Lys | Tyr | Leu | Ile | Asn | Leu | Glu | Thr | Leu | Gln | Ser | |
| | | | | 110 | | | | | 115 | | | | | 120 | |

| | | | | | | | | | | | | | | | |
|---|---|---|---|---|---|---|---|---|---|---|---|---|---|---|---|
| GCC | TTC | TAC | ACA | GAA | CAG | TTT | GAA | GTA | AAA | GAA | TCT | GCA | AGA | GGT | 405 |
| Ala | Phe | Tyr | Thr | Glu | Gln | Phe | Glu | Val | Lys | Glu | Ser | Ala | Arg | Gly | |
| | | | | 125 | | | | | 130 | | | | | 135 | |

| | | | | | | | | | | | | | | | |
|---|---|---|---|---|---|---|---|---|---|---|---|---|---|---|---|
| CCT | TCA | GGT | GAG | GAG | ATT | TTT | GCA | ACC | ATT | ATA | ATA | ACT | GGA | AAC | 450 |
| Pro | Ser | Gly | Glu | Glu | Ile | Phe | Ala | Thr | Ile | Ile | Ile | Thr | Gly | Asn | |
| | | | | 140 | | | | | 145 | | | | | 150 | |

| | | | | | | | | | | | | | | | |
|---|---|---|---|---|---|---|---|---|---|---|---|---|---|---|---|
| GGT | GGA | ATT | CAG | TGG | TCA | AGA | GGG | AAA | CAT | AAG | GAA | AGT | GAG | ACA | 495 |
| Gly | Gly | Ile | Gln | Trp | Ser | Arg | Gly | Lys | His | Lys | Glu | Ser | Glu | Thr | |
| | | | | 155 | | | | | 160 | | | | | 165 | |

FIG. 8B

```
CTG ACA GAA CAG GAC GTA CAG TTA TAT TGT GAT TTC CCT GAT ATT        540
Leu Thr Glu Gln Asp Val Gln Leu Tyr Cys Asp Phe Pro Asp Ile
            170                 175                 180

ATT GAT GTC AGT ATT AAG CAA GCA AAT CAG GAA TGC TCA ACT GAA        585
Ile Asp Val Ser Ile Lys Gln Ala Asn Gln Glu Cys Ser Thr Glu
            185                 190                 195

AGT AGA GTT GTG ACC GTC CAC AAG CAG GAC GGG AAG GTC TTG GAA        630
Ser Arg Val Val Thr Val His Lys Gln Asp Gly Lys Val Leu Glu
            200                 205                 210

ATA GAA CTT AGC TCA TTA AAA GAA GCC TTG TCA TTC GTG TCA TTA        675
Ile Glu Leu Ser Ser Leu Lys Glu Ala Leu Ser Phe Val Ser Leu
            215                 220                 225

ATT GAC GGG TAT TAC AGA CTA ACT GCG GAT GCA CAC CAT TAC CTC        720
Ile Asp Gly Tyr Tyr Arg Leu Thr Ala Asp Ala His His Tyr Leu
            230                 235                 240

TGC AAA GAG GTG GCT CCC CCA GCT GTG TTC GAG AAC ATA CAC AGC        765
Cys Lys Glu Val Ala Pro Pro Ala Val Phe Glu Asn Ile His Ser
            245                 250                 255

AAC TGC CAC GGC CCA ATT TCA ATG GAT TTT GCC ATC AGC AAA CTA        810
Asn Cys His Gly Pro Ile Ser Met Asp Phe Ala Ile Ser Lys Leu
            260                 265                 270

AAG AAG GCA GGA AAC CAG ACT GGA CTG TAT GTA CTT CGA TGT AGC        855
Lys Lys Ala Gly Asn Gln Thr Gly Leu Tyr Val Leu Arg Cys Ser
            275                 280                 285

CCT AAG GAC TTC AAC AAA TAC TTC CTG ACC TTT GCC GTT GAG CGA        900
Pro Lys Asp Phe Asn Lys Tyr Phe Leu Thr Phe Ala Val Glu Arg
            290                 295                 300

GAA AAT GTT ATT GAA TAT AAA CAC TGT TTG ATT ACA AAG AAT GAG        945
Glu Asn Val Ile Glu Tyr Lys His Cys Leu Ile Thr Lys Asn Glu
            305                 310                 315
```

FIG. 8C

```
AAT GGA GAG TAC AAC CTC AGT GGG ACT AAG AGG AAC TTC AGT AGT         990
Asn Gly Glu Tyr Asn Leu Ser Gly Thr Lys Arg Asn Phe Ser Ser
                320                 325                 330

CTT AAG GAC CTT TTG AAT TGC TAC CAG ATG GAA ACT GTG CGC TCA        1035
Leu Lys Asp Leu Leu Asn Cys Tyr Gln Met Glu Thr Val Arg Ser
                335                 340                 345

GAC AGT ATC ATC TTC CAG TTC ACC AAA TGC TGT CCT CCA AAG CCG        1080
Asp Ser Ile Ile Phe Gln Phe Thr Lys Cys Cys Pro Pro Lys Pro
                350                 355                 360

AAA GAT AAA TCA AAC CTT CTT GTC TTC AGA ACA AAT GGT GTT TCT        1125
Lys Asp Lys Ser Asn Leu Leu Val Phe Arg Thr Asn Gly Val Ser
                365                 370                 375

GAT GTT CAG CTC TCA CCA ACA TTA CAG AGG CAT AAT AAT GTG AAT        1170
Asp Val Gln Leu Ser Pro Thr Leu Gln Arg His Asn Asn Val Asn
                380                 385                 390

CAA ATG GTG TTT CAC AAA ATC AGG AAT GAA GAT TTG ATA TTT AAT        1215
Gln Met Val Phe His Lys Ile Arg Asn Glu Asp Leu Ile Phe Asn
                395                 400                 405
                      Iₐ
GAA AGC CTT GGC CAA GGC ACT TTT ACA AAA ATA TTT AAA GGT GTA        1260
Glu Ser Leu Gly Gln Gly Thr Phe Thr Lys Ile Phe Lys Gly Val
                410                 415                 420

AGA AGA GAA GTT GGA GAT TAT GGT CAG CTG CAC GAA ACC GAA GTT        1305
Arg Arg Glu Val Gly Asp Tyr Gly Gln Leu His Glu Thr Glu Val
                425                 430                 435
 IIₐ
CTT TTG AAA GTC CTA GAT AAA GCA CAT AGA AAC TAT TCA GAG TCT        1350
Leu Leu Lys Val Leu Asp Lys Ala His Arg Asn Tyr Ser Glu Ser
                440                 445                 450
  IIIₐ
TTC TTT GAA GCA GCA AGC ATG ATG AGT CAG CTT TCT CAC AAG CAT        1395
Phe Phe Glu Ala Ala Ser Met Met Ser Gln Leu Ser His Lys His
                455                 460                 465
```

FIG. 8D

```
   IVa
   TTG GTT TTG AAT TAT GGA GTA TGT GTC TGT GGA GAG GAG AAC ATT        1440
   Leu Val Leu Asn Tyr Gly Val Cys Val Cys Gly Glu Glu Asn Ile
                   470             475             480

TTG GTT CAA GAG TTT GTA AAA TTT GGA TCA CTG GAT ACA TAC CTG        1485
   Leu Val Gln Glu Phe Val Lys Phe Gly Ser Leu Asp Thr Tyr Leu
                   485             490             495

AAG AAG AAC AAA AAT TCT ATA AAT ATA TTA TGG AAA CTT GGA GTG        1530
   Lys Lys Asn Lys Asn Ser Ile Asn Ile Leu Trp Lys Leu Gly Val
                   500             505             510

GCG AAG CAG TTG GCA TGG GCC ATG CAC TTC CTC GAA GAA AAA TCC        1575
   Ala Lys Gln Leu Ala Trp Ala Met His Phe Leu Glu Glu Lys Ser
                   515             520             525
                                    VIa
   CTT ATT CAT GGG AAT GTG TGT GCT AAA AAT ATC CTG CTT ATC AGA        1620
   Leu Ile His Gly Asn Val Cys Ala Lys Asn Ile Leu Leu Ile Arg
                   530             535             540

GAA GAA GAC AGG AGA ACG GGG AAC CCA CCT TTC ATC AAA CTT AGT        1665
   Glu Glu Asp Arg Arg Thr Gly Asn Pro Pro Phe Ile Lys Leu Ser
                   545             550             555
   VIIa
   GAT CCT GGC ATT AGC ATT ACA GTT CTA CCG AAG GAC ATT TCT TCC        1710
   Asp Pro Gly Ile Ser Ile Thr Val Leu Pro Lys Asp Ile Ser Ser
                   560             565             570
                                                    VIIIa
   TGT TGT TTC CAA GTT CTT CAG GAG AGA ATA CCA TGG GTA CCA CCT        1755
   Cys Cys Phe Gln Val Leu Gln Glu Arg Ile Pro Trp Val Pro Pro
                   575             580             585

GAG TGC ATT GAG AAT CCT AAA AAT CTA ACT CTG GCA ACA GAC AAG        1800
   Glu Cys Ile Glu Asn Pro Lys Asn Leu Thr Leu Ala Thr Asp Lys
                   590             595             600
        IXa
   TGG AGC TTC GGG ACC ACT CTG TGG GAG ATC TGC AGT GGA GGA GAT        1845
   Trp Ser Phe Gly Thr Thr Leu Trp Glu Ile Cys Ser Gly Gly Asp
                   605             610             615
```

FIG. 8E

```
AAG CCC CTG AGT GCT CTG GAT TCT CAA AGA AAG CTG CAG TTC TAT      1890
Lys Pro Leu Ser Ala Leu Asp Ser Gln Arg Lys Leu Gln Phe Tyr
                620             Xa          625                 630

GAA GAT AAG CAT CAG CTT CCT GCA CCC AAG TGG ACA GAG TTG GCA      1935
Glu Asp Lys His Gln Leu Pro Ala Pro Lys Trp Thr Glu Leu Ala
                635                     640                 645
                                            XIa
AAC CTT ATA AAT AAT TGC ATG GAC TAT GAG CCA GAT TTC AGG CCT      1980
Asn Leu Ile Asn Asn Cys Met Asp Tyr Glu Pro Asp Phe Arg Pro
                650                     655                 660

GCT TTC AGA GCT GTC ATC CGT GAT CTT AAC AGC CTG TTT ACT CCA      2025
Ala Phe Arg Ala Val Ile Arg Asp Leu Asn Ser Leu Phe Thr Pro
                665                     670                 675

GAT TAT GAA CTA CTA ACA GAA AAT GAC ATG CTA CCA AAC ATG AGA      2070
Asp Tyr Glu Leu Leu Thr Glu Asn Asp Met Leu Pro Asn Met Arg
                680                     685                 690

ATA GGT GCC CTA GGG TTT TCT GGT GCT TTT GAA GAC AGG GAC CCT      2115
Ile Gly Ala Leu Gly Phe Ser Gly Ala Phe Glu Asp Arg Asp Pro
                695                     700                 705

ACA CAG TTT GAA GAG AGA CAC TTG AAG TTT CTA CAG CAG CTT GGC      2160
Thr Gln Phe Glu Glu Arg His Leu Lys Phe Leu Gln Gln Leu Gly
                710                     715                 720
 I
AAA GGT AAC TTC GGG AGT GTG GAG ATG TGC CGC TAT GAC CCG CTG      2205
Lys Gly Asn Phe Gly Ser Val Glu Met Cys Arg Tyr Asp Pro Leu
                725                     730                 735
                                    II
CAG GAC AAC ACT GGC GAG GTG GTC GCT GTG AAG AAA CTC CAG CAC      2250
Gln Asp Asn Thr Gly Glu Val Val Ala Val Lys Lys Leu Gln His
                740                     745                 750
                                                III
AGC ACT GAA GAG CAC CTC CGA GAC TTT GAG AGG GAG ATC GAG ATC      2295
Ser Thr Glu Glu His Leu Arg Asp Phe Glu Arg Glu Ile Glu Ile
                755                     760                 765
                        IV
CTG AAA TCC TTG CAG CAT GAC AAC ATC GTC AAG TAC AAG GGA GTG      2340
Leu Lys Ser Leu Gln His Asp Asn Ile Val Lys Tyr Lys Gly Val
                770                     775                 780
```

FIG. 8F

```
TGC TAC AGT GCG GGT CGG CGC AAC CTA AGA TTA ATT ATG GAA TAT         2385
Cys Tyr Ser Ala Gly Arg Arg Asn Leu Arg Leu Ile Met Glu Tyr
            785                 790                 795
        V
TTA CCA TAT GGA AGT TTA CGA GAC TAT CTC CAA AAA CAT AAA GAA         2430
Leu Pro Tyr Gly Ser Leu Arg Asp Tyr Leu Gln Lys His Lys Glu
            800                 805                 810

CGG ATA GAT CAC AAA AAA CTT CTT CAA TAC ACA TCT CAG ATA TGC         2475
Arg Ile Asp His Lys Lys Leu Leu Gln Tyr Thr Ser Gln Ile Cys
            815                 820                 825

AAG GGC ATG GAA TAT CTT GGT ACA AAA AGG TAT ATC CAC AGG GAC         2520
Lys Gly Met Glu Tyr Leu Gly Thr Lys Arg Tyr Ile His Arg Asp
            830                 835                 840
VI
CTG GCA ACA AGG AAC ATA TTG GTG GAA AAT GAG AAC AGG GTT AAA         2565
Leu Ala Thr Arg Asn Ile Leu Val Glu Asn Glu Asn Arg Val Lys
            845                 850                 855
        VII
ATA GGA GAC TTC GGA TTA ACC AAA GTC TTG CCG CAG GAC AAA GAA         2610
Ile Gly Asp Phe Gly Leu Thr Lys Val Leu Pro Gln Asp Lys Glu
            860                 865                 870

TAC TAC AAA GTA AAG GAG CCA GGG GAA AGC CCC ATA TTC TGG TAC         2655
Tyr Tyr Lys Val Lys Glu Pro Gly Glu Ser Pro Ile Phe Trp Tyr
            875                 880                 885
VIII
GCA CCT GAA TCC TTG ACG GAG AGC AAG TTT TCT GTG GCC TCA GAT         2700
Ala Pro Glu Ser Leu Thr Glu Ser Lys Phe Ser Val Ala Ser Asp
            890                 895                 900
        IX
GTG TGG AGC TTT GGA GTG GTT CTA TAC GAA CTT TTC ACA TAC ATC         2745
Val Trp Ser Phe Gly Val Val Leu Tyr Glu Leu Phe Thr Tyr Ile
            905                 910                 915

GAG AAG AGT AAA AGT CCA CCC GTG GAA TTT ATG CGA ATG ATT GGC         2790
Glu Lys Ser Lys Ser Pro Pro Val Glu Phe Met Arg Met Ile Gly
            920                 925                 930

AAT GAT AAA CAA GGG CAA ATG ATT GTG TTC CAT TTG ATA GAG CTA         2835
Asn Asp Lys Gln Gly Gln Met Ile Val Phe His Leu Ile Glu Leu
            935                 940                 945
```

FIG. 8G

```
                            X
CTG AAG AGC AAC GGA AGA TTG CCA AGG CCA GAA GGA TGC CCA GAT        2880
Leu Lys Ser Asn Gly Arg Leu Pro Arg Pro Glu Gly Cys Pro Asp
                950                 955                 960

GAG ATT TAT GTG ATC ATG ACA GAG TGC TGG AAC AAC AAT GTG AGC        2925
Glu Ile Tyr Val Ile Met Thr Glu Cys Trp Asn Asn Asn Val Ser
                965                 970                 975
        XI
CAG CGT CCC TCC TTC AGG GAC CTT TCC TTC GGG TGG ATC AAA TCC        2970
Gln Arg Pro Ser Phe Arg Asp Leu Ser Phe Gly Trp Ile Lys Ser
                980                 985                 990

GGG ACA GTA TAGCTGCGTG AAAGAGATGG CCTTACTCAG AGACCAAGCA            3019
Gly Thr Val

GACTTCCAGA ACCAGAACAA AGCTCTGTAG CCTTGTGTCT ACACATCCTT             3069

ATCATGACGC TAGCTAGGCA GAAAGAAAAC TGTGACGCCG TCTGCTCAAA             3119

AGCTTTGGAA AACGCCGTGC AGGTTTGTTT CATCACCATC TGTAAAAACC             3169

ACTGCTCAAG TCTGGCAGCA TGCTTGTGGG CTGATGCATG GAGCTCACCA             3219

CAGAGTCTCT GCATCTCCTC TGACAGAAGA AGAAAAATAG ACAATTTTCA             3269

ACTCACTTTT TTGAGAAATG GAAAAAAATT ATAATGTAAA TTTTTCAGTG             3319

TAGGAAATAC ACAGAACATA CATGTACAGT TTTTACCACG TGGAGTGTAT             3369

AATACTTTGG CCTCTTGTGT GATTTACATG AGGGCTGATG TTTGTTAATG             3419

TTTTCTAATT TTTCCATAGG TGATCTATAA TAACTTCATG ATACAAATTA             3469

AAATGCTCAG AAAATTAAAA AAAAAA                                       3495
```

FIG. 11A

```
        1                    11                   21                   31                   41                   51                   61                   71                   81                   91
J1      MQYLNIKEDCNAMAFCAKMRSSKKTEVNLEAPEPGVEVIFYLSDREPLRLGSEYTAEELCIRAAQACRISPLCHNLFALYDENTKLWYAPNRTITVDDK
J2
T2      MPLRHWGMARGSKPVGDGAQPMAAMGLKVLLHWAGPGGGEPWVTFSESSLI...AEEVCIHIAHKVGITPPCFNLFALFDAQAQVWLPPNHILEIPRD
                                                               AEE-CI-------------P-C-NLFAL--------W--PN-----

101                  111                  121                  131                  141                  151                  161                  171                  181                  191
J1      MSLRLHYRMRFYFTNWHGTNDNEQSVWRHSPKKQKNGYEKKKKIPDATPLLDASSLEYLFAQGQYDLVKCLAPIRDPK.TEQDGHDIENECLGMAVLAISHY
J2                                                                                    LLDDFVMSYLSPQWRHDFVHGWIKVPVTHETQEE.......CLGMAVLDMMRI
T2      ASLMLYFRIRFYFRNWHGMNPREPAGYRCGPPGTEASSDQTAQGMQ..LLDPASFEYLFEQGKHEFENDVASLWELS.TEEEIHHFKNESLGMAFLHLCHL
        -SL-L--R--RFYF--NWHG--N---E----P--------E----R----------LLD--S-EYLF--QG-HDFV---A-------TEEE-H---NECLGMAVL---H-
                                                         JH6→

201                  211                  221                  231                  241                  251                  261                  271                  281                  291
J1      AMMKKMQLPELPKDISYKRYIPETLNKSIRQRNLLTRMRINNVFKDFLKEFNNKTICDSSVSTHDLKVKYLATLETLTKHYGAEIFETSMLLISSENEMN
J2      AKEKDQTPLAVYNSVSYKTFLPKCVRAKIQDYHILTRKRIYRFIQQFSQCKATARN.....LKLKYLINLETLQSAFYTEQFPEVKESARGPSGEEI
T2      ALRHGIPLEEVAKKTSFKDCIPRSFRRHIRQHSALTRLRLRNVFRRFLRDFQPGRLSQQM........VMVKYLATLERLAPRFGTERVPVCHLRLLAQAEGE
        A---K----L-EV-K---SYK---IP----R--IRQ----LTR-RIRNVFRRFL---F-----------LKVKYLATLETL---FGTE-FEV--L----E--
                                                                                                             →JH6

301                  311                  321                  331                  341                  351                  361                  371                  381                  391
J1      WFHSNDGGNVLYY..........................EVMVTGNLGIQWRHKPNVVSVEKEKNKLKRKKLENKDKKDEEKNK........IREEWNNFSFFPEITHIVIKESV
J2      FAT..........................IIITGNGGIQWSRGKHKESETLTEQDLQLYCDFP............DIIDVSIKQANQECSTESRI
T2      PSYIRDSGVAPTDPGPESAAGPPTHEVLVTGTGGIQWPVEEEVNKEGSSGGSARNPQASLFGKKAKAHKAFGQPADRPREPLWAYFCDITHVVLKEHC
        ------D-G------VT-GNGGIQW-------VS-E-------L-----K---                                     -R-----S-F---ITH-V-KE--
                                                          JH5→                                                    JH4→

401                  411                  421                  431                  441                  451                  461                  471                  481                  491
J1      VSINKQDNKKMELKLSSHEEALSFVSLVDGYFRLTADAHHYLCTDVAPPLIVHNIQNGCHGPIC-EYAI.NKLRQEGSEEGMYVLRWSCTDFDNILMTVT
J2      VTVHKQDGEVLEIELSSLKEALSFVSLIDGYYRLTADAHHYLCKEVAPPAVLENIHSNCHGPISMDFAI.SKLKKAGNQTGLYVLRCSPKDFNKYFLTFA
T2      VSIHRQDNKCLELSLPSRAAALSFESLVDGYFRLTADSSHYLCHEVAPPRLVMSIRDGIHGPLLEPFVQQAKLRP..LEDGLYLIHWSTSHPYRLLILTVA
        VSIHKQDNK-LEL-LSS--EALSFVSLVDGYFRLTADAHHYLC--EVAPP---V-NI--GCHGPI---FAI--KLR--G-E-GLYVLRWS--DF----LTVA
                                                                                                         →JH4
```

FIG. 11B

```
     501                      511                  521                 531                  541                  551                   561                   571                  581                  591
J1   CFEKSEQVQGAQKQF KNF QIEVQKGRYSLHGSDRSFPSLGDLMSHLKKQILRTDNISFMLKRCCQPKPREISNLLVATKKAQEWQPVYPMSQLSFDRILK
J2   VER.... ENVIEYKHCLITKNENGEYNLSGTKRNFSSLKDLLNCYQMETVRSDSIIFQFTKCCPPKPKDKSNLLVFRTNGVSDVQLSPTLQRHNNVNQM
T2   QRSQAPDGMQSLRLRKF.PIEQQDGAFVLEGWGRSFPSVRELGAALQGCLLRAGDDCFSLRRCCLPQPGETSNLIIMRGARASPRTL.NLSQLSFHRVDQ
                                  K---------IE-Q--G-Y-L-G--RSFPSL-DL----LQ----LR-D-I-F-L-RCC-PKP-E-SNLLV-R----S---L-P-SQLSF-R---
                    JH3→
     601                     611                  621                  631                  641                  651                  661                  671                  681                  691
J1   KD.......LVQGEHLGRGTRTHIYSGTLMDYKDDEGTSEEKK..................IKVILKVLDPSHRDISLAFFEAASMRQVSHKHIVYLYGVC
J2   VFHKIRNEDLIFNESLGQGFFTKIFKGVRREVGDY.GQLHETE......................VLLKVLDKAHRNYSESFFEAASMMSQLSHKHLVLNYGVC
T2   KE........ITQLSHLGQGTRTNVYEGRLRVEGS..GDPEEGKMDEDPLVPGRDRGQELRVLKVLDPSHHDIALAFYETASLMSQVSHTHLAFVHGVC
     K-                 L-Q--EHLGQGTRT--IY-G--LR---GD--G--EE-K.....--V--LKVLDPSHRDISLAFFEAASMMSQVSHKHLV---YGVC
             JH2
     701                   711                  721                  731                  741                  751                  761                  771                  781                  791
J1   VRDVENIMVEEFVEGGPLDLFMHRKSDVLTTPWKFKVAKQLASALSYLEDKDLVHGNVCTKNLLLAREGIDSECGPFIKLSDPGIPITVLSRQECIERIP
J2   VCGEENILVQEFVKFGSLDTYLKKNKNSINILWKLGVAKQLAWAMHFLEEKSLIHGNVCAKNILLIREEDRRTGNPFIKLSDPGISITVLPKDISSCCF.
T2   VRGPENSMVTEYVEHGPLDVWLRRERGHVPMAWKMVVAQQLASALSYLENKNLVHGNVCGRNILLARLGLAEGTSPFIKLSDPGCGLGALSREERVERIP
     VRG--ENIMV-EFVE-GPLD---L-R---------WK---VAKQLASALSYLE--K--LVHGNVC--KNILLAREG--------PFIKLSDPGI--ITVLSR-E---ERIP
     801                  811                  821                  831                  841                  851                  861                  871                  881                  891
J1   ............WIAPECVED.SKNLSVAADKWSFGTTLWEICYNGEIPLKDKTLIEKERFYESRCRPVTPSCKELADLMTRCMNYDPNQRPFFRAIMRDINKLE
J2   QVLQERIPWVPPECIEN.PKNLTLATDKWSFGTTLWEICSGGDKPLSALDSQRKLQFYEDKHQLPAPKWTELANLINNCMDYEPDFRPAFRAVIRDLNSLF
T2   ............WLAPECLPGGANSLSTAMDKWGFGATLLEICFDGEAPLQSRSPSEKEHFYQRQHRLPEPSCPQLATLTSQCLTYEPTQRPSFATILRDLTAVQ
     W--APEC--E-----NNLS--A--DKWSFGTTLWEIC---GE--PL-----CM-YEP--QRP-FRAI-RDLN-L--
```

FIG. 11C

```
         901        911        921        931        941        951        961        971        981        991
    J1  EQNPDIVSRKKNQP................................TEVDPTHF.KRFLKRIRDLGEGHFGKVELCRYDP.EDNTGEQVAVKSLKPESGGNHIADLKKEIEILRNLYHE
    J2  TPDYELLTENDMLPNMRIGALGFSGAFEDRDPTQFEERHLKFLQQLGKGNFGSVEMCRYDPLQDNTGEVAVKKLQH.STEEHLRDFEREIEILKSLQHD
    T2  PHNLADVLTVNRDS................................PAVGPTTFHKRYLKKIRDLGEGHFGKVSLYCYDPTNDGTGEMVAVKALKADCGPQHRSGWKQEIDILRTLYHE
        --N---V-----P-------[--JH2]---VDPT-F-KR-LK-IRDLGEGHFGKVELCRYDP--DNTGE-VAVK-LK--SG--H--D-K-EIEILR-LYHE
                                       [JH1→]
        1001       1011       1021       1031       1041       1051       1061       1071       1081       1091
    J1  NIVKYKGICTEDGGNGIKLIMEFLPSGSLKEYLPKNKNRKINLKQQLKYAVQICKGMDYLGSRQYVHRDLAARNVLVESEHQVKIGDFGLTKAIETDKEYY
    J2  NIVKYKGVCYSAGRRNLRLIMEYLPYGSLRDYLQKHKERIDHKKLLQYTSQICKGMEYLGTKRYIHRDLATRNILVENENRVKIGDFGLTKVLPQDKEYY
    T2  HIIKYKGCC.EDQGE.KSLVMEYVPLGSLRDYLPRHS..IGLAQLLFAQQICEGMAYLHAHDYIHRDLAARNVLLDNDRLVKIGDFGLAKAVPEGHEYY
        NIVKYKG-C-EDGG-----LIMEYLP-GSLRDYLPKHK--I-LKQLL-YA-QICKGM-YLG---YIHRDLAARNVLVENE---VKIGDFGLTKA-P-DKEYY
        1101       1111       1121       1131       1141       1151       1161       1171       1181       1191
    J1  TVKDDRDSPVFWYAPECLMQSKFYIASDVWSFGVTLHELLTYCDSDSSPMALFLKMIG.PTHGQMTVTRLVNTLKEGKRLPCPPNCPDEVYQLMRKCWEF
    J2  KVKEPGESPIFWYAPESLTESKFSVASDVWSFGVVLYELFTYIEKSKSPPVEFMRMIGNDKQGQMIVFHLIELLKSNGRLPREGCPDEIYVIMTECWNN
    T2  RVREDGDSPVFWYAPECLKEYNFYYASDVWSFGVTLYELLTHCDSSQSPPTKFLELIG.IAQGQMTVLRLTELLEAGERLPRPDKCPCEVYHLMKNCWET
        -VKEDGDSPVFWYAPECL-ASDVWSFGVTLYELLTYCDSS-SPP--FL-MIG---QGQMTV-RL-ELLK-G-RLPRP--CPDEVY--LM--CWE-
        1201       1211       1221       1231
    J1  NVSQRPSFRDLSFGWIKSGTV*
    J2  QPSNRTSFQNLIEGFEALLK*
    T2  EASFRPTFENSIPILKTVHEKYQGQAPSVSSVC*
        ---S-RPSF-NLI-G---[←JH1]
```

FIG. 12

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
( A ) LENGTH: 4234 base pairs
( B ) TYPE: nucleic acid
( C ) STRANDEDNESS: single
( D ) TOPOLOGY: linear ( i i ) MOLECULE TYPE: nucleic acid ( x i ) SEQUENCE DESCRIPTION: SEQ ID NO: 1:

```
TGGCCGCCTA  GCGAGCTGCC  GGTCGACCCC  AGCCAGCCGA  GCGACGGGCG  CTGCCTGGCC         60

CAGGGCACAC  GGAAGTGCGC  TTCTCTGAAG  TAGCTTTGGA  AAGTAGAGAA  GAAAATCCAG        120

TTTGCTTCTT  GGAGAACACT  GGACAGCTGA  ATAA  ATG  CAG  TAT  CTA  AAT              169
```

|   |   |   |   |   |   |   | Met | Gln | Tyr | Leu | Asn |   |   |   |
|---|---|---|---|---|---|---|-----|-----|-----|-----|-----|---|---|---|
|   |   |   |   |   |   |   |     |     |     |     | -10 |   |   |   |

```
ATA AAA GAG GAC TGC AAT GCC ATG GCT TTC TGT GCT AAA ATG AGG       214
Ile Lys Glu Asp Cys Asn Ala Met Ala Phe Cys Ala Lys Met Arg
     -5              +1              5

AGC TCC AAG AAG ACT GAG GTG AAC CTG GAG GCC CCT GAG CCA GGG       259
Ser Ser Lys Lys Thr Glu Val Asn Leu Glu Ala Pro Glu Pro Gly
         10              15                  20

GTG GAA GTG ATC TTC TAT CTG TCG GAC AGG GAG CCC CTC CGG CTG       304
Val Glu Val Ile Phe Tyr Leu Ser Asp Arg Glu Pro Leu Arg Leu
     25              30              35

GGC AGT GGA GAG TAC ACA GCA GAG GAA CTG TGC ATC AGG GCT GCA       349
Gly Ser Gly Glu Tyr Thr Ala Glu Glu Leu Cys Ile Arg Ala Ala
     40              45              50

CAG GCA TGC CGT ATC TCT CCT CTT TGT CAC AAC CTC TTT GCC CTG       394
Gln Ala Cys Arg Ile Ser Pro Leu Cys His Asn Leu Phe Ala Leu
     55              60              65

TAT GAC GAG AAC ACC AAG CTC TGG TAT GCT CCA AAT CGC ACC ATC       439
Tyr Asp Glu Asn Thr Lys Leu Trp Tyr Ala Pro Asn Arg Thr Ile
     70              75              80

ACC GTT GAT GAC AAG ATG TCC CTC CGG CTC CAC TAC CGG ATG AGG       484
Thr Val Asp Asp Lys Met Ser Leu Arg Leu His Tyr Arg Met Arg
     85              90              95

TTC TAT TTC ACC AAT TGG CAT GGA ACC AAC GAC AAT GAG CAG TCA       529
Phe Tyr Phe Thr Asn Trp His Gly Thr Asn Asp Asn Glu Gln Ser
     100             105             110

GTG TGG CGT CAT TCT CCA AAG AAG CAG AAA AAT GGC TAC GAG AAA       574
Val Trp Arg His Ser Pro Lys Lys Gln Lys Asn Gly Tyr Glu Lys
     115             120             125

AAA AAG ATT CCA GAT GCA ACC CCT CTC CTT GAT GCC AGC TCA CTG       619
Lys Lys Ile Pro Asp Ala Thr Pro Leu Leu Asp Ala Ser Ser Leu
     130             135             140

GAG TAT CTG TTT GCT CAG GGA CAG TAT GAT TTG GTG AAA TGC CTG       664
Glu Tyr Leu Phe Ala Gln Gly Gln Tyr Asp Leu Val Lys Cys Leu
     145             150             155

GCT CCT ATT CGA GAC CCC AAG ACC GAG CAG GAT GGA CAT GAT ATT       709
Ala Pro Ile Arg Asp Pro Lys Thr Glu Gln Asp Gly His Asp Ile
     160             165             170

GAG AAC GAG TGT CTA GGG ATG GCT GTC CTG GCC ATC TCA CAC TAT       754
Glu Asn Glu Cys Leu Gly Met Ala Val Leu Ala Ile Ser His Tyr
     175             180             185

GCC ATG ATG AAG AAG ATG CAG TTG CCA GAA CTG CCC AAG GAC ATC       799
Ala Met Met Lys Lys Met Gln Leu Pro Glu Leu Pro Lys Asp Ile
     190             195             200

AGC TAC AAG CGA TAT ATT CCA GAA ACA TTG AAT AAG TCC ATC AGA       844
Ser Tyr Lys Arg Tyr Ile Pro Glu Thr Leu Asn Lys Ser Ile Arg
     205             210             215

CAG AGG AAC CTT CTC ACC AGG ATG CGG ATA AAT AAT GTT TTC AAG       889
Gln Arg Asn Leu Leu Thr Arg Met Arg Ile Asn Asn Val Phe Lys
     220             225             230

GAT TTC CTA AAG GAA TTT AAC AAC AAG ACC ATT TGT GAC AGC AGC       934
Asp Phe Leu Lys Glu Phe Asn Asn Lys Thr Ile Cys Asp Ser Ser
     235             240             245

GTG TCC ACG CAT GAC CTG AAG GTG AAA TAC TTG GCT ACC TTG GAA       979
Val Ser Thr His Asp Leu Lys Val Lys Tyr Leu Ala Thr Leu Glu
     250             255             260

ACT TTG ACA AAA CAT TAC GGT GCT GAA ATA TTT GAG ACT TCC ATG      1024
Thr Leu Thr Lys His Tyr Gly Ala Glu Ile Phe Glu Thr Ser Met
     265             270             275

TTA CTG ATT TCA TCA GAA AAT GAG ATG AAT TGG TTT CAT TCG AAT      1069
```

```
           Leu  Leu  Ile  Ser  Ser  Glu  Asn  Glu  Met  Asn  Trp  Phe  His  Ser  Asn
                280                     285                     290

GAC  GGT  GGA  AAC  GTT  CTC  TAC  TAC  GAA  GTG  ATG  GTG  ACT  GGG  AAT          1114
      Asp  Gly  Gly  Asn  Val  Leu  Tyr  Tyr  Glu  Val  Met  Val  Thr  Gly  Asn
           295                     300                     305

CTT  GGA  ATC  CAG  TGG  AGG  CAT  AAA  CCA  AAT  GTT  GTT  TCT  GTT  GAA          1159
      Leu  Gly  Ile  Gln  Trp  Arg  His  Lys  Pro  Asn  Val  Val  Ser  Val  Glu
           310                     315                     320

AAG  GAA  AAA  AAT  AAA  CTG  AAG  CGG  AAA  AAA  CTG  GAA  AAT  AAA  GAC          1204
      Lys  Glu  Lys  Asn  Lys  Leu  Lys  Arg  Lys  Lys  Leu  Glu  Asn  Lys  Asp
           325                     330                     335

AAG  AAG  GAT  GAG  GAG  AAA  AAC  AAG  ATC  CGG  GAA  GAG  TGG  AAC  AAT          1249
      Lys  Lys  Asp  Glu  Glu  Lys  Asn  Lys  Ile  Arg  Glu  Glu  Trp  Asn  Asn
           340                     345                     350

TTT  TCA  TTC  TTC  CCT  GAA  ATC  ACT  CAC  ATT  GTA  ATA  AAG  GAG  TCT          1294
      Phe  Ser  Phe  Phe  Pro  Glu  Ile  Thr  His  Ile  Val  Ile  Lys  Glu  Ser
           355                     360                     365

GTG  GTC  AGC  ATT  AAC  AAG  CAG  GAC  AAC  AAG  AAA  ATG  GAA  CTG  AAG          1339
      Val  Val  Ser  Ile  Asn  Lys  Gln  Asp  Asn  Lys  Lys  Met  Glu  Leu  Lys
           370                     375                     380

CTC  TCT  TCC  CAC  GAG  GAG  GCC  TTG  TCC  TTT  GTG  TCC  CTG  GTA  GAT          1384
      Leu  Ser  Ser  His  Glu  Glu  Ala  Leu  Ser  Phe  Val  Ser  Leu  Val  Asp
           385                     390                     395

GGC  TAC  TTC  CGG  CTC  ACA  GCA  GAT  GCC  CAT  CAT  TAC  CTC  TGC  ACC          1429
      Gly  Tyr  Phe  Arg  Leu  Thr  Ala  Asp  Ala  His  His  Tyr  Leu  Cys  Thr
           400                     405                     410

GAC  GTG  GCC  CCC  CCG  TTG  ATC  GTC  CAC  AAC  ATA  CAG  AAT  GGC  TGT          1474
      Asp  Val  Ala  Pro  Pro  Leu  Ile  Val  His  Asn  Ile  Gln  Asn  Gly  Cys
           415                     420                     425

CAT  GGT  CCA  ATC  TGT  ACA  GAA  TAC  GCC  ATC  AAT  AAA  TTG  CGG  CAA          1519
      His  Gly  Pro  Ile  Cys  Thr  Glu  Tyr  Ala  Ile  Asn  Lys  Leu  Arg  Gln
           430                     435                     440

GAA  GGA  AGC  GAG  GAG  GGG  ATG  TAC  GTG  CTG  AGG  TGG  AGC  TGC  ACC          1564
      Glu  Gly  Ser  Glu  Glu  Gly  Met  Tyr  Val  Leu  Arg  Trp  Ser  Cys  Thr
           445                     450                     455

GAC  TTT  GAC  AAC  ATC  CTC  ATG  ACC  GTC  ACC  TGC  TTT  GAG  AAG  TCT          1609
      Asp  Phe  Asp  Asn  Ile  Leu  Met  Thr  Val  Thr  Cys  Phe  Glu  Lys  Ser
           460                     465                     470

GAG  CAG  GTG  CAG  GGT  GCC  CAG  AAG  CAG  TTC  AAG  AAC  TTT  CAG  ATC          1654
      Glu  Gln  Val  Gln  Gly  Ala  Gln  Lys  Gln  Phe  Lys  Asn  Phe  Gln  Ile
           475                     480                     485

GAG  GTG  CAG  AAG  GGC  CGC  TAC  AGT  CTG  CAC  GGT  TCG  GAC  CGC  AGC          1699
      Glu  Val  Gln  Lys  Gly  Arg  Tyr  Ser  Leu  His  Gly  Ser  Asp  Arg  Ser
           490                     495                     500

TTC  CCC  AGC  TTG  GGA  GAC  CTC  ATG  AGC  CAC  CTC  AAG  AAG  CAG  ATC          1744
      Phe  Pro  Ser  Leu  Gly  Asp  Leu  Met  Ser  His  Leu  Lys  Lys  Gln  Ile
           505                     510                     515

CTG  CGC  ACG  GAT  AAC  ATC  AGC  TTC  ATG  CTA  AAA  CGC  TGC  TGC  CAG          1789
      Leu  Arg  Thr  Asp  Asn  Ile  Ser  Phe  Met  Leu  Lys  Arg  Cys  Cys  Gln
           520                     525                     530

CCC  AAG  CCC  CGA  GAA  ATC  TCC  AAC  CTG  CTG  GTG  GCT  ACT  AAG  AAA          1834
      Pro  Lys  Pro  Arg  Glu  Ile  Ser  Asn  Leu  Leu  Val  Ala  Thr  Lys  Lys
           535                     540                     545

GCC  CAG  GAG  TGG  CAG  CCC  GTC  TAC  CCC  ATG  AGC  CAG  CTG  AGT  TTC          1879
      Ala  Gln  Glu  Trp  Gln  Pro  Val  Tyr  Pro  Met  Ser  Gln  Leu  Ser  Phe
           550                     555                     560

GAT  CGG  ATC  CTC  AAG  AAG  GAT  CTG  GTG  CAG  GGC  GAG  CAC  CTT  GGG          1924
      Asp  Arg  Ile  Leu  Lys  Lys  Asp  Leu  Val  Gln  Gly  Glu  His  Leu  Gly
           565                     570                     575

AGA  GGC  ACG  AGA  ACA  CAC  ATC  TAT  TCT  GGG  ACC  CTG  ATG  GAT  TAC          1969
```

| | | | | | | | | | | | | | | |
|---|---|---|---|---|---|---|---|---|---|---|---|---|---|---|
| Arg | Gly | Thr | Arg | Thr | His | Ile | Tyr | Ser | Gly | Thr | Leu | Met | Asp | Tyr |
| | 580 | | | | 585 | | | | | 590 | | | | |

| AAG | GAT | GAC | GAA | GGA | ACT | TCT | GAA | GAG | AAG | AAG | ATA | AAA | GTG | ATC | 2014 |
|---|---|---|---|---|---|---|---|---|---|---|---|---|---|---|---|
| Lys | Asp | Asp | Glu | Gly | Thr | Ser | Glu | Glu | Lys | Lys | Ile | Lys | Val | Ile | |
| 595 | | | | | 600 | | | | | 605 | | | | | |

| CTC | AAA | GTC | TTA | GAC | CCC | AGC | CAC | AGG | GAT | ATT | TCC | CTG | GCC | TTC | 2059 |
|---|---|---|---|---|---|---|---|---|---|---|---|---|---|---|---|
| Leu | Lys | Val | Leu | Asp | Pro | Ser | His | Arg | Asp | Ile | Ser | Leu | Ala | Phe | |
| | 605 | | | | 615 | | | | | 620 | | | | | |

| TTC | GAG | GCA | GCC | AGC | ATG | ATG | AGA | CAG | GTC | TCC | CAC | AAA | CAC | ATC | 2104 |
|---|---|---|---|---|---|---|---|---|---|---|---|---|---|---|---|
| Phe | Glu | Ala | Ala | Ser | Met | Met | Arg | Gln | Val | Ser | His | Lys | His | Ile | |
| 625 | | | | | 630 | | | | | 635 | | | | | |

| GTG | TAC | CTC | TAT | GGC | GTC | TGT | GTC | CGC | GAC | GTG | GAG | AAT | ATC | ATG | 2149 |
|---|---|---|---|---|---|---|---|---|---|---|---|---|---|---|---|
| Val | Tyr | Leu | Tyr | Gly | Val | Cys | Val | Arg | Asp | Val | Glu | Asn | Ile | Met | |
| 640 | | | | | 645 | | | | | 650 | | | | | |

| GTG | GAA | GAG | TTT | GTG | GAA | GGG | GGT | CCT | CTG | GAT | CTC | TTC | ATG | CAC | 2194 |
|---|---|---|---|---|---|---|---|---|---|---|---|---|---|---|---|
| Val | Glu | Glu | Phe | Val | Glu | Gly | Gly | Pro | Leu | Asp | Leu | Phe | Met | His | |
| 655 | | | | | 660 | | | | | 665 | | | | | |

| CGG | AAA | AGT | GAT | GTC | CTT | ACC | ACA | CCA | TGG | AAA | TTC | AAA | GTT | GCC | 2239 |
|---|---|---|---|---|---|---|---|---|---|---|---|---|---|---|---|
| Arg | Lys | Ser | Asp | Val | Leu | Thr | Thr | Pro | Trp | Lys | Phe | Lys | Val | Ala | |
| 670 | | | | | 675 | | | | | 680 | | | | | |

| AAA | CAG | CTG | GCC | AGT | GCC | CTG | AGC | TAC | TTG | GAG | GAT | AAA | GAC | CTG | 2284 |
|---|---|---|---|---|---|---|---|---|---|---|---|---|---|---|---|
| Lys | Gln | Leu | Ala | Ser | Ala | Leu | Ser | Tyr | Leu | Glu | Asp | Lys | Asp | Leu | |
| 685 | | | | | 690 | | | | | 695 | | | | | |

| GTC | CAT | GGA | AAT | GTG | TGT | ACT | AAA | AAC | CTC | CTC | CTG | GCC | CGT | GAG | 2329 |
|---|---|---|---|---|---|---|---|---|---|---|---|---|---|---|---|
| Val | His | Gly | Asn | Val | Cys | Thr | Lys | Asn | Leu | Leu | Leu | Ala | Arg | Glu | |
| 700 | | | | | 705 | | | | | 710 | | | | | |

| GGA | ATC | GAC | AGT | GAG | TGT | GGC | CCA | TTC | ATC | AAG | CTC | AGT | GAC | CCC | 2374 |
|---|---|---|---|---|---|---|---|---|---|---|---|---|---|---|---|
| Gly | Ile | Asp | Ser | Glu | Cys | Gly | Pro | Phe | Ile | Lys | Leu | Ser | Asp | Pro | |
| 715 | | | | | 720 | | | | | 725 | | | | | |

| GGC | ATC | CCC | ATT | ACG | GTG | CTG | TCT | AGG | CAA | GAA | TGC | ATT | GAA | CGA | 2419 |
|---|---|---|---|---|---|---|---|---|---|---|---|---|---|---|---|
| Gly | Ile | Pro | Ile | Thr | Val | Leu | Ser | Arg | Gln | Glu | Cys | Ile | Glu | Arg | |
| 730 | | | | | 735 | | | | | 740 | | | | | |

| ATC | CCA | TGG | ATT | GCT | CCT | GAG | TGT | GTT | GAG | GAC | TCC | AAG | AAC | CTG | 2464 |
|---|---|---|---|---|---|---|---|---|---|---|---|---|---|---|---|
| Ile | Pro | Trp | Ile | Ala | Pro | Glu | Cys | Val | Glu | Asp | Ser | Lys | Asn | Leu | |
| 745 | | | | | 750 | | | | | 755 | | | | | |

| AGT | GTG | GCT | GCT | GAC | AAG | TGG | AGC | TTT | GGA | ACC | ACG | CTC | TGG | GAA | 2509 |
|---|---|---|---|---|---|---|---|---|---|---|---|---|---|---|---|
| Ser | Val | Ala | Ala | Asp | Lys | Trp | Ser | Phe | Gly | Thr | Thr | Leu | Trp | Glu | |
| 760 | | | | | 765 | | | | | 770 | | | | | |

| ATC | TGC | TAC | AAT | GGC | GAG | ATC | CCC | TTG | AAA | GAC | AAG | ACG | CTG | ATT | 2554 |
|---|---|---|---|---|---|---|---|---|---|---|---|---|---|---|---|
| Ile | Cys | Tyr | Asn | Gly | Glu | Ile | Pro | Leu | Lys | Asp | Lys | Thr | Leu | Ile | |
| 775 | | | | | 780 | | | | | 785 | | | | | |

| GAG | AAA | GAG | AGA | TTC | TAT | GAA | AGC | CGG | TGC | AGG | CCA | GTG | ACA | CCA | 2599 |
|---|---|---|---|---|---|---|---|---|---|---|---|---|---|---|---|
| Glu | Lys | Glu | Arg | Phe | Tyr | Glu | Ser | Arg | Cys | Arg | Pro | Val | Thr | Pro | |
| 790 | | | | | 795 | | | | | 800 | | | | | |

| TCA | TGT | AAG | GAG | CTG | GCT | GAC | CTC | ATG | ACC | CGC | TGC | ATG | AAC | TAT | 2644 |
|---|---|---|---|---|---|---|---|---|---|---|---|---|---|---|---|
| Ser | Cys | Lys | Glu | Leu | Ala | Asp | Leu | Met | Thr | Arg | Cys | Met | Asn | Tyr | |
| 805 | | | | | 810 | | | | | 815 | | | | | |

| GAC | CCC | AAT | CAG | AGG | CCT | TTC | TTC | CGA | GCC | ATC | ATG | AGA | GAC | ATT | 2689 |
|---|---|---|---|---|---|---|---|---|---|---|---|---|---|---|---|
| Asp | Pro | Asn | Gln | Arg | Pro | Phe | Phe | Arg | Ala | Ile | Met | Arg | Asp | Ile | |
| 820 | | | | | 825 | | | | | 830 | | | | | |

| AAT | AAG | CTT | GAA | GAG | CAG | AAT | CCA | GAT | ATT | GTT | TCC | AGA | AAA | AAA | 2734 |
|---|---|---|---|---|---|---|---|---|---|---|---|---|---|---|---|
| Asn | Lys | Leu | Glu | Glu | Gln | Asn | Pro | Asp | Ile | Val | Ser | Arg | Lys | Lys | |
| 835 | | | | | 840 | | | | | 845 | | | | | |

| AAC | CAG | CCA | ACT | GAA | GTG | GAC | CCC | ACA | CAT | TTT | GAG | AAG | CGC | TTC | 2779 |
|---|---|---|---|---|---|---|---|---|---|---|---|---|---|---|---|
| Asn | Gln | Pro | Thr | Glu | Val | Asp | Pro | Thr | His | Phe | Glu | Lys | Arg | Phe | |
| 850 | | | | | 855 | | | | | 860 | | | | | |

| CTA | AAG | AGG | ATC | CGT | GAC | TTG | GGA | GAG | GGC | CAC | TTT | GGG | AAG | GTT | 2824 |
|---|---|---|---|---|---|---|---|---|---|---|---|---|---|---|---|
| Leu | Lys | Arg | Ile | Arg | Asp | Leu | Gly | Glu | Gly | His | Phe | Gly | Lys | Val | |
| 865 | | | | | 870 | | | | | 875 | | | | | |

| GAG | CTC | TGC | AGG | TAT | GAC | CCC | GAA | GAC | AAT | ACA | GGG | GAG | CAG | GTG | 2869 |
|---|---|---|---|---|---|---|---|---|---|---|---|---|---|---|---|

```
                Glu  Leu  Cys  Arg  Tyr  Asp  Pro  Glu  Asp  Asn  Thr  Gly  Glu  Gln  Val
                     880                 885                           890

GCT  GTT  AAA  TCT  CTG  AAG  CCT  GAG  AGT  GGA  GGT  AAC  CAC  ATA  GCT                 2914
Ala  Val  Lys  Ser  Leu  Lys  Pro  Glu  Ser  Gly  Gly  Asn  His  Ile  Ala
     895                 900                           905

GAT  CTG  AAA  AAG  GAA  ATC  GAG  ATC  TTA  AGG  AAC  CTC  TAT  CAT  GAG                 2959
Asp  Leu  Lys  Lys  Glu  Ile  Glu  Ile  Leu  Arg  Asn  Leu  Tyr  His  Glu
     910                 915                           920

AAC  ATT  GTG  AAG  TAC  AAA  GGA  ATC  TGC  ACA  GAA  GAC  GGA  GGA  AAT                 3004
Asn  Ile  Val  Lys  Tyr  Lys  Gly  Ile  Cys  Thr  Glu  Asp  Gly  Gly  Asn
     925                 930                           935

GGT  ATT  AAG  CTC  ATC  ATG  GAA  TTT  CTG  CCT  TCG  GGA  AGC  CTT  AAG                 3049
Gly  Ile  Lys  Leu  Ile  Met  Glu  Phe  Leu  Pro  Ser  Gly  Ser  Leu  Lys
     940                 945                           950

GAA  TAT  CTT  CCA  AAG  AAT  AAG  AAC  AAA  ATA  AAC  CTC  AAA  CAG  CAG                 3094
Glu  Tyr  Leu  Pro  Lys  Asn  Lys  Asn  Lys  Ile  Asn  Leu  Lys  Gln  Gln
     955                 960                           965

CTA  AAA  TAT  GCC  GTT  CAG  ATT  TGT  AAG  GGG  ATG  GAC  TAT  TTG  GGT                 3139
Leu  Lys  Tyr  Ala  Val  Gln  Ile  Cys  Lys  Gly  Met  Asp  Tyr  Leu  Gly
     970                 975                           980

TCT  CGG  CAA  TAC  GTT  CAC  CGG  GAC  TTG  GCA  GCA  AGA  AAT  GTC  CTT                 3184
Ser  Arg  Gln  Tyr  Val  His  Arg  Asp  Leu  Ala  Ala  Arg  Asn  Val  Leu
     985                 990                           995

GTT  GAG  AGT  GAA  CAC  CAA  GTG  AAA  ATT  GGA  GAC  TTC  GGT  TTA  ACC                 3229
Val  Glu  Ser  Glu  His  Gln  Val  Lys  Ile  Gly  Asp  Phe  Gly  Leu  Thr
     1000                1005                          1010

AAA  GCA  ATT  GAA  ACC  GAT  AAG  GAG  TAT  TAC  ACC  GTC  AAG  GAT  GAC                 3274
Lys  Ala  Ile  Glu  Thr  Asp  Lys  Glu  Tyr  Tyr  Thr  Val  Lys  Asp  Asp
     1015                1020                          1025

CGG  GAC  AGC  CCT  GTG  TTT  TGG  TAT  GCT  CCA  GAA  TGT  TTA  ATG  CAA                 3319
Arg  Asp  Ser  Pro  Val  Phe  Trp  Tyr  Ala  Pro  Glu  Cys  Leu  Met  Gln
     1030                1035                          1040

TCT  AAA  TTT  TAT  ATT  GCC  TCT  GAC  GTC  TGG  TCT  TTT  GGA  GTC  ACT                 3364
Ser  Lys  Phe  Tyr  Ile  Ala  Ser  Asp  Val  Trp  Ser  Phe  Gly  Val  Thr
     1045                1050                          1055

CTG  CAT  GAG  CTG  CTG  ACT  TAC  TGT  GAT  TCA  GAT  TCT  AGT  CCC  ATG                 3409
Leu  His  Glu  Leu  Leu  Thr  Tyr  Cys  Asp  Ser  Asp  Ser  Ser  Pro  Met
     1060                1065                          1070

GCT  TTG  TTC  CTG  AAA  ATG  ATA  GGC  CCA  ACC  CAT  GGC  CAG  ATG  ACA                 3454
Ala  Leu  Phe  Leu  Lys  Met  Ile  Gly  Pro  Thr  His  Gly  Gln  Met  Thr
     1075                1080                          1085

GTC  ACA  AGA  CTT  GTG  AAT  ACG  TTA  AAA  GAA  GGA  AAA  CGC  CTG  CCG                 3499
Val  Thr  Arg  Leu  Val  Asn  Thr  Leu  Lys  Glu  Gly  Lys  Arg  Leu  Pro
     1090                1095                          1100

TGC  CCA  CCT  AAC  TGT  CCA  GAT  GAG  GTT  TAT  CAG  CTT  ATG  AGA  AAA                 3544
Cys  Pro  Pro  Asn  Cys  Pro  Asp  Glu  Val  Tyr  Gln  Leu  Met  Arg  Lys
     1105                1110                          1115

TGC  TGG  GAA  TTC  CAA  CCA  TCC  AAT  CGG  ACA  AGC  TTT  CAG  AAC  CTT                 3589
Cys  Trp  Glu  Phe  Gln  Pro  Ser  Asn  Arg  Thr  Ser  Phe  Gln  Asn  Leu
     1120                1135                          1130

ATT  GAA  GGA  TTT  GAA  GCA  CTT  TTA  AAA  TAAGAAGCAT  GAATAACATT                       3636
Ile  Glu  Gly  Phe  Glu  Ala  Leu  Leu  Lys
     1135                1140

TAAATTCCAC  AGATTATCAA  GTCCTTCTCC  TGCAACAAAT  GCCCAAGTCA  TTTTTTAAAA                    3696

ATTTCTAATG  AAAGAAGTTT  GTGTTCTGTC  CAAAAAGTCA  CTGAACTCAT  ACTTCAGTAC                    3756

ATATACATGT  ATAAGGCACA  CTGTAGTGCT  TAATATGTGT  AAGGACTTCC  TCTTTAAATT                    3816

TGCACCAGTA  ACTTAGTGAC  ACATAATGAC  AACCAAAATA  TTTGAAAGCA  CTTAAGCACT                    3876

CCTCCTTGTG  GAAAGAATAT  ACCACCATTT  CATCTGGCTA  GTTCACCATC  ACAACTGCAT                    3936
```

```
TACCAAAAGG GGATTTTTGA AAACGAGGAG TTGACCAAAA TAATATCTGA AGATGATTGC    3996

TTTTCCCTGC TGCCAGCTGA CTGAAATGTT TTCCTGGCAC ATTAATCATA GATAAAGAAG    4056

ATTGATGGAC TTAGCCCTCA AACAGTATCT ATACAGTACT AGACCATGCA TTCTTAAAAT    4116

ATTAGATACC AGGTAGTATA TATTGTTTCT GTACAAAAAT GACTGTATTC TCTCACCAGT    4176

AGGACTTAAA CTTTGTTTCT CCAGTGGCTT AGCTCCTGTT CCTTGGGTG ATCACTAG      4234
```

( 2 ) INFORMATION FOR SEQ ID NO:2:

( i ) SEQUENCE CHARACTERISTICS:
        ( A ) LENGTH: 3495 base pairs
        ( B ) TYPE: nucleic acid
        ( D ) STRANDEDNESS: single
        ( D ) TOPOLOGY: linear ( i i ) MOLECULE TYPE: nucleic acid ( x i ) SEQUENCE DESCRIPTION: SEQ ID NO: 2:

```
CTG CTT GAT GAC TTT GTC ATG TCT TAC CTT TCC CCT CAG TGG CGG         45
Leu Leu Asp Asp Phe Val Met Ser Tyr Leu Ser Pro Gln Trp Arg
 1               5                  10                  15

CAT GAT TTT GTT CAC GGA TGG ATA AAA GTA CCT GTG ACT CAT GAA         90
His Asp Phe Val His Gly Trp Ile Lys Val Pro Val Thr His Glu
                20                  25                  30

ACT CAG GAA GAG TGT CTT GGG ATG GCG GTG TTA GAC ATG ATG AGA        135
Thr Gln Glu Glu Cys Leu Gly Met Ala Val Leu Asp Met Met Arg
                35                  40                  45

ATA GCT AAG GAG AAA GAC CAG ACT CCA CTG GCT GTC TAT AAC TCT        180
Ile Ala Lys Glu Lys Asp Gln Thr Pro Leu Ala Val Tyr Asn Ser
                50                  55                  60

GTC AGC TAC AAG ACA TTC TTA CCA AAG TGC GTT CGA GCG AAG ATC        225
Val Ser Tyr Lys Thr Phe Leu Pro Lys Cys Val Arg Ala Lys Ile
                65                  70                  75

CAA GAC TAT CAC ATT TTA ACC CGG AAG CGA ATC AGG TAC AGA TTT        270
Gln Asp Tyr His Ile Leu Thr Arg Lys Arg Ile Arg Tyr Arg Phe
                80                  85                  90

CGC AGA TTC ATT CAG CAA TTC AGT CAA TGT AAA GCC ACT GCC AGG        315
Arg Arg Phe Ile Gln Gln Phe Ser Gln Cys Lys Ala Thr Ala Arg
                95                 100                 105

AAC CTA AAA CTT AAG TAT CTT ATA AAC CTG GAA ACC CTG CAG TCT        360
Asn Leu Lys Leu Lys Tyr Leu Ile Asn Leu Glu Thr Leu Gln Ser
               110                 115                 120

GCC TTC TAC ACA GAA CAG TTT GAA GTA AAA GAA TCT GCA AGA GGT        405
Ala Phe Tyr Thr Glu Gln Phe Glu Val Lys Glu Ser Ala Arg Gly
               125                 130                 135

CCT TCA GGT GAG GAG ATT TTT GCA ACC ATT ATA ATA ACT GGA AAC        450
Pro Ser Gly Glu Glu Ile Phe Ala Thr Ile Ile Ile Thr Gly Asn
               140                 145                 150

GGT GGA ATT CAG TGG TCA AGA GGG AAA CAT AAG GAA AGT GAG ACA        495
Gly Gly Ile Gln Trp Ser Arg Gly Lys His Lys Glu Ser Glu Thr
               155                 160                 165

CTG ACA GAA CAG GAC GTA CAG TTA TAT TGT GAT TTC CCT GAT ATT        540
Leu Thr Glu Gln Asp Val Gln Leu Tyr Cys Asp Phe Pro Asp Ile
               170                 175                 180

ATT GAT GTC AGT ATT AAG CAA GCA AAT CAG GAA TGC TCA ACT GAA        585
Ile Asp Val Ser Ile Lys Gln Ala Asn Gln Glu Cys Ser Thr Glu
               185                 190                 195

AGT AGA GTT GTG ACC GTC CAC AAG CAG GAC GGG AAG GTC TTG GAA        630
Ser Arg Val Val Thr Val His Lys Gln Asp Gly Lys Val Leu Glu
               200                 205                 210
```

| | | | | | | | | | | | | | | |
|---|---|---|---|---|---|---|---|---|---|---|---|---|---|---|
| ATA | GAA | CTT | AGC | TCA | TTA | AAA | GAA | GCC | TTG | TCA | TTC | GTG | TCA | TTA | 675 |
| Ile | Glu | Leu | Ser | Ser 215 | Leu | Lys | Glu | Ala | Leu 220 | Ser | Phe | Val | Ser | Leu 225 | |
| ATT | GAC | GGG | TAT | TAC | AGA | CTA | ACT | GCG | GAT | GCA | CAC | CAT | TAC | CTC | 720 |
| Ile | Asp | Gly | Tyr | Tyr 230 | Arg | Leu | Thr | Ala | Asp 235 | Ala | His | His | Tyr | Leu 240 | |
| TGC | AAA | GAG | GTG | GCT | CCC | CCA | GCT | GTG | TTC | GAG | AAC | ATA | CAC | AGC | 765 |
| Cys | Lys | Glu | Val | Ala 245 | Pro | Pro | Ala | Val | Phe 250 | Glu | Asn | Ile | His | Ser 255 | |
| AAC | TGC | CAC | GGC | CCA | ATT | TCA | ATG | GAT | TTT | GCC | ATC | AGC | AAA | CTA | 810 |
| Asn | Cys | His | Gly | Pro 260 | Ile | Ser | Met | Asp | Phe 265 | Ala | Ile | Ser | Lys | Leu 270 | |
| AAG | AAG | GCA | GGA | AAC | CAG | ACT | GGA | CTG | TAT | GTA | CTT | CGA | TGT | AGC | 855 |
| Lys | Lys | Ala | Gly | Asn 275 | Gln | Thr | Gly | Leu | Tyr 280 | Val | Leu | Arg | Cys | Ser 285 | |
| CCT | AAG | GAC | TTC | AAC | AAA | TAC | TTC | CTG | ACC | TTT | GCC | GTT | GAG | CGA | 900 |
| Pro | Lys | Asp | Phe | Asn 290 | Lys | Tyr | Phe | Leu | Thr 295 | Phe | Ala | Val | Glu | Arg 300 | |
| GAA | AAT | GTT | ATT | GAA | TAT | AAA | CAC | TGT | TTG | ATT | ACA | AAG | AAT | GAG | 945 |
| Glu | Asn | Val | Ile | Glu 305 | Tyr | Lys | His | Cys | Leu 310 | Ile | Thr | Lys | Asn | Glu 315 | |
| AAT | GGA | GAG | TAC | AAC | CTC | AGT | GGG | ACT | AAG | AGG | AAC | TTC | AGT | AGT | 990 |
| Asn | Gly | Glu | Tyr | Asn 320 | Leu | Ser | Gly | Thr | Lys 325 | Arg | Asn | Phe | Ser | Ser 330 | |
| CTT | AAG | GAC | CTT | TTG | AAT | TGC | TAC | CAG | ATG | GAA | ACT | GTG | CGC | TCA | 1035 |
| Leu | Lys | Asp | Leu | Leu 335 | Asn | Cys | Tyr | Gln | Met 340 | Glu | Thr | Val | Arg | Ser 345 | |
| GAC | AGT | ATC | ATC | TTC | CAG | TTC | ACC | AAA | TGC | TGT | CCT | CCA | AAG | CCG | 1080 |
| Asp | Ser | Ile | Ile | Phe 350 | Gln | Phe | Thr | Lys | Cys 355 | Cys | Pro | Pro | Lys | Pro 360 | |
| AAA | GAT | AAA | TCA | AAC | CTT | CTT | GTC | TTC | AGA | ACA | AAT | GGT | GTT | TCT | 1125 |
| Lys | Asp | Lys | Ser | Asn 365 | Leu | Leu | Val | Phe | Arg 370 | Thr | Asn | Gly | Val | Ser 375 | |
| GAT | GTT | CAG | CTC | TCA | CCA | ACA | TTA | CAG | AGG | CAT | AAT | AAT | GTG | AAT | 1170 |
| Asp | Val | Gln | Leu | Ser 380 | Pro | Thr | Leu | Gln | Arg 385 | His | Asn | Asn | Val | Asn 390 | |
| CAA | ATG | GTG | TTT | CAC | AAA | ATC | AGG | AAT | GAA | GAT | TTG | ATA | TTT | AAT | 1215 |
| Gln | Met | Val | Phe | His 395 | Lys | Ile | Arg | Asn | Glu 400 | Asp | Leu | Ile | Phe | Asn 405 | |
| GAA | AGC | CTT | GGC | CAA | GGC | ACT | TTT | ACA | AAA | ATA | TTT | AAA | GGT | GTA | 1260 |
| Glu | Ser | Leu | Gly | Gln 410 | Gly | Thr | Phe | Thr | Lys 415 | Ile | Phe | Lys | Gly | Val 420 | |
| AGA | AGA | GAA | GTT | GGA | GAT | TAT | GGT | CAG | CTG | CAC | GAA | ACC | GAA | GTT | 1305 |
| Arg | Arg | Glu | Val | Gly 425 | Asp | Tyr | Gly | Gln | Leu 430 | His | Glu | Thr | Glu | Val 435 | |
| CTT | TTG | AAA | GTC | CTA | GAT | AAA | GCA | CAT | AGA | AAC | TAT | TCA | GAG | TCT | 1350 |
| Leu | Leu | Lys | Val | Leu 440 | Asp | Lys | Ala | His | Arg 445 | Asn | Tyr | Ser | Glu | Ser 450 | |
| TTC | TTT | GAA | GCA | GCA | AGC | ATG | ATG | AGT | CAG | CTT | TCT | CAC | AAG | CAT | 1395 |
| Phe | Phe | Glu | Ala | Ala 455 | Ser | Met | Met | Ser | Gln 460 | Leu | Ser | His | Lys | His 465 | |
| TTG | GTT | TTG | AAT | TAT | GGA | GTC | TGT | GTC | TGT | GGA | GAG | GAG | AAC | ATT | 1440 |
| Leu | Val | Leu | Asn | Tyr 470 | Gly | Val | Cys | Val | Cys 475 | Gly | Glu | Glu | Asn | Ile 480 | |
| TTG | GTT | CAA | GAG | TTT | GTA | AAA | TTT | GGA | TCA | CTG | GAT | ACA | TAC | CTG | 1485 |
| Leu | Val | Gln | Glu | Phe 485 | Val | Lys | Phe | Gly | Ser 490 | Leu | Asp | Thr | Tyr | Leu 495 | |
| AAG | AAG | AAC | AAA | AAT | TCT | ATA | AAT | ATA | TTA | TGG | AAA | CTT | GGA | GTG | 1530 |
| Lys | Lys | Asn | Lys | Asn 500 | Ser | Ile | Asn | Ile | Leu 505 | Trp | Lys | Leu | Gly | Val 510 | |

| | | | | | | | | | | | | | | |
|---|---|---|---|---|---|---|---|---|---|---|---|---|---|---|
| GCG | AAG | CAG | TTG | GCA | TGG | GCC | ATG | CAC | TTC | CTC | GAA | GAA | AAA | TCC | 1575
| Ala | Lys | Gln | Leu | Ala | Trp | Ala | Met | His | Phe | Leu | Glu | Glu | Lys | Ser |
| | | | 515 | | | | 520 | | | | | | 525 | |
| CTT | ATT | CAT | GGG | AAT | GTG | TGT | GCT | AAA | AAT | ATC | CTG | CTT | ATC | AGA | 1620
| Leu | Ile | His | Gly | Asn | Val | Cys | Ala | Lys | Asn | Ile | Leu | Leu | Ile | Arg |
| | | | 530 | | | | 535 | | | | | | 540 | |
| GAA | GAA | GAC | AGG | AGA | ACG | GGG | AAC | CCA | CCT | TTC | ATC | AAA | CTT | AGT | 1665
| Glu | Glu | Asp | Arg | Arg | Thr | Gly | Asn | Pro | Pro | Phe | Ile | Lys | Leu | Ser |
| | | | 545 | | | | 550 | | | | | | 555 | |
| GAT | CCT | GGC | ATT | AGC | ATT | ACA | GTT | CTA | CCG | AAG | GAC | ATT | TCT | TCC | 1710
| Asp | Pro | Gly | Ile | Ser | Ile | Thr | Val | Leu | Pro | Lys | Asp | Ile | Ser | Ser |
| | | | 560 | | | | 565 | | | | | | 570 | |
| TGT | TGT | TTC | CAA | GTT | CTT | CAG | GAG | AGA | ATA | CCA | TGG | GTA | CCA | CCT | 1755
| Cys | Cys | Phe | Gln | Val | Leu | Gln | Glu | Arg | Ile | Pro | Trp | Val | Pro | Pro |
| | | | 575 | | | | 580 | | | | | | 585 | |
| GAG | TGC | ATT | GAG | AAT | CCT | AAA | AAT | CTA | ACT | CTG | GCA | ACA | GAC | AAG | 1800
| Glu | Cys | Ile | Glu | Asn | Pro | Lys | Asn | Leu | Thr | Leu | Ala | Thr | Asp | Lys |
| | | | 590 | | | | 595 | | | | | | 600 | |
| TGG | AGC | TTC | GGG | ACC | ACT | CTG | TGG | GAG | ATC | TGC | AGT | GGA | GGA | GAT | 1845
| Trp | Ser | Phe | Gly | Thr | Thr | Leu | Trp | Glu | Ile | Cys | Ser | Gly | Gly | Asp |
| | | | 605 | | | | 610 | | | | | | 615 | |
| AAG | CCC | CTG | AGT | GCT | CTG | GAT | TCT | CAA | AGA | AAG | CTG | CAG | TTC | TAT | 1890
| Lys | Pro | Leu | Ser | Ala | Leu | Asp | Ser | Gln | Arg | Lys | Leu | Gln | Phe | Tyr |
| | | | 620 | | | | 625 | | | | | | 630 | |
| GAA | GAT | AAG | CAT | CAG | CTT | CCT | GCA | CCC | AAG | TGG | ACA | GAG | TTG | GCA | 1935
| Glu | Asp | Lys | His | Gln | Leu | Pro | Ala | Pro | Lys | Trp | Thr | Glu | Leu | Ala |
| | | | 635 | | | | 640 | | | | | | 645 | |
| AAC | CTT | ATA | AAT | AAT | TGC | ATG | GAC | TAT | GAG | CCA | GAT | TTC | AGG | CCT | 1980
| Asn | Leu | Ile | Asn | Asn | Cys | Met | Asp | Tyr | Glu | Pro | Asp | Phe | Arg | Pro |
| | | | 650 | | | | 655 | | | | | | 660 | |
| GCT | TTC | AGA | GCT | GTC | ATC | CGT | GAT | CTT | AAC | AGC | CTG | TTT | ACT | CCA | 2025
| Ala | Phe | Arg | Ala | Val | Ile | Arg | Asp | Leu | Asn | Ser | Leu | Phe | Thr | Pro |
| | | | 665 | | | | 670 | | | | | | 675 | |
| GAT | TAT | GAA | CTA | CTA | ACA | GAA | AAT | GAC | ATG | CTA | CCA | AAC | ATG | AGA | 2070
| Asp | Tyr | Glu | Leu | Leu | Thr | Glu | Asn | Asp | Met | Leu | Pro | Asn | Met | Arg |
| | | | 680 | | | | 685 | | | | | | 690 | |
| ATA | GGT | GCC | CTA | GGG | TTT | TCT | GGT | GCT | TTT | GAA | GAC | AGG | GAC | CCT | 2115
| Ile | Gly | Ala | Leu | Gly | Phe | Ser | Gly | Ala | Phe | Glu | Asp | Arg | Asp | Pro |
| | | | 695 | | | | 700 | | | | | | 705 | |
| ACA | CAG | TTT | GAA | GAG | AGA | CAC | TTG | AAG | TTT | CTA | CAG | CAG | CTT | GGC | 2160
| Thr | Gln | Phe | Glu | Glu | Arg | His | Leu | Lys | Phe | Leu | Gln | Gln | Leu | Gly |
| | | | 710 | | | | 715 | | | | | | 720 | |
| AAA | GGT | AAC | TTC | GGG | AGT | GTG | GAG | ATG | TGC | CGC | TAT | GAC | CCG | CTG | 2205
| Lys | Gly | Asn | Phe | Gly | Ser | Val | Glu | Met | Cys | Arg | Tyr | Asp | Pro | Leu |
| | | | 725 | | | | 730 | | | | | | 735 | |
| CAG | GAC | AAC | ACT | GGC | GAG | GTG | GTC | GCT | GTG | AAG | AAA | CTC | CAG | CAC | 2250
| Gln | Asp | Asn | Thr | Gly | Glu | Val | Val | Ala | Val | Lys | Lys | Leu | Gln | His |
| | | | 740 | | | | 745 | | | | | | 750 | |
| AGC | ACT | GAA | GAG | CAC | CTC | CGA | GAC | TTT | GAG | AGG | GAG | ATC | GAG | ATC | 2295
| Ser | Thr | Glu | Glu | His | Leu | Arg | Asp | Phe | Glu | Arg | Glu | Ile | Glu | Ile |
| | | | 755 | | | | 760 | | | | | | 765 | |
| CTG | AAA | TCC | TTG | CAG | CAT | GAC | AAC | ATC | GTC | AAG | TAC | AAG | GGA | GTG | 2340
| Leu | Lys | Ser | Leu | Gln | His | Asp | Asn | Ile | Val | Lys | Tyr | Lys | Gly | Val |
| | | | 770 | | | | 775 | | | | | | 780 | |
| TGC | TAC | AGT | GCG | GGT | CGG | CGC | AAC | CTA | AGA | TTA | ATT | ATG | GAA | TAT | 2385
| Cys | Tyr | Ser | Ala | Gly | Arg | Arg | Asn | Leu | Arg | Leu | Ile | Met | Glu | Tyr |
| | | | 785 | | | | 790 | | | | | | 795 | |
| TTA | CCA | TAT | GGA | AGT | TTA | CGA | GAC | TAT | CTC | CAA | AAA | CAT | AAA | GAA | 2430
| Leu | Pro | Tyr | Gly | Ser | Leu | Arg | Asp | Tyr | Leu | Gln | Lys | His | Lys | Glu |
| | | | 800 | | | | 805 | | | | | | 810 | |

| | | | | | | | | | | | | | | | |
|---|---|---|---|---|---|---|---|---|---|---|---|---|---|---|---|
| CGG | ATA | GAT | CAC | AAA | AAA | CTT | CTT | CAA | TAC | ACA | TCT | CAG | ATA | TGC | 2475 |
| Arg | Ile | Asp | His | Lys<br>815 | Lys | Leu | Leu | Gln | Tyr<br>820 | Thr | Ser | Gln | Ile | Cys<br>825 | |
| AAG | GGC | ATG | GAA | TAT | CTT | GGT | ACA | AAA | AGG | TAT | ATC | CAC | AGG | GAC | 2520 |
| Lys | Gly | Met | Glu<br>830 | Tyr | Leu | Gly | Thr | Lys | Arg<br>835 | Tyr | Ile | His | Arg | Asp<br>840 | |
| CTG | GCA | ACA | AGG | AAC | ATA | TTG | GTG | GAA | AAT | GAG | AAC | AGG | GTT | AAA | 2565 |
| Leu | Ala | Thr | Arg | Asn<br>845 | Ile | Leu | Val | Glu | Asn<br>850 | Glu | Asn | Arg | Val | Lys<br>855 | |
| ATA | GGA | GAC | TTC | GGA | TTA | ACC | AAA | GTC | TTG | CCG | CAG | GAC | AAA | GAA | 2610 |
| Ile | Gly | Asp | Phe | Gly<br>860 | Leu | Thr | Lys | Val | Leu<br>865 | Pro | Gln | Asp | Lys | Glu<br>870 | |
| TAC | TAC | AAA | GTA | AAG | GAG | CCA | GGG | GAA | AGC | CCC | ATA | TTC | TGG | TAC | 2655 |
| Tyr | Tyr | Lys | Val | Lys<br>875 | Glu | Pro | Gly | Glu | Ser<br>880 | Pro | Ile | Phe | Trp | Tyr<br>885 | |
| GCA | CCT | GAA | TCC | TTG | ACG | GAG | AGC | AAG | TTT | TCT | GTG | GCC | TCA | GAT | 2700 |
| Ala | Pro | Glu | Ser | Leu<br>890 | Thr | Glu | Ser | Lys | Phe<br>895 | Ser | Val | Ala | Ser | Asp<br>900 | |
| GTG | TGG | AGC | TTT | GGA | GTG | GTT | CTA | TAC | GAA | CTT | TTC | ACA | TAC | ATC | 2745 |
| Val | Trp | Ser | Phe | Gly<br>905 | Val | Val | Leu | Tyr | Glu<br>910 | Leu | Phe | Thr | Tyr | Ile<br>915 | |
| GAG | AAG | AGT | AAA | AGT | CCA | CCC | GTG | GAA | TTT | ATG | CGA | ATG | ATT | GGC | 2790 |
| Glu | Lys | Ser | Lys | Ser<br>920 | Pro | Pro | Val | Glu | Phe<br>925 | Met | Arg | Met | Ile | Gly<br>930 | |
| AAT | GAT | AAA | CAA | GGG | CAA | ATG | ATT | GTG | TTC | CAT | TTG | ATA | GAG | CTA | 2835 |
| Asn | Asp | Lys | Gln | Gly<br>935 | Gln | Met | Ile | Val | Phe<br>940 | His | Leu | Ile | Glu | Leu<br>945 | |
| CTG | AAG | AGC | AAC | GGA | AGA | TTG | CCA | AGG | CCA | GAA | GGA | TGC | CCA | GAT | 2880 |
| Leu | Lys | Ser | Asn | Gly<br>950 | Arg | Leu | Pro | Arg | Pro<br>955 | Glu | Gly | Cys | Pro | Asp<br>960 | |
| GAG | ATT | TAT | GTG | ATC | ATG | ACA | GAG | TGC | TGG | AAC | AAC | AAT | GTG | AGC | 2925 |
| Glu | Ile | Tyr | Val | Ile<br>965 | Met | Thr | Glu | Cys | Trp<br>970 | Asn | Asn | Asn | Val | Ser<br>975 | |
| CAG | CGT | CCC | TCC | TTC | AGG | GAC | CTT | TCC | TTC | GGG | TGG | ATC | AAA | TCC | 2970 |
| Gln | Arg | Pro | Ser | Phe<br>980 | Arg | Asp | Leu | Ser | Phe<br>985 | Gly | Trp | Ile | Lys | Ser<br>990 | |

| | | | | | |
|---|---|---|---|---|---|
| GGG | ACA | GTA | TAGCTGCGTG | AAAGAGATGG | CCTTACTCAG AGACCAAGCA | 3019 |
| Gly | Thr | Val | | | | |

| | | | | |
|---|---|---|---|---|
| GACTTCCAGA | ACCAGAACAA | AGCTCTGTAG | CCTTGTGTCT | ACACATCCTT | 3069 |
| ATCATGACGC | TAGCTAGGCA | GAAAGAAAAC | TGTGACGCCG | TCTGCTCAAA | 3119 |
| AGCTTTGGAA | AACGCCGTGC | AGGTTTGTTT | CATCACCATC | TGTAAAAACC | 3169 |
| ACTGCTCAAG | TCTGGCAGCA | TGCTTGTGGG | CTGATGCATG | GAGCTCACCA | 3219 |
| CAGAGTCTCT | GCATCTCCTC | TGACAGAAGA | AGAAAAATAG | ACAATTTTCA | 3269 |
| ACTCACTTTT | TTGAGAAATG | GAAAAAAATT | ATAATGTAAA | TTTTTCAGTG | 3319 |
| TAGGAAATAC | ACAGAACATA | CATGTACAGT | TTTTACCACG | TGGAGTGTAT | 3369 |
| AATACTTTGG | CCTCTTGTGT | GATTTACATG | AGGGCTGATG | TTTGTTAATG | 3419 |
| TTTTCTAATT | TTTCCATAGG | TGATCTATAA | TAACTTCATG | ATACAAATTA | 3469 |
| AAATGCTCAG | AAAATTAAAA | AAAAAA | | | 3495 |

( 2 ) INFORMATION FOR SEQ ID NO:3:

( i ) SEQUENCE CHARACTERISTICS:
        ( A ) LENGTH: 6 amino acid residues
        ( B ) TYPE: amino acid
        ( D ) TOPOLOGY: linear ( i x ) FEATURE:

(D) OTHER INFORMATION: Xaa in positions 2, 4 and 5 is
unknown.

(xi) SEQUENCE DESCRIPTION: SEQ ID NO: 3:

Gly Xaa Gly Xaa Xaa Gly
            5

(2) INFORMATION FOR SEQ ID NO:4:

(i) SEQUENCE CHARACTERISTICS:
       (A) LENGTH: 16 amino acid residues
       (B) TYPE: amino acid
       (D) TOPOLOGY: linear (xi) SEQUENCE DESCRIPTION: SEQ ID NO: 4:

Thr Ser Phe Gln Asn Leu Ile Glu Cys Phe Glu Ala Leu Leu Lys Cys
            5                   10                  15

(2) INFORMATION FOR SEQ ID NO:5:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (xi) SEQUENCE DESCRIPTION: SEQ ID NO: 5:

TACACCTTTA AATATTTTG T                                               21

(2) INFORMATION FOR SEQ ID NO:6:

(i) SEQUENCE CHARACTERISTICS:
       (A) LENGTH: 17 base pairs
       (B) TYPE: nucleic acid
       (C) STRANDEDNESS: single
       (D) TOPOLOGY: linear (xi) SEQUENCE DESCRIPTION: SEQ ID NO: 6:

CTCGAGTCGA CGAATTC                                                   17

(2) INFORMATION FOR SEQ ID NO:7:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (xi) SEQUENCE DESCRIPTION: SEQ ID NO: 7:

CTTGCTTAAT ACTGACATCA                                                20

(2) INFORMATION FOR SEQ ID NO:8:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (xi) SEQUENCE DESCRIPTION: SEQ ID NO: 8:

CTTGCTTAAT ACTGACATCA                                                20

(2) INFORMATION FOR SEQ ID NO:9:

(i) SEQUENCE CHARACTERISTICS:
       (A) LENGTH: 9 base pairs
       (B) TYPE: nucleic acid
       (C) STRANDEDNESS: single ( D ) TOPOLOGY: linear ( x i ) SEQUENCE DESCRIPTION: SEQ ID NO: 9:

TAAATGCAG                                                                                                        9

( 2 ) INFORMATION FOR SEQ ID NO:10:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 10:

GCCATGGCT                                                                                                        9

( 2 ) INFORMATION FOR SEQ ID NO:11:

( i ) SEQUENCE CHARACTERISTICS:
        ( A ) LENGTH: 8 amino acid residues
        ( B ) TYPE: amino acid
        ( D ) TOPOLOGY: linear ( x i ) SEQUENCE DESCRIPTION: SEQ ID NO: 11:

Gly Leu Tyr Val Leu Arg Trp Ser
                      8

( 2 ) INFORMATION FOR SEQ ID NO:12:

( i ) SEQUENCE CHARACTERISTICS:
        ( A ) LENGTH: 7 amino acid residues
        ( B ) TYPE: amino acid
        ( D ) TOPOLOGY: linear ( x i ) SEQUENCE DESCRIPTION: SEQ ID NO: 12:

Val Asp Gly Tyr Phe Arg Ile
             5

( 2 ) INFORMATION FOR SEQ ID NO: 13:

( i ) SEQUENCE CHARACTERISTICS:
        ( A ) LENGTH: 47 amino acids
        ( B ) TYPE: amino acid
        ( D ) TOPOLOGY: linear ( x i ) SEQUENCE DESCRIPTION: SEQ ID NO: 13:

Lys Ile Gly Glu Gly Thr Tyr Gly Val Val Tyr Lys Gly Arg His
             5                        10                     15

Lys Thr Thr Gly Gln Val Val Ala Met Lys Lys Ile Arg Leu Glu
            20                      25                   30

Ser Glu Glu Glu Gly Val Pro Ser Thr Ala Ile Arg Glu Ile Ser
            35                      40                   45

Leu Leu ( 2 ) INFORMATION FOR SEQ ID NO: 14:

( i ) SEQUENCE CHARACTERISTICS:
        ( A ) LENGTH: 82 amino acids
        ( B ) TYPE: amino acid
        ( D ) TOPOLOGY: linear ( x i ) SEQUENCE DESCRIPTION: SEQ ID NO: 14:

Val Phe Cys His Ser Arg Arg Val Leu His Arg Asp Leu Lys Pro
               5                      10                   15

Gln Asn Leu Leu Ile Asp Asp Lys Gly Thr Ile Lys Leu Ala Asp

|  |  |  |  | 20 |  |  |  |  | 25 |  |  |  |  | 30 |
|---|---|---|---|---|---|---|---|---|---|---|---|---|---|---|

Phe Gly Leu Ala Arg Ala Phe Gly Ile Pro Ile Arg Val Tyr Thr
                35                      40                      45

His Glu Val Val Thr Leu Trp Tyr Arg Ser Pro Glu Val Leu Leu
                50                      55                      60

Gly Ser Ala Arg Tyr Ser Thr Pro Val Asp Ile Trp Ser Ile Gly
                65                      70                      75

Thr Ile Phe Ala Glu Leu Ala
                80

(2) INFORMATION FOR SEQ ID NO: 15:

(i) SEQUENCE CHARACTERISTICS:
        (A) LENGTH: 30 amino acids
        (B) TYPE: amino acid
        (D) TOPOLOGY: linear (x i) SEQUENCE DESCRIPTION: SEQ ID NO: 15:

Leu Ala Ser His His Val Lys Asn Leu Asp Glu Asn Gly Leu Asp
                5                       10                      15

Leu Leu Ser Lys Met Leu Ile Tyr Asp Pro Ala Lys Arg Ile Ser
                20                      25                      30

(2) INFORMATION FOR SEQ ID NO: 16:

(i) SEQUENCE CHARACTERISTICS:
        (A) LENGTH: 601 amino acids
        (B) TYPE: amino acid
        (D) TOPOLOGY: linear (x i) SEQUENCE DESCRIPTION: SEQ ID NO: 16:

Val Phe His Lys Ile Arg Asn Glu Asp Leu Ile Phe Asn Glu Ser
                5                       10                      15

Leu Gly Gln Gly Thr Phe Thr Lys Ile Phe Lys Gly Val Arg Arg
                20                      25                      30

Glu Val Gly Asp Tyr Gly Gln Leu His Glu Thr Glu Val Leu Leu
                35                      40                      45

Lys Val Leu Asp Lys Ala His Arg Asn Tyr Ser Glu Ser Phe Phe
                50                      55                      60

Glu Ala Ala Ser Met Met Ser Gln Leu Ser His Lys His Leu Val
                65                      70                      75

Leu Asn Tyr Gly Val Cys Val Cys Gly Glu Glu Asn Ile Leu Val
                80                      85                      90

Gln Glu Phe Val Lys Phe Gly Ser Leu Asp Thr Tyr Leu Lys Lys
                95                      100                     105

Asn Lys Asn Ser Ile Asn Ile Leu Trp Lys Leu Gly Val Ala Lys
                110                     115                     120

Gln Leu Ala Trp Ala Met His Phe Leu Glu Glu Lys Ser Leu Ile
                125                     130                     135

His Gly Asn Val Cys Ala Lys Asn Ile Leu Leu Ile Arg Glu Glu
                140                     145                     150

Asp Arg Arg Thr Gly Asn Pro Pro Phe Ile Lys Leu Ser Asp Pro
                155                     160                     165

Gly Ile Ser Ile Thr Val Leu Pro Lys Asp Ile Ser Ser Cys Cys
                170                     175                     180

Phe Gln Val Leu Gln Glu Arg Ile Pro Trp Val Pro Pro Glu Cys
                185                     190                     195

Ile Glu Asn Pro Lys Asn Leu Thr Leu Ala Thr Asp Lys Trp Ser

|                |       |       |       | 200   |       |       |       |       | 205   |       |       |       |       | 210   |
|---|---|---|---|---|---|---|---|---|---|---|---|---|---|---|
| Phe | Gly | Thr | Thr | Leu | Trp | Glu | Ile | Cys | Ser | Gly | Gly | Asp | Lys | Pro |
|     |     |     |     | 215 |     |     |     |     | 220 |     |     |     |     | 225 |
| Leu | Ser | Ala | Leu | Asp | Ser | Gln | Arg | Lys | Leu | Gln | Phe | Tyr | Glu | Asp |
|     |     |     |     | 230 |     |     |     |     | 235 |     |     |     |     | 240 |
| Lys | His | Gln | Leu | Pro | Ala | Pro | Lys | Trp | Thr | Glu | Leu | Ala | Asn | Leu |
|     |     |     |     | 245 |     |     |     |     | 250 |     |     |     |     | 255 |
| Ile | Asn | Asn | Cys | Met | Asp | Tyr | Glu | Pro | Asp | Phe | Arg | Pro | Ala | Phe |
|     |     |     |     | 260 |     |     |     |     | 265 |     |     |     |     | 270 |
| Arg | Ala | Val | Ile | Arg | Asp | Leu | Asn | Ser | Leu | Phe | Thr | Pro | Asp | Tyr |
|     |     |     |     | 275 |     |     |     |     | 280 |     |     |     |     | 285 |
| Glu | Leu | Leu | Thr | Glu | Asn | Asp | Met | Leu | Pro | Asn | Met | Arg | Ile | Gly |
|     |     |     |     | 290 |     |     |     |     | 295 |     |     |     |     | 300 |
| Ala | Leu | Gly | Phe | Ser | Gly | Ala | Phe | Glu | Asp | Arg | Asp | Pro | Thr | Gln |
|     |     |     |     | 305 |     |     |     |     | 310 |     |     |     |     | 315 |
| Phe | Glu | Glu | Arg | His | Leu | Lys | Phe | Leu | Gln | Gln | Leu | Gly | Lys | Gly |
|     |     |     |     | 320 |     |     |     |     | 325 |     |     |     |     | 330 |
| Asn | Phe | Gly | Ser | Val | Glu | Met | Cys | Arg | Tyr | Asp | Pro | Leu | Gln | Asp |
|     |     |     |     | 335 |     |     |     |     | 340 |     |     |     |     | 345 |
| Asn | Thr | Gly | Glu | Val | Val | Ala | Val | Lys | Lys | Leu | Gln | His | Ser | Thr |
|     |     |     |     | 350 |     |     |     |     | 355 |     |     |     |     | 360 |
| Glu | Glu | His | Leu | Arg | Asp | Phe | Glu | Arg | Glu | Ile | Glu | Ile | Leu | Lys |
|     |     |     |     | 365 |     |     |     |     | 370 |     |     |     |     | 375 |
| Ser | Leu | Gln | His | Asp | Asn | Ile | Val | Lys | Tyr | Lys | Gly | Val | Cys | Tyr |
|     |     |     |     | 380 |     |     |     |     | 385 |     |     |     |     | 390 |
| Ser | Ala | Gly | Arg | Arg | Asn | Leu | Arg | Leu | Ile | Met | Glu | Tyr | Leu | Pro |
|     |     |     |     | 395 |     |     |     |     | 400 |     |     |     |     | 405 |
| Tyr | Gly | Ser | Leu | Arg | Asp | Tyr | Leu | Gln | Lys | His | Lys | Glu | Arg | Ile |
|     |     |     |     | 410 |     |     |     |     | 415 |     |     |     |     | 420 |
| Asp | His | Lys | Lys | Leu | Leu | Gln | Tyr | Thr | Ser | Gln | Ile | Cys | Lys | Gly |
|     |     |     |     | 425 |     |     |     |     | 430 |     |     |     |     | 435 |
| Met | Glu | Tyr | Leu | Gly | Thr | Lys | Arg | Tyr | Ile | His | Arg | Asp | Leu | Ala |
|     |     |     |     | 440 |     |     |     |     | 445 |     |     |     |     | 450 |
| Thr | Arg | Asn | Ile | Leu | Val | Glu | Asn | Glu | Asn | Arg | Val | Lys | Ile | Gly |
|     |     |     |     | 455 |     |     |     |     | 460 |     |     |     |     | 465 |
| Asp | Phe | Gly | Leu | Thr | Lys | Val | Leu | Pro | Gln | Asp | Lys | Glu | Tyr | Tyr |
|     |     |     |     | 470 |     |     |     |     | 475 |     |     |     |     | 480 |
| Lys | Val | Lys | Glu | Pro | Gly | Glu | Ser | Pro | Ile | Phe | Trp | Tyr | Ala | Pro |
|     |     |     |     | 485 |     |     |     |     | 490 |     |     |     |     | 495 |
| Glu | Ser | Leu | Thr | Glu | Ser | Lys | Phe | Ser | Val | Ala | Ser | Asp | Val | Trp |
|     |     |     |     | 500 |     |     |     |     | 505 |     |     |     |     | 510 |
| Ser | Phe | Gly | Val | Val | Leu | Tyr | Glu | Leu | Phe | Thr | Tyr | Ile | Glu | Lys |
|     |     |     |     | 515 |     |     |     |     | 520 |     |     |     |     | 525 |
| Ser | Lys | Ser | Pro | Pro | Val | Glu | Phe | Met | Arg | Met | Ile | Gly | Asn | Asp |
|     |     |     |     | 530 |     |     |     |     | 535 |     |     |     |     | 540 |
| Lys | Gln | Gly | Gln | Met | Ile | Val | Phe | His | Leu | Ile | Glu | Leu | Leu | Lys |
|     |     |     |     | 545 |     |     |     |     | 550 |     |     |     |     | 555 |
| Ser | Asn | Gly | Arg | Leu | Pro | Arg | Pro | Glu | Gly | Cys | Pro | Asp | Glu | Ile |
|     |     |     |     | 560 |     |     |     |     | 565 |     |     |     |     | 570 |
| Tyr | Val | Ile | Met | Thr | Glu | Cys | Trp | Asn | Asn | Asn | Val | Ser | Gln | Arg |
|     |     |     |     | 575 |     |     |     |     | 580 |     |     |     |     | 585 |
| Pro | Ser | Phe | Arg | Asp | Leu | Ser | Phe | Gly | Trp | Ile | Lys | Ser | Gly | Thr |
|     |     |     |     | 590 |     |     |     |     | 595 |     |     |     |     | 600 |

Val ( 2 ) INFORMATION FOR SEQ ID NO: 17:

( i ) SEQUENCE CHARACTERISTICS:
    ( A ) LENGTH: 581 amino acids
    ( B ) TYPE: amino acid
    ( D ) TOPOLOGY: linear ( x i ) SEQUENCE DESCRIPTION: SEQ ID NO: 17:

| Ser | Phe | Asp | Arg | Ile | Leu | Lys | Lys | Asp | Leu | Val | Gln | Gly | Glu | His |
|---|---|---|---|---|---|---|---|---|---|---|---|---|---|---|
|  |  |  |  | 5 |  |  |  |  | 10 |  |  |  |  | 15 |
| Leu | Gly | Arg | Gly | Thr | Arg | Thr | His | Ile | Tyr | Ser | Gly | Thr | Leu | Met |
|  |  |  |  | 20 |  |  |  |  | 25 |  |  |  |  | 30 |
| Asp | Tyr | Lys | Asp | Asp | Glu | Gly | Thr | Ser | Glu | Glu | Lys | Lys | Ile | Lys |
|  |  |  |  | 35 |  |  |  |  | 40 |  |  |  |  | 45 |
| Val | Ile | Leu | Lys | Val | Leu | Asp | Pro | Ser | His | Arg | Asp | Ile | Ser | Leu |
|  |  |  |  | 50 |  |  |  |  | 55 |  |  |  |  | 60 |
| Ala | Phe | Phe | Glu | Ala | Ala | Ser | Met | Met | Arg | Gln | Val | Ser | His | Lys |
|  |  |  |  | 65 |  |  |  |  | 70 |  |  |  |  | 75 |
| His | Ile | Val | Tyr | Leu | Tyr | Gly | Val | Cys | Val | Arg | Asp | Val | Glu | Asn |
|  |  |  |  | 80 |  |  |  |  | 85 |  |  |  |  | 90 |
| Ile | Met | Val | Glu | Glu | Phe | Val | Glu | Gly | Gly | Pro | Leu | Asp | Leu | Phe |
|  |  |  |  | 95 |  |  |  |  | 100 |  |  |  |  | 105 |
| Met | His | Arg | Lys | Ser | Asp | Val | Leu | Thr | Thr | Pro | Trp | Lys | Phe | Lys |
|  |  |  |  | 110 |  |  |  |  | 115 |  |  |  |  | 120 |
| Val | Ala | Lys | Gln | Leu | Ala | Ser | Ala | Leu | Ser | Tyr | Leu | Glu | Asp | Lys |
|  |  |  |  | 125 |  |  |  |  | 130 |  |  |  |  | 135 |
| Asp | Leu | Val | His | Gly | Asn | Val | Cys | Thr | Lys | Asn | Leu | Leu | Leu | Ala |
|  |  |  |  | 140 |  |  |  |  | 145 |  |  |  |  | 150 |
| Arg | Glu | Gly | Ile | Asp | Ser | Glu | Cys | Gly | Pro | Phe | Ile | Lys | Leu | Ser |
|  |  |  |  | 155 |  |  |  |  | 160 |  |  |  |  | 165 |
| Asp | Pro | Gly | Ile | Pro | Ile | Thr | Val | Leu | Ser | Arg | Gln | Glu | Cys | Ile |
|  |  |  |  | 170 |  |  |  |  | 175 |  |  |  |  | 180 |
| Glu | Arg | Ile | Pro | Trp | Ile | Ala | Pro | Glu | Cys | Val | Glu | Asp | Ser | Lys |
|  |  |  |  | 185 |  |  |  |  | 190 |  |  |  |  | 195 |
| Asn | Leu | Ser | Val | Ala | Ala | Asp | Lys | Trp | Ser | Phe | Gly | Thr | Thr | Leu |
|  |  |  |  | 200 |  |  |  |  | 205 |  |  |  |  | 210 |
| Trp | Glu | Ile | Cys | Tyr | Asn | Gly | Glu | Ile | Pro | Leu | Lys | Asp | Lys | Thr |
|  |  |  |  | 215 |  |  |  |  | 220 |  |  |  |  | 225 |
| Leu | Ile | Glu | Lys | Glu | Arg | Phe | Tyr | Glu | Ser | Arg | Cys | Arg | Pro | Val |
|  |  |  |  | 230 |  |  |  |  | 235 |  |  |  |  | 240 |
| Thr | Pro | Ser | Cys | Lys | Glu | Leu | Ala | Asp | Leu | Met | Thr | Arg | Cys | Met |
|  |  |  |  | 245 |  |  |  |  | 250 |  |  |  |  | 255 |
| Asn | Tyr | Asp | Pro | Asn | Gln | Arg | Pro | Phe | Phe | Arg | Ala | Ile | Met | Arg |
|  |  |  |  | 260 |  |  |  |  | 265 |  |  |  |  | 270 |
| Asp | Ile | Asn | Lys | Leu | Glu | Glu | Gln | Asn | Pro | Asp | Ile | Val | Ser | Arg |
|  |  |  |  | 275 |  |  |  |  | 280 |  |  |  |  | 285 |
| Lys | Lys | Asn | Gln | Pro | Thr | Glu | Val | Asp | Pro | Thr | His | Phe | Thr | Lys |
|  |  |  |  | 290 |  |  |  |  | 295 |  |  |  |  | 300 |
| Arg | Phe | Leu | Lys | Arg | Ile | Arg | Asp | Leu | Gly | Glu | Gly | His | Phe | Gly |
|  |  |  |  | 305 |  |  |  |  | 310 |  |  |  |  | 315 |
| Lys | Val | Glu | Leu | Cys | Arg | Tyr | Asp | Pro | Glu | Asp | Asn | Thr | Gly | Glu |
|  |  |  |  | 320 |  |  |  |  | 325 |  |  |  |  | 330 |
| Gln | Val | Ala | Val | Lys | Ser | Leu | Lys | Pro | Glu | Ser | Gly | Gly | Asn | His |
|  |  |  |  | 335 |  |  |  |  | 340 |  |  |  |  | 345 |

| | | | | | | | | | | | | | | |
|---|---|---|---|---|---|---|---|---|---|---|---|---|---|---|
| Ile | Ala | Asp | Leu | Lys<br>350 | Lys | Glu | Ile | Glu | Ile<br>355 | Leu | Arg | Asn | Leu | Tyr<br>360 |
| His | Glu | Asn | Ile | Val<br>365 | Lys | Tyr | Lys | Gly | Ile<br>370 | Cys | Thr | Glu | Asp | Gly<br>375 |
| Gly | Asn | Gly | Ile | Lys<br>380 | Leu | Ile | Met | Glu | Phe<br>385 | Leu | Pro | Ser | Gly | Ser<br>390 |
| Leu | Lys | Glu | Tyr | Leu<br>395 | Pro | Lys | Asn | Lys | Asn<br>400 | Lys | Ile | Asn | Leu | Lys<br>405 |
| Gln | Gln | Leu | Lys | Tyr<br>410 | Ala | Val | Gln | Ile | Cys<br>415 | Lys | Gly | Met | Asp | Tyr<br>420 |
| Leu | Gly | Ser | Arg | Gln<br>425 | Tyr | Val | His | Arg | Asp<br>430 | Leu | Ala | Ala | Arg | Asn<br>435 |
| Val | Leu | Val | Glu | Ser<br>440 | Glu | His | Gln | Val | Lys<br>445 | Ile | Gly | Asp | Phe | Gly<br>450 |
| Leu | Thr | Lys | Ala | Ile<br>455 | Glu | Thr | Asp | Lys | Glu<br>460 | Tyr | Tyr | Thr | Val | Lys<br>465 |
| Asp | Asp | Arg | Asp | Ser<br>470 | Pro | Val | Phe | Trp | Tyr<br>475 | Ala | Pro | Glu | Cys | Leu<br>480 |
| Met | Gln | Ser | Lys | Phe<br>485 | Tyr | Ile | Ala | Ser | Asp<br>490 | Val | Trp | Ser | Phe | Gly<br>495 |
| Val | Thr | Leu | His | Glu<br>500 | Leu | Leu | Thr | Tyr | Cys<br>505 | Asp | Ser | Asp | Ser | Ser<br>510 |
| Pro | Met | Ala | Leu | Phe<br>515 | Leu | Lys | Met | Ile | Gly<br>520 | Pro | Thr | His | Gly | Gln<br>525 |
| Met | Thr | Val | Thr | Arg<br>530 | Leu | Val | Asn | Thr | Leu<br>535 | Lys | Glu | Gly | Lys | Arg<br>540 |
| Leu | Pro | Cys | Pro | Pro<br>545 | Asn | Cys | Pro | Asp | Glu<br>550 | Val | Tyr | Gln | Leu | Met<br>555 |
| Arg | Lys | Cys | Trp | Glu<br>560 | Phe | Gln | Pro | Ser | Asn<br>565 | Arg | Thr | Ser | Phe | Gln<br>570 |
| Asn | Leu | Ile | Glu | Gly<br>575 | Phe | Glu | Ala | Leu | Leu<br>580 | Lys | | | | |

( 2 ) INFORMATION FOR SEQ ID NO: 18:

( i ) SEQUENCE CHARACTERISTICS:
        ( A ) LENGTH: 1132 amino acids
        ( B ) TYPE: amino acid
        ( D ) TOPOLOGY: linear ( x i ) SEQUENCE DESCRIPTION: SEQ ID NO: 18:

| | | | | | | | | | | | | | | |
|---|---|---|---|---|---|---|---|---|---|---|---|---|---|---|
| Met | Gln | Tyr | Leu | Asn<br>5 | Ile | Lys | Glu | Asp | Cys<br>10 | Asn | Ala | Met | Ala | Phe<br>15 |
| Cys | Ala | Lys | Met | Arg<br>20 | Ser | Ser | Lys | Lys | Thr<br>25 | Glu | Val | Asn | Leu | Glu<br>30 |
| Ala | Pro | Glu | Pro | Gly<br>35 | Val | Glu | Val | Ile | Phe<br>40 | Tyr | Leu | Ser | Asp | Arg<br>45 |
| Glu | Pro | Leu | Arg | Leu<br>50 | Gly | Ser | Gly | Glu | Tyr<br>55 | Thr | Ala | Glu | Glu | Leu<br>60 |
| Cys | Ile | Arg | Ala | Ala<br>65 | Gln | Ala | Cys | Arg | Ile<br>70 | Ser | Pro | Leu | Cys | His<br>75 |
| Asn | Leu | Phe | Ala | Leu<br>80 | Tyr | Asp | Glu | Asn | Thr<br>85 | Lys | Leu | Trp | Tyr | Ala<br>90 |
| Pro | Asn | Arg | Thr | Ile<br>95 | Thr | Val | Asp | Asp | Lys<br>100 | Met | Ser | Leu | Arg | Leu<br>105 |

| | | | | | | | | | | | | | | |
|---|---|---|---|---|---|---|---|---|---|---|---|---|---|---|
|His|Tyr|Arg|Met|Arg<br>110|Phe|Tyr|Phe|Thr|Asn<br>115|Trp|His|Gly|Thr|Asn<br>120|
|Asp|Asn|Glu|Gln|Ser<br>125|Val|Trp|Arg|His|Ser<br>130|Pro|Lys|Lys|Gln|Lys<br>135|
|Asn|Gly|Tyr|Glu|Lys<br>140|Lys|Lys|Ile|Pro|Asp<br>145|Ala|Thr|Pro|Leu|Leu<br>150|
|Asp|Ala|Ser|Ser|Leu<br>155|Glu|Tyr|Leu|Phe|Ala<br>160|Gln|Gly|Gln|Tyr|Asp<br>165|
|Leu|Val|Lys|Cys|Leu<br>170|Ala|Pro|Ile|Arg|Asp<br>175|Pro|Lys|Thr|Glu|Gln<br>180|
|Asp|Gly|His|Asp|Ile<br>185|Glu|Asn|Glu|Cys|Leu<br>190|Gly|Met|Ala|Val|Leu<br>195|
|Ala|Ile|Ser|His|Tyr<br>200|Ala|Met|Met|Lys|Lys<br>205|Met|Gln|Leu|Pro|Glu<br>210|
|Leu|Pro|Lys|Asp|Ile<br>215|Ser|Tyr|Lys|Arg|Tyr<br>220|Ile|Pro|Glu|Thr|Leu<br>225|
|Asn|Lys|Ser|Ile|Arg<br>230|Gln|Arg|Asn|Leu|Leu<br>235|Thr|Arg|Met|Arg|Ile<br>240|
|Asn|Asn|Val|Phe|Lys<br>245|Asp|Phe|Leu|Lys|Glu<br>250|Phe|Asn|Asn|Lys|Thr<br>255|
|Ile|Cys|Asp|Ser|Ser<br>260|Val|Ser|Thr|His|Asp<br>265|Leu|Lys|Val|Lys|Tyr<br>270|
|Leu|Ala|Thr|Leu|Glu<br>275|Thr|Leu|Thr|Lys|His<br>280|Tyr|Gly|Ala|Glu|Ile<br>285|
|Phe|Glu|Thr|Ser|Met<br>290|Leu|Leu|Ile|Ser|Ser<br>295|Glu|Asn|Glu|Met|Asn<br>300|
|Trp|Phe|His|Ser|Asn<br>305|Asp|Gly|Gly|Asn|Val<br>310|Leu|Tyr|Tyr|Glu|Val<br>315|
|Met|Val|Thr|Gly|Asn<br>320|Leu|Gly|Ile|Gln|Trp<br>325|Arg|His|Lys|Pro|Asn<br>330|
|Val|Val|Ser|Val|Glu<br>335|Lys|Glu|Lys|Asn|Lys<br>340|Leu|Lys|Arg|Lys|Lys<br>345|
|Leu|Glu|Asn|Lys|Asp<br>350|Lys|Lys|Asp|Glu|Glu<br>355|Lys|Asn|Lys|Ile|Arg<br>360|
|Glu|Glu|Trp|Asn|Asn<br>365|Phe|Ser|Phe|Phe|Pro<br>370|Glu|Ile|Thr|His|Ile<br>375|
|Val|Ile|Lys|Glu|Ser<br>380|Val|Val|Ser|Ile|Asn<br>385|Lys|Gln|Asp|Asn|Lys<br>390|
|Lys|Met|Glu|Leu|Lys<br>395|Leu|Ser|Ser|His|Glu<br>400|Glu|Ala|Leu|Ser|Phe<br>405|
|Val|Ser|Leu|Val|Asp<br>410|Gly|Tyr|Phe|Arg|Leu<br>415|Thr|Ala|Asp|Ala|His<br>420|
|His|Tyr|Leu|Cys|Thr<br>425|Asp|Val|Ala|Pro|Pro<br>430|Leu|Ile|Val|His|Asn<br>435|
|Ile|Gln|Asn|Gly|Cys<br>440|His|Gly|Pro|Ile|Cys<br>445|Glu|Tyr|Ala|Ile|Asn<br>450|
|Lys|Leu|Arg|Gln|Glu<br>455|Gly|Ser|Glu|Glu|Gly<br>460|Met|Tyr|Val|Leu|Arg<br>465|
|Trp|Ser|Cys|Thr|Asp<br>470|Phe|Asp|Asn|Ile|Leu<br>475|Met|Thr|Val|Thr|Cys<br>480|
|Phe|Glu|Lys|Ser|Glu<br>485|Gln|Val|Gln|Gly|Ala<br>490|Gln|Lys|Gln|Phe|Lys<br>495|
|Asn|Phe|Gln|Ile|Glu<br>500|Val|Gln|Lys|Gly|Arg<br>505|Tyr|Ser|Leu|His|Gly<br>510|

-continued

| | | | | | | | | | | | | | | |
|---|---|---|---|---|---|---|---|---|---|---|---|---|---|---|
|Ser|Asp|Arg|Ser|Phe 515|Pro|Ser|Leu|Gly|Asp 520|Leu|Met|Ser|His|Leu 525|
|Lys|Lys|Gln|Ile|Leu 530|Arg|Thr|Asp|Asn|Ile 535|Ser|Phe|Met|Leu|Lys 540|
|Arg|Cys|Cys|Gln|Pro 545|Lys|Pro|Arg|Glu|Ile 550|Ser|Asn|Leu|Leu|Val 555|
|Ala|Thr|Lys|Lys|Ala 560|Gln|Glu|Trp|Gln|Pro 565|Val|Tyr|Pro|Met|Ser 570|
|Gln|Leu|Ser|Phe|Asp 575|Arg|Ile|Leu|Lys|Lys 580|Asp|Leu|Val|Gln|Gly 585|
|Glu|His|Leu|Gly|Arg 590|Gly|Thr|Arg|Thr|His 595|Ile|Tyr|Ser|Gly|Thr 600|
|Leu|Met|Asp|Tyr|Lys 605|Asp|Asp|Glu|Gly|Thr 610|Ser|Glu|Glu|Lys|Lys 615|
|Ile|Lys|Val|Ile|Leu 620|Lys|Val|Leu|Asp|Pro 625|Ser|His|Arg|Asp|Ile 630|
|Ser|Leu|Ala|Phe|Phe 635|Glu|Ala|Ala|Ser|Met 640|Met|Arg|Gln|Val|Ser 645|
|His|Lys|His|Ile|Val 650|Tyr|Leu|Tyr|Gly|Val 655|Cys|Val|Arg|Asp|Val 660|
|Glu|Asn|Ile|Met|Val 665|Glu|Glu|Phe|Val|Glu 670|Gly|Gly|Pro|Leu|Asp 675|
|Leu|Phe|Met|His|Arg 680|Lys|Ser|Asp|Val|Leu 685|Thr|Thr|Pro|Trp|Lys 690|
|Phe|Lys|Val|Ala|Lys 695|Gln|Leu|Ala|Ser|Ala 700|Leu|Ser|Tyr|Leu|Glu 705|
|Asp|Lys|Asp|Leu|Val 710|His|Gly|Asn|Val|Cys 715|Thr|Lys|Asn|Leu|Leu 720|
|Leu|Ala|Arg|Glu|Gly 725|Ile|Asp|Ser|Glu|Cys 730|Gly|Pro|Phe|Ile|Lys 735|
|Leu|Ser|Asp|Pro|Gly 740|Ile|Pro|Ile|Thr|Val 745|Leu|Ser|Arg|Gln|Glu 750|
|Cys|Ile|Glu|Arg|Ile 755|Pro|Trp|Ile|Ala|Pro 760|Glu|Cys|Val|Glu|Asp 765|
|Ser|Lys|Asn|Leu|Ser 770|Val|Ala|Ala|Asp|Lys 775|Trp|Ser|Phe|Gly|Thr 780|
|Thr|Leu|Trp|Glu|Ile 785|Cys|Tyr|Asn|Gly|Glu 790|Ile|Pro|Leu|Lys|Asp 795|
|Lys|Thr|Leu|Ile|Glu 800|Lys|Glu|Arg|Phe|Tyr 805|Glu|Ser|Arg|Cys|Arg 810|
|Pro|Val|Thr|Pro|Ser 815|Cys|Lys|Glu|Leu|Ala 820|Asp|Leu|Met|Thr|Arg 825|
|Cys|Met|Asn|Tyr|Asp 830|Pro|Asn|Gln|Arg|Pro 835|Phe|Phe|Arg|Ala|Ile 840|
|Met|Arg|Asp|Ile|Asn 845|Lys|Leu|Glu|Glu|Gln 850|Asn|Pro|Asp|Ile|Val 855|
|Ser|Arg|Lys|Lys|Asn 860|Gln|Pro|Thr|Glu|Val 865|Asp|Pro|Thr|His|Phe 870|
|Lys|Arg|Phe|Leu|Lys 875|Arg|Ile|Arg|Asp|Leu 880|Gly|Glu|Gly|His|Phe 885|
|Gly|Lys|Val|Glu|Leu 890|Cys|Arg|Tyr|Asp|Pro 895|Glu|Asp|Asn|Thr|Gly 900|
|Glu|Gln|Val|Ala|Val|Lys|Ser|Leu|Lys|Pro|Glu|Ser|Gly|Gly|Asn|

```
                        905                     910                     915
His  Ile  Ala  Asp  Leu  Lys  Lys  Glu  Ile  Glu  Ile  Leu  Arg  Asn  Leu
                        920                     925                     930

Tyr  His  Glu  Asn  Ile  Val  Lys  Tyr  Lys  Gly  Ile  Cys  Thr  Glu  Asp
                        935                     940                     945

Gly  Gly  Asn  Gly  Ile  Lys  Leu  Ile  Met  Glu  Phe  Leu  Pro  Ser  Gly
                        950                     955                     960

Ser  Leu  Lys  Glu  Tyr  Leu  Pro  Lys  Asn  Lys  Asn  Lys  Ile  Asn  Leu
                        965                     970                     975

Lys  Gln  Gln  Leu  Lys  Tyr  Ala  Val  Gln  Ile  Cys  Lys  Gly  Met  Asp
                        980                     985                     990

Tyr  Leu  Gly  Ser  Arg  Gln  Tyr  Val  His  Arg  Asp  Leu  Ala  Ala  Arg
                        995                     1000                    1005

Asn  Val  Leu  Val  Glu  Ser  Glu  His  Gln  Val  Lys  Ile  Gly  Asp  Phe
                        1010                    1015                    1020

Gly  Leu  Thr  Lys  Ala  Ile  Glu  Thr  Asp  Lys  Glu  Tyr  Tyr  Thr  Val
                        1025                    1030                    1035

Lys  Asp  Asp  Arg  Asp  Ser  Pro  Val  Phe  Trp  Tyr  Ala  Pro  Glu  Cys
                        1040                    1045                    1050

Leu  Met  Gln  Ser  Lys  Phe  Tyr  Ile  Ala  Ser  Asp  Val  Trp  Ser  Phe
                        1055                    1060                    1065

Gly  Val  Thr  Leu  His  Glu  Leu  Leu  Thr  Tyr  Cys  Asp  Ser  Asp  Ser
                        1070                    1075                    1080

Ser  Pro  Met  Ala  Leu  Phe  Leu  Lys  Met  Ile  Gly  Pro  Thr  His  Gly
                        1085                    1090                    1095

Gln  Met  Thr  Val  Thr  Arg  Leu  Val  Asn  Thr  Leu  Lys  Glu  Gly  Lys
                        1100                    1105                    1110

Arg  Leu  Pro  Cys  Pro  Pro  Asn  Cys  Pro  Asp  Glu  Val  Tyr  Gln  Leu
                        1115                    1120                    1125

Met  Arg  Lys  Cys  Trp  Glu  Phe
                        1130
```

( 2 ) INFORMATION FOR SEQ ID NO: 19:

( i ) SEQUENCE CHARACTERISTICS:
        ( A ) LENGTH: 971 amino acids
        ( B ) TYPE: amino acid
        ( D ) TOPOLOGY: linear ( x i ) SEQUENCE DESCRIPTION: SEQ ID NO: 19:

```
Leu  Leu  Asp  Asp  Phe  Val  Met  Ser  Tyr  Leu  Ser  Pro  Gln  Trp  Arg
                         5                      10                      15

His  Asp  Phe  Val  His  Gly  Trp  Ile  Lys  Val  Pro  Val  Thr  His  Glu
                        20                      25                      30

Thr  Gln  Glu  Glu  Cys  Leu  Gly  Met  Ala  Val  Leu  Asp  Met  Met  Arg
                        35                      40                      45

Ile  Ala  Lys  Glu  Lys  Asp  Gln  Thr  Pro  Leu  Ala  Val  Tyr  Asn  Ser
                        50                      55                      60

Val  Ser  Tyr  Lys  Thr  Phe  Leu  Pro  Lys  Cys  Val  Arg  Ala  Lys  Ile
                        65                      70                      75

Gln  Asp  Tyr  His  Ile  Leu  Thr  Arg  Lys  Arg  Ile  Arg  Tyr  Arg  Phe
                        80                      85                      90

Arg  Arg  Phe  Ile  Gln  Gln  Phe  Ser  Gln  Cys  Lys  Ala  Thr  Ala  Arg
                        95                      100                     105

Asn  Leu  Lys  Leu  Lys  Tyr  Leu  Ile  Asn  Leu  Glu  Thr  Leu  Gln  Ser
                        110                     115                     120
```

| | | | | | | | | | | | | | |
|---|---|---|---|---|---|---|---|---|---|---|---|---|---|
|Ala|Phe|Tyr|Thr|Glu<br>125|Gln|Phe|Glu|Val<br>130|Lys|Glu|Ser|Ala|Arg|Gly<br>135|
|Pro|Ser|Gly|Glu|Glu<br>140|Ile|Phe|Ala|Thr<br>145|Ile|Ile|Ile|Thr|Gly|Asn<br>150|
|Gly|Gly|Ile|Gln|Trp<br>155|Ser|Arg|Gly|Lys<br>160|His|Lys|Glu|Ser|Glu|Thr<br>165|
|Leu|Thr|Glu|Gln|Asp<br>170|Leu|Gln|Leu|Tyr<br>175|Cys|Asp|Phe|Pro|Asp|Ile<br>180|
|Ile|Asp|Val|Ser|Ile<br>185|Lys|Gln|Ala|Asn<br>190|Gln|Glu|Cys|Ser|Thr|Glu<br>195|
|Ser|Arg|Ile|Val|Thr<br>200|Val|His|Lys|Gln<br>205|Asp|Gly|Glu|Val|Leu|Glu<br>210|
|Ile|Glu|Leu|Ser|Ser<br>215|Leu|Lys|Glu|Ala<br>220|Leu|Ser|Phe|Val|Ser|Leu<br>225|
|Ile|Asp|Gly|Tyr|Tyr<br>230|Arg|Leu|Thr|Ala<br>235|Asp|Ala|His|His|Tyr|Leu<br>240|
|Cys|Lys|Glu|Val|Ala<br>245|Pro|Pro|Ala|Val<br>250|Leu|Glu|Asn|Ile|His|Ser<br>255|
|Asn|Cys|His|Gly|Pro<br>260|Ile|Ser|Met|Asp<br>265|Phe|Ala|Ile|Ser|Lys|Leu<br>270|
|Lys|Lys|Ala|Gly|Asn<br>275|Gln|Thr|Gly|Leu<br>280|Tyr|Val|Leu|Arg|Cys|Ser<br>285|
|Pro|Lys|Asp|Phe|Asn<br>290|Lys|Tyr|Phe|Leu<br>295|Thr|Phe|Ala|Val|Glu|Arg<br>300|
|Glu|Asn|Val|Ile|Glu<br>305|Tyr|Lys|His|Cys<br>310|Leu|Ile|Thr|Lys|Asn|Glu<br>315|
|Asn|Gly|Glu|Tyr|Asn<br>320|Leu|Ser|Gly|Thr<br>325|Lys|Arg|Asn|Phe|Ser|Ser<br>330|
|Leu|Lys|Asp|Leu|Leu<br>335|Asn|Cys|Tyr|Gln<br>340|Met|Glu|Thr|Val|Arg|Ser<br>345|
|Asp|Ser|Ile|Ile|Phe<br>350|Gln|Phe|Thr|Lys<br>355|Cys|Cys|Pro|Pro|Lys|Pro<br>360|
|Lys|Asp|Lys|Ser|Asn<br>365|Leu|Leu|Val|Phe<br>370|Arg|Thr|Asn|Gly|Val|Ser<br>375|
|Asp|Val|Gln|Leu|Ser<br>380|Pro|Thr|Leu|Gln<br>385|Arg|His|Asn|Asn|Val|Asn<br>390|
|Gln|Met|Val|Phe|His<br>395|Lys|Ile|Arg|Asn<br>400|Glu|Asp|Leu|Ile|Phe|Asn<br>405|
|Glu|Ser|Leu|Gly|Gln<br>410|Gly|Thr|Phe|Thr<br>415|Lys|Ile|Phe|Lys|Gly|Val<br>420|
|Arg|Arg|Glu|Val|Gly<br>425|Asp|Tyr|Gly|Gln<br>430|Leu|His|Glu|Thr|Glu|Val<br>435|
|Leu|Leu|Lys|Val|Leu<br>440|Asp|Lys|Ala|His<br>445|Arg|Asn|Tyr|Ser|Glu|Ser<br>450|
|Phe|Phe|Glu|Ala|Ala<br>455|Ser|Met|Met|Ser<br>460|Gln|Leu|Ser|His|Lys|His<br>465|
|Leu|Val|Leu|Asn|Tyr<br>470|Gly|Val|Cys|Val<br>475|Cys|Gly|Glu|Glu|Asn|Ile<br>480|
|Leu|Val|Gln|Glu|Phe<br>485|Val|Lys|Phe|Gly<br>490|Ser|Leu|Asp|Thr|Tyr|Leu<br>495|
|Lys|Lys|Asn|Lys|Asn<br>500|Ser|Ile|Asn|Ile<br>505|Leu|Trp|Lys|Leu|Gly|Val<br>510|
|Ala|Lys|Gln|Leu|Ala|Trp|Ala|Met|His|Phe|Leu|Glu|Glu|Lys|Ser|

|     |     |     |     | 515 |     |     |     |     | 520 |     |     |     |     | 525 |
|---|---|---|---|---|---|---|---|---|---|---|---|---|---|---|
| Leu | Ile | His | Gly | Asn | Val | Cys | Ala | Lys | Asn | Ile | Leu | Leu | Ile | Arg |
|     |     |     |     | 530 |     |     |     |     | 535 |     |     |     |     | 540 |
| Glu | Glu | Asp | Arg | Arg | Thr | Gly | Asn | Pro | Phe | Ile | Lys | Leu | Ser | Asp |
|     |     |     |     | 545 |     |     |     |     | 550 |     |     |     |     | 555 |
| Pro | Gly | Ile | Ser | Ile | Thr | Val | Leu | Pro | Lys | Asp | Ile | Ser | Ser | Cys |
|     |     |     |     | 560 |     |     |     |     | 565 |     |     |     |     | 570 |
| Cys | Phe | Gln | Val | Leu | Gln | Glu | Arg | Ile | Pro | Trp | Val | Pro | Pro | Glu |
|     |     |     |     | 575 |     |     |     |     | 580 |     |     |     |     | 585 |
| Cys | Ile | Glu | Asn | Pro | Lys | Asn | Leu | Thr | Leu | Ala | Thr | Asp | Lys | Trp |
|     |     |     |     | 590 |     |     |     |     | 595 |     |     |     |     | 600 |
| Ser | Phe | Gly | Thr | Thr | Leu | Trp | Glu | Ile | Cys | Ser | Gly | Gly | Asp | Lys |
|     |     |     |     | 605 |     |     |     |     | 610 |     |     |     |     | 615 |
| Pro | Leu | Ser | Ala | Leu | Asp | Ser | Gln | Arg | Lys | Leu | Gln | Phe | Tyr | Glu |
|     |     |     |     | 620 |     |     |     |     | 625 |     |     |     |     | 630 |
| Asp | Lys | His | Gln | Leu | Pro | Ala | Pro | Lys | Trp | Thr | Glu | Leu | Ala | Asn |
|     |     |     |     | 635 |     |     |     |     | 640 |     |     |     |     | 645 |
| Leu | Ile | Asn | Asn | Cys | Met | Asp | Tyr | Glu | Pro | Asp | Phe | Arg | Pro | Ala |
|     |     |     |     | 650 |     |     |     |     | 655 |     |     |     |     | 660 |
| Phe | Arg | Ala | Val | Ile | Arg | Asp | Leu | Asn | Ser | Leu | Phe | Thr | Pro | Asp |
|     |     |     |     | 665 |     |     |     |     | 670 |     |     |     |     | 675 |
| Tyr | Glu | Leu | Leu | Thr | Glu | Asn | Asp | Met | Leu | Pro | Asn | Met | Arg | Ile |
|     |     |     |     | 680 |     |     |     |     | 685 |     |     |     |     | 690 |
| Gly | Ala | Leu | Gly | Phe | Ser | Gly | Ala | Phe | Glu | Asp | Arg | Asp | Pro | Thr |
|     |     |     |     | 695 |     |     |     |     | 700 |     |     |     |     | 705 |
| Gln | Phe | Glu | Glu | Arg | His | Leu | Lys | Phe | Leu | Gln | Gln | Leu | Gly | Lys |
|     |     |     |     | 710 |     |     |     |     | 715 |     |     |     |     | 720 |
| Gly | Asn | Phe | Gly | Ser | Val | Glu | Met | Cys | Arg | Tyr | Asp | Pro | Leu | Gln |
|     |     |     |     | 725 |     |     |     |     | 730 |     |     |     |     | 735 |
| Asp | Asn | Thr | Gly | Glu | Val | Val | Ala | Val | Lys | Lys | Leu | Gln | His | Ser |
|     |     |     |     | 740 |     |     |     |     | 745 |     |     |     |     | 750 |
| Thr | Glu | Glu | His | Leu | Arg | Asp | Phe | Glu | Arg | Glu | Ile | Glu | Ile | Leu |
|     |     |     |     | 755 |     |     |     |     | 760 |     |     |     |     | 765 |
| Lys | Ser | Leu | Gln | His | Asp | Asn | Ile | Val | Lys | Tyr | Lys | Gly | Val | Cys |
|     |     |     |     | 770 |     |     |     |     | 775 |     |     |     |     | 780 |
| Tyr | Ser | Ala | Gly | Arg | Arg | Asn | Leu | Arg | Leu | Ile | Met | Glu | Tyr | Leu |
|     |     |     |     | 785 |     |     |     |     | 790 |     |     |     |     | 795 |
| Pro | Tyr | Gly | Ser | Leu | Arg | Asp | Tyr | Leu | Gln | Lys | His | Lys | Glu | Arg |
|     |     |     |     | 800 |     |     |     |     | 805 |     |     |     |     | 810 |
| Ile | Asp | His | Lys | Lys | Leu | Leu | Gln | Tyr | Thr | Ser | Gln | Ile | Cys | Lys |
|     |     |     |     | 815 |     |     |     |     | 820 |     |     |     |     | 825 |
| Gly | Met | Glu | Tyr | Leu | Gly | Thr | Lys | Arg | Tyr | Ile | His | Arg | Asp | Leu |
|     |     |     |     | 830 |     |     |     |     | 835 |     |     |     |     | 840 |
| Ala | Thr | Arg | Asn | Ile | Leu | Val | Glu | Asn | Glu | Asn | Arg | Val | Lys | Ile |
|     |     |     |     | 845 |     |     |     |     | 850 |     |     |     |     | 855 |
| Gly | Asp | Phe | Gly | Leu | Thr | Lys | Val | Leu | Pro | Gln | Asp | Lys | Glu | Tyr |
|     |     |     |     | 860 |     |     |     |     | 865 |     |     |     |     | 870 |
| Tyr | Lys | Val | Lys | Glu | Pro | Gly | Glu | Ser | Pro | Ile | Phe | Trp | Tyr | Ala |
|     |     |     |     | 875 |     |     |     |     | 880 |     |     |     |     | 885 |
| Pro | Glu | Ser | Leu | Thr | Glu | Ser | Lys | Phe | Ser | Val | Ala | Ser | Asp | Val |
|     |     |     |     | 890 |     |     |     |     | 895 |     |     |     |     | 900 |
| Trp | Ser | Phe | Gly | Val | Val | Leu | Tyr | Glu | Leu | Phe | Thr | Tyr | Ile | Glu |
|     |     |     |     | 905 |     |     |     |     | 910 |     |     |     |     | 915 |

|       |       |       |       | Pro   |       |       |       | Met   |       |       |       | Asn   |
|-------|-------|-------|-------|-------|-------|-------|-------|-------|-------|-------|-------|-------|
| Lys   | Ser   | Lys   | Ser   | Pro   | Pro   | Val   | Glu   | Phe   | Arg   | Met   | Ile   | Gly   | Asn |
|       |       |       |       | 920   |       |       |       | 925   |       |       |       | 930   |
| Asp   | Lys   | Gln   | Gly   | Gln   | Met   | Ile   | Val   | Phe   | His   | Leu   | Ile   | Glu   | Leu | Leu |
|       |       |       |       | 935   |       |       |       | 940   |       |       |       | 945   |
| Lys   | Ser   | Asn   | Gly   | Arg   | Leu   | Pro   | Arg   | Pro   | Glu   | Gly   | Cys   | Pro   | Asp | Glu |
|       |       |       |       | 950   |       |       |       | 955   |       |       |       | 960   |
| Ile   | Tyr   | Val   | Ile   | Met   | Thr   | Glu   | Cys   | Trp   | Asn   | Asn   |       |       |     |
|       |       |       |       | 965   |       |       |       | 970   |       |       |       |       |

( 2 ) INFORMATION FOR SEQ ID NO:20:

( i ) SEQUENCE CHARACTERISTICS:
        ( A ) LENGTH: 1184 amino acids
        ( B ) TYPE: amino acid
        ( D ) TOPOLOGY: linear ( x i ) SEQUENCE DESCRIPTION: SEQ ID NO:20:

| Met | Pro | Leu | Arg | His | Trp | Gly | Met | Ala | Arg | Gly | Ser | Lys | Pro | Val |
|-----|-----|-----|-----|-----|-----|-----|-----|-----|-----|-----|-----|-----|-----|-----|
|     |     |     |     | 5   |     |     |     | 10  |     |     |     | 15  |     |     |
| Gly | Asp | Gly | Ala | Gln | Pro | Met | Ala | Ala | Met | Gly | Gly | Leu | Lys | Val |
|     |     |     |     | 20  |     |     |     | 25  |     |     |     | 30  |     |     |
| Leu | Leu | His | Trp | Ala | Gly | Pro | Gly | Gly | Glu | Pro | Trp | Val | Thr |     |
|     |     |     |     | 35  |     |     |     | 40  |     |     |     | 45  |     |     |
| Phe | Ser | Glu | Ser | Ser | Leu | Ile | Ala | Glu | Val | Cys | Ile | His | Ile |     |
|     |     |     |     | 50  |     |     |     | 55  |     |     |     | 60  |     |     |
| Ala | His | Lys | Val | Gly | Ile | Thr | Pro | Pro | Cys | Phe | Asn | Leu | Phe | Ala |
|     |     |     |     | 65  |     |     |     | 70  |     |     |     | 75  |     |     |
| Leu | Phe | Asp | Ala | Gln | Ala | Gln | Val | Trp | Leu | Pro | Pro | Asn | His | Ile |
|     |     |     |     | 80  |     |     |     | 85  |     |     |     | 90  |     |     |
| Leu | Glu | Ile | Pro | Arg | Asp | Ala | Ser | Leu | Met | Leu | Tyr | Phe | Arg | Ile |
|     |     |     |     | 95  |     |     |     | 100 |     |     |     | 105 |     |     |
| Arg | Phe | Tyr | Phe | Arg | Asn | Trp | His | Gly | Met | Asn | Pro | Arg | Glu | Pro |
|     |     |     |     | 110 |     |     |     | 115 |     |     |     | 120 |     |     |
| Ala | Gly | Tyr | Arg | Cys | Gly | Pro | Pro | Gly | Thr | Glu | Ala | Ser | Ser | Asp |
|     |     |     |     | 125 |     |     |     | 130 |     |     |     | 135 |     |     |
| Gln | Thr | Ala | Gln | Gly | Met | Gln | Leu | Leu | Asp | Pro | Ala | Ser | Phe | Glu |
|     |     |     |     | 140 |     |     |     | 145 |     |     |     | 150 |     |     |
| Tyr | Leu | Phe | Glu | Gln | Gly | Lys | His | Glu | Phe | Glu | Asn | Asp | Val | Ala |
|     |     |     |     | 155 |     |     |     | 160 |     |     |     | 165 |     |     |
| Ser | Leu | Trp | Glu | Leu | Ser | Thr | Glu | Glu | Glu | Ile | His | His | Phe | Lys |
|     |     |     |     | 170 |     |     |     | 175 |     |     |     | 180 |     |     |
| Asn | Glu | Ser | Leu | Gly | Met | Ala | Phe | Leu | His | Leu | Cys | His | Leu | Ala |
|     |     |     |     | 185 |     |     |     | 190 |     |     |     | 195 |     |     |
| Leu | Arg | His | Gly | Ile | Pro | Leu | Glu | Glu | Val | Ala | Lys | Lys | Thr | Ser |
|     |     |     |     | 200 |     |     |     | 205 |     |     |     | 210 |     |     |
| Phe | Lys | Asp | Cys | Ile | Pro | Arg | Ser | Phe | Arg | Arg | His | Ile | Arg | Gln |
|     |     |     |     | 215 |     |     |     | 220 |     |     |     | 225 |     |     |
| His | Ser | Ala | Leu | Thr | Arg | Leu | Arg | Leu | Arg | Asn | Val | Phe | Arg | Arg |
|     |     |     |     | 230 |     |     |     | 235 |     |     |     | 240 |     |     |
| Phe | Leu | Arg | Asp | Phe | Gln | Pro | Gly | Arg | Leu | Ser | Gln | Gln | Met | Val |
|     |     |     |     | 245 |     |     |     | 250 |     |     |     | 255 |     |     |
| Met | Val | Lys | Tyr | Leu | Ala | Thr | Leu | Glu | Arg | Leu | Ala | Pro | Arg | Phe |
|     |     |     |     | 260 |     |     |     | 265 |     |     |     | 270 |     |     |
| Gly | Thr | Glu | Arg | Val | Pro | Val | Cys | His | Leu | Arg | Leu | Leu | Ala | Gln |
|     |     |     |     | 275 |     |     |     | 280 |     |     |     | 285 |     |     |
| Ala | Glu | Gly | Glu | Pro | Cys | Tyr | Ile | Arg | Asp | Ser | Gly | Val | Ala | Pro |

|   |   |   |   |   |   |   |   |   |   |   |   |   |   |   |
|---|---|---|---|---|---|---|---|---|---|---|---|---|---|---|
|   |   |   |   | 290 |   |   |   |   | 295 |   |   |   |   | 300 |
| Thr | Asp | Pro | Gly | Pro<br>305 | Glu | Ser | Ala | Ala | Gly<br>310 | Pro | Pro | Thr | His | Glu<br>315 |
| Val | Leu | Val | Thr | Gly<br>320 | Thr | Gly | Gly | Ile | Gln<br>325 | Trp | Trp | Pro | Val | Glu<br>330 |
| Glu | Glu | Val | Asn | Lys<br>335 | Glu | Glu | Gly | Ser | Ser<br>340 | Gly | Ser | Ser | Ala | Arg<br>345 |
| Asn | Pro | Gln | Ala | Ser<br>350 | Leu | Phe | Gly | Lys | Lys<br>355 | Ala | Lys | Ala | His | Lys<br>360 |
| Ala | Phe | Gly | Gln | Pro<br>365 | Ala | Asp | Arg | Pro | Arg<br>370 | Glu | Pro | Leu | Trp | Ala<br>375 |
| Tyr | Phe | Cys | Asp | Ile<br>380 | Thr | His | Val | Val | Leu<br>385 | Lys | Glu | His | Cys | Val<br>390 |
| Ser | Ile | His | Arg | Gln<br>395 | Asp | Asn | Lys | Cys | Leu<br>400 | Glu | Leu | Ser | Leu | Pro<br>405 |
| Ser | Arg | Ala | Ala | Ala<br>410 | Leu | Ser | Phe | Glu | Ser<br>415 | Leu | Val | Asp | Gly | Tyr<br>420 |
| Phe | Arg | Leu | Thr | Ala<br>425 | Asp | Ser | Ser | His | Tyr<br>430 | Leu | Cys | His | Glu | Val<br>435 |
| Ala | Pro | Pro | Arg | Leu<br>440 | Val | Met | Ser | Ile | Arg<br>445 | Asp | Gly | Ile | His | Gly<br>450 |
| Pro | Leu | Leu | Glu | Pro<br>455 | Phe | Val | Gln | Gln | Ala<br>460 | Lys | Leu | Arg | Pro | Leu<br>465 |
| Glu | Asp | Gly | Leu | Tyr<br>470 | Leu | Ile | His | Trp | Ser<br>475 | Thr | Ser | His | Pro | Tyr<br>480 |
| Arg | Leu | Ile | Leu | Thr<br>485 | Val | Ala | Gln | Arg | Ser<br>490 | Gln | Ala | Pro | Asp | Gly<br>495 |
| Met | Gln | Ser | Leu | Arg<br>500 | Leu | Arg | Lys | Phe | Pro<br>505 | Ile | Glu | Gln | Gln | Asp<br>510 |
| Gly | Ala | Phe | Val | Leu<br>515 | Glu | Gly | Trp | Gly | Arg<br>520 | Ser | Phe | Pro | Ser | Val<br>525 |
| Arg | Glu | Leu | Gly | Ala<br>530 | Ala | Leu | Gln | Gly | Cys<br>535 | Leu | Leu | Arg | Ala | Gly<br>540 |
| Asp | Asp | Cys | Phe | Ser<br>545 | Leu | Arg | Arg | Cys | Cys<br>550 | Leu | Pro | Gln | Pro | Gly<br>555 |
| Glu | Thr | Ser | Asn | Leu<br>560 | Ile | Ile | Met | Arg | Gly<br>565 | Ala | Arg | Ala | Ser | Pro<br>570 |
| Arg | Thr | Leu | Asn | Leu<br>575 | Ser | Gln | Leu | Ser | Phe<br>580 | His | Arg | Val | Asp | Gln<br>585 |
| Lys | Glu | Ile | Thr | Gln<br>590 | Leu | Ser | His | Leu | Gly<br>595 | Gln | Gly | Thr | Arg | Thr<br>600 |
| Asn | Val | Tyr | Glu | Gly<br>605 | Arg | Leu | Arg | Val | Glu<br>610 | Gly | Ser | Gly | Asp | Pro<br>615 |
| Glu | Glu | Gly | Lys | Met<br>620 | Asp | Asp | Glu | Asp | Pro<br>625 | Leu | Val | Pro | Gly | Arg<br>630 |
| Asp | Arg | Gly | Gln | Glu<br>635 | Leu | Arg | Val | Val | Leu<br>640 | Lys | Val | Leu | Asp | Pro<br>645 |
| Ser | His | His | Asp | Ile<br>650 | Ala | Leu | Ala | Phe | Tyr<br>655 | Glu | Thr | Ala | Ser | Leu<br>660 |
| Met | Ser | Gln | Val | Ser<br>665 | His | Thr | His | Leu | Ala<br>670 | Phe | Val | His | Gly | Val<br>675 |
| Cys | Val | Arg | Gly | Pro<br>680 | Glu | Asn | Ser | Met | Val<br>685 | Thr | Glu | Tyr | Val | Glu<br>690 |

| | | | | | | | | | | | | | |
|---|---|---|---|---|---|---|---|---|---|---|---|---|---|
|His|Gly|Pro|Leu|Asp 695|Val|Trp|Leu|Arg|Arg 700|Glu|Arg|Gly|His|Val 705|
|Pro|Met|Ala|Trp|Lys 710|Met|Val|Val|Ala|Gln 715|Gln|Leu|Ala|Ser|Ala 720|
|Leu|Ser|Tyr|Leu|Glu 725|Asn|Lys|Asn|Leu|Val 730|His|Gly|Asn|Val|Cys 735|
|Gly|Arg|Asn|Ile|Leu 740|Leu|Ala|Arg|Leu|Gly 745|Leu|Ala|Glu|Gly|Thr 750|
|Ser|Pro|Phe|Ile|Lys 755|Leu|Ser|Asp|Pro|Gly 760|Cys|Gly|Leu|Gly|Ala 765|
|Leu|Ser|Arg|Glu|Glu 770|Arg|Val|Glu|Arg|Ile 775|Pro|Trp|Leu|Ala|Pro 780|
|Glu|Cys|Leu|Pro|Gly 785|Gly|Ala|Asn|Ser|Leu 790|Ser|Thr|Ala|Met|Asp 795|
|Lys|Trp|Gly|Phe|Gly 800|Ala|Thr|Leu|Leu|Glu 805|Ile|Cys|Phe|Asp|Gly 810|
|Glu|Ala|Pro|Leu|Gln 815|Ser|Arg|Ser|Pro|Ser 820|Glu|Lys|Glu|His|Phe 825|
|Tyr|Gln|Arg|Gln|His 830|Arg|Leu|Pro|Glu|Pro 835|Ser|Cys|Pro|Gln|Leu 840|
|Ala|Thr|Leu|Thr|Ser 845|Gln|Cys|Leu|Thr|Tyr 850|Glu|Pro|Thr|Gln|Arg 855|
|Pro|Ser|Phe|Ala|Thr 860|Ile|Leu|Arg|Asp|Leu 865|Thr|Arg|Val|Gln|Pro 870|
|His|Asn|Leu|Ala|Asp 875|Val|Leu|Thr|Val|Asn 880|Arg|Asp|Ser|Pro|Ala 885|
|Val|Gly|Pro|Thr|Thr 890|Phe|His|Lys|Arg|Tyr 895|Leu|Lys|Lys|Ile|Arg 900|
|Asp|Leu|Gly|Glu|Gly 905|His|Phe|Gly|Lys|Val 910|Ser|Leu|Tyr|Cys|Tyr 915|
|Asp|Pro|Thr|Asn|Asp 920|Gly|Thr|Gly|Glu|Met 925|Val|Ala|Val|Lys|Ala 930|
|Leu|Lys|Ala|Asp|Cys 935|Gly|Pro|Gln|His|Arg 940|Ser|Gly|Trp|Lys|Gln 945|
|Glu|Ile|Asp|Ile|Leu 950|Arg|Thr|Leu|Tyr|His 955|Glu|His|Ile|Ile|Lys 960|
|Tyr|Lys|Gly|Cys|Cys 965|Glu|Asp|Gln|Gly|Glu 970|Lys|Ser|Leu|Val|Met 975|
|Glu|Tyr|Val|Pro|Leu 980|Gly|Ser|Leu|Arg|Asp 985|Tyr|Leu|Pro|Arg|His 990|
|Ser|Ile|Gly|Leu|Ala 995|Gln|Leu|Leu|Leu|Phe 1000|Ala|Gln|Gln|Ile|Cys 1005|
|Glu|Gly|Met|Ala|Tyr 1010|Leu|His|Ala|His|Asp 1015|Tyr|Ile|His|Arg|Asp 1020|
|Leu|Ala|Ala|Arg|Asn 1025|Val|Leu|Leu|Asp|Asn 1030|Asp|Arg|Leu|Val|Lys 1035|
|Ile|Gly|Asp|Phe|Gly 1040|Leu|Ala|Lys|Ala|Val 1045|Pro|Glu|Gly|His|Glu 1050|
|Tyr|Tyr|Arg|Val|Arg 1055|Glu|Asp|Gly|Asp|Ser 1060|Pro|Val|Phe|Trp|Tyr 1065|
|Ala|Pro|Glu|Cys|Leu 1070|Lys|Glu|Tyr|Asn|Phe 1075|Tyr|Tyr|Ala|Ser|Asp 1080|
|Val|Trp|Ser|Phe|Gly 1085|Val|Thr|Leu|Tyr|Glu 1090|Leu|Leu|Thr|His|Cys 1095|

| Asp | Ser | Ser | Gln | Ser<br>1100 | Pro | Pro | Thr | Lys | Phe<br>1105 | Leu | Glu | Leu | Ile | Gly<br>1110 |
| --- | --- | --- | --- | --- | --- | --- | --- | --- | --- | --- | --- | --- | --- | --- |
| Ile | Ala | Gln | Gly | Gln Met<br>1115 | Thr | Val | Leu | Arg | Leu<br>1120 | Thr | Glu | Leu | Leu<br>1125 | |
| Glu | Arg | Gly | Glu | Arg<br>1130 | Leu | Pro | Arg | Pro | Asp<br>1135 | Lys | Cys | Pro | Cys | Glu<br>1140 |
| Val | Tyr | His | Leu | Met<br>1145 | Lys | Asn | Cys | Trp | Glu<br>1150 | Thr | Glu | Ala | Ser | Phe<br>1155 |
| Arg | Pro | Thr | Phe | Glu<br>1160 | Asn | Ser | Ile | Pro | Ile<br>1165 | Leu | Lys | Thr | Val | His<br>1170 |
| Glu | Lys | Tyr | Gln | Gly<br>1175 | Gln | Ala | Pro | Ser | Val<br>1180 | Ser | Ser | Val | Cys | |

( 2 ) INFORMATION FOR SEQ ID NO:21:

( i ) SEQUENCE CHARACTERISTICS:
        ( A ) LENGTH: 92 amino acids
        ( B ) TYPE: amino acid
        ( D ) TOPOLOGY: linear ( x i ) SEQUENCE DESCRIPTION: SEQ ID NO:21:

| Trp | Tyr | His | Gly | Lys<br>5 | Leu | Asp | Arg | Thr | Ile<br>10 | Ala | Glu | Glu | Arg | Leu<br>15 |
| --- | --- | --- | --- | --- | --- | --- | --- | --- | --- | --- | --- | --- | --- | --- |
| Arg | Gln | Ala | Gly | Lys<br>20 | Ser | Gly | Ser | Tyr | Leu<br>25 | Ile | Arg | Glu | Ser | Asp<br>30 |
| Arg | Arg | Pro | Gly | Ser<br>35 | Phe | Val | Leu | Ser | Phe<br>40 | Leu | Ser | Gln | Thr | Asn<br>45 |
| Val | Val | Asn | His | Phe<br>50 | Arg | Ile | Ile | Ala | Met<br>55 | Cys | Gly | Asp | Tyr | Tyr<br>60 |
| Ile | Gly | Gly | Arg | Arg<br>65 | Phe | Ser | Ser | Leu | Ser<br>70 | Asp | Leu | Ile | Gly | Tyr<br>75 |
| Tyr | Ser | His | Val | Ser<br>80 | Cys | Leu | Leu | Lys | Gly<br>85 | Glu | Lys | Leu | Leu | Tyr<br>90 |
| Pro | Val | | | | | | | | | | | | | |

( 2 ) INFORMATION FOR SEQ ID NO:22:

( i ) SEQUENCE CHARACTERISTICS:
        ( A ) LENGTH: 91 amino acids
        ( B ) TYPE: amino acid
        ( D ) TOPOLOGY: linear ( x i ) SEQUENCE DESCRIPTION: SEQ ID NO:22:

| Trp | Phe | His | Gly | Lys<br>5 | Ile | Ser | Lys | Gln | Glu<br>10 | Ala | Tyr | Asn | Leu | Leu<br>15 |
| --- | --- | --- | --- | --- | --- | --- | --- | --- | --- | --- | --- | --- | --- | --- |
| Met | Thr | Val | Gly | Gln<br>20 | Ala | Cys | Ser | Phe | Leu<br>25 | Val | Arg | Pro | Ser | Asp<br>30 |
| Asn | Thr | Pro | Gly | Asp<br>35 | Tyr | Ser | Leu | Tyr | Phe<br>40 | Arg | Thr | Ser | Glu | Asn<br>45 |
| Ile | Gln | Arg | Phe | Lys<br>50 | Ile | Cys | Pro | Thr | Pro<br>55 | Asn | Asn | Gln | Phe | Met<br>60 |
| Met | Gly | Gly | Arg | Tyr<br>65 | Tyr | Asn | Ser | Ile | Gly<br>70 | Asp | Ile | Ile | Asp | His<br>75 |
| Tyr | Arg | Lys | Glu | Gln<br>80 | Ile | Val | Glu | Gly | Tyr<br>85 | Tyr | Leu | Lys | Glu | Pro<br>90 |
| Val | | | | | | | | | | | | | | |

(2) INFORMATION FOR SEQ ID NO: 23:

(i) SEQUENCE CHARACTERISTICS:
        (A) LENGTH: 89 amino acids
        (B) TYPE: amino acid
        (D) TOPOLOGY: linear (xi) SEQUENCE DESCRIPTION: SEQ ID NO: 23:

```
Trp Tyr Trp Gly Arg Leu Ser Arg Gly Asp Ala Val Ser Leu Leu
                  5                  10                  15

Gln Gly Gln Arg His Gly Thr Phe Leu Val Arg Asp Ser Gly Ser
                 20                  25                  30

Ile Pro Gly Asp Phe Val Leu Ser Val Ser Glu Ser Ser Arg Val
                 35                  40                  45

Ser His Tyr Ile Val Asn Ser Leu Gly Pro Ala Gly Gly Arg Arg
                 50                  55                  60

Ala Gly Gly Glu Phe Asp Ser Leu Pro Ser Leu Leu Glu Phe Tyr
                 65                  70                  75

Lys Ile His Tyr Leu Asp Thr Thr Thr Leu Ile Glu Pro Val
                 80                  85
```

METHOD FOR DETERMINING TYROSINE KINASE IN A SAMPLE

This application is a Divisional of Ser. No. 08/446,038 filed May 19, 1995 U.S. Pat. No. 5,658,791, which in turn is a Divisional of Ser. No. 08/064,067 filed Jun. 30, 1993.

The present invention relates generally to a novel protein tyrosine kinase and to genetic sequences encoding same.

Protein tyrosine kinases (PTKs) are structurally well suited to a role intracellular signal transduction. Many growth factor receptors, for example, transduce the extracellular stimulus they receive through interaction with their cognate ligand via an intracellular tyrosine kinase domain. At least one of the non-receptor PTKs, namely LCK, is believed to mediate the transduction in T-cells of a signal from the interaction of a cell-surface protein (CD4) pith a cross-linked anti-CD4 antibody.

The broader family of PTKs can be sub-divided on the basis of structural parameters of individual members. For example, the sic family of PTKs now numbers 8 members (Marth et al, 1985; Nishizawa et al, 1986; Semba et al, 1986; Martinez et al, 1987; Sukegawa et al, 1987; Yamanishi et al, 1987; Hotzman et al, 1987; Dymecki et al, 1990), each with a characteristic complement of extra-catalytic domains, including an SH2, an SH3 domain and a variable ligand binding domain. It is clear that a process of gene duplication has taken place in this case, so that the evolutionarily successful thematic structure of this family can be employed in a variety of cellular contexts. Similar PTK structural sub-families exist based around the FGF receptor and the CSF-1 receptor (reviewed in Wilks, 1990).

However, one feature in common with the aforementioned PTKs is that each kinase bears a single highly related "catalytic" domain. In accordance with the present invention a protein tyrosine kinase is provided which is distinct from those previously known. In particular, the protein tyrosine kinase of the present invention is unique since it possesses more than one protein kinase catalytic domain. Furthermore, the kinase does not bear an SH2 domain. The novel protein tyrosine kinase of the present invention represents a new subfamily or class of protein tyrosine kinase.

Accordingly, one aspect of the present invention is directed to an animal protein tyrosine kinase-like molecule comprising a polypeptide having multiple protein kinase catalytic domains but no SH2 domain.

Preferably, the polypeptide has two protein kinase catalytic domains.

Preferably, the animal is a mammal and is most preferably a human or a mouse.

Hereinafter, a protein having these characteristics will be referred to as a "JAK" (from Janus Kinase: Janus, in Encyclopedia Britannica (11th Ed) Vol XV pp 155–156). The present invention is specifically exemplified using JAK1 and JAK2 from humans and mice. This is done, however, with the understanding that the present invention extends to the whole family of JAKs from all animals and to mutants, derivatives, analogues and homologues thereof. The term "protein tyrosine kinase-like molecule" (abbreviated herein to "PTK-like molecule") is used throughout the specification and claims to emphasize that the present invention encompasses all members of the JAK family and to their mutants, derivatives, analogues and homologues.

In accordance with the present invention, there is provided a PTK-like molecule. Preferably the molecule is in biological pure or in substantially pure and/or synthetic form. The purity of the preparation is characterized by a sample comprising at least 70% by eight, preferably at least 80% by weight and most preferably at least 90% by weight PTK-like molecule. Alternatively, where the purity of the enzyme preparation is not critical, the present invention also encompasses an impure PTK-like molecule preparation but which possesses a substantial amount of JAK activity.

The present invention is directed to a naturally occurring PTK-like molecule, biologically pure or substantially pure as hereinbefore defined and to derivatives, functional analogues and homologues thereof. Such derivatives include polypeptides having single or multiple amino acid substitutions, deletions and/or additions relative to the naturally occurring sequence. These derivatives, functional analogues and homologues also encompass single or multiple substitutions, deletions and/or additions to any associated molecules such as carbohydrate, lipid and/or proteinacious moieties. Reference herein to "PTK-like molecules" includes all such derivatives, functional analogues and homologues. The present invention also extends to synthetic forms of the polypeptides which include recombinant molecules and molecules prepared by the stepwise addition of amino acids to groups of amino acids in defined order.

A range of derivatives and analogues of the PTK-like molecule are contemplated herein and include altering the molecule at its nucleotide sequence-encoding level, during its expression within a cell or in vitro or post-synthesis modification Such derivatives and analogues include, but are not limited to, modifications to side chains, incorporation of unnatural amino acids during polypeptide synthesis and the use of crosslinkers and other methods which impose conformational constraints on the polypeptide or their analogues.

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2, 4, 6, trinitrobenzene sulphonic acid (TNBS); acylation of amino groups with succinic anhydride and tetrahydrophthalic anhydride; and pyridoxylation of lysine with pyridoxal-5'-phosphate followed by reduction with $NaBH_4$.

The guanidino group of arginine residues may be modified by the formation of heterocyclic condensation products with reagents such as 2,3-butanedione, phenylgyoxal and glyoxal.

The carboxy group may be modified by carbodiimide activation via O-acylisourea formtion followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Trytophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ringe of a histidine residue may be accomplished by alkylation with iodoacetic acid derivatives or N-carbethoxylation with diethylpyrocarbonate.

Examples of incorporating unnatural amino acids and derivatives during polypeptide synthesis include, but are not limited to, use of norleucine, 4-amino butyric acid, 4-amino-3-hydroxy-5-phenlpentanoic acid, 6-aminohexanoic acid, t-burtylglycine, norvaline, phenylglycine, ornithine, sarcosine, 4-amino-3-hydroxy-6-methylheptanoic acid, 2-thienyl alanine and/or D-isomers of amino acids.

Crosslinkers can be used for example, to stabilize 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, polypeptides could be conformationally constrained by, for example, incorporation of $C_a$ and $N_a$-methylamino acids, introduction of double bonds between $C_a$ and $C_b$ atoms of amino acids and the formation of cyclic polypeptides or analogues by introducing covalent bonds such as forming an amide bond between the N and C termini, between two side chains or between a side chain and the N or C terminus.

The present invention, therefore, extends to peptides or polypeptides and amino acid and/or chemical analogues thereof corresponding to regions of PTK-like molecules. Preferably, the PTK-like molecules will retain JAK activity. However, molecules carrying mutations in the catalytic domains rendering these inactive may be useful in, for example, titrating out activity and generation of antibodies such molecules are encompassed by the present invention.

The molecular weights of the PTK-like molecules of the present invention range from 100,000 to 200,000 daltons and preferably from 120,000 to 150,000 daltons.

In a most preferred embodiment, the present inventions provides JAK1 and JAK2. JAK1 is an approximately 1142 amino acid molecule with a molecular weight of about 132,000 daltons and a nucleotide sequence shown in FIG. 2. JAK2 is an approximately 1,100 amino acid molecule with a molecular weight of about 130,000 daltons and with a nucleotide sequence shown in FIG. 8.

The present invention is also directed to genetic sequences including DNA, cDNA and mRNA which encode the PTK-like molecules hereindescribed. Such genetic sequences include single or multiple nucleotide substitutions, deletions and/or additions relative the naturally occurring sequence and extend to sequences encoding the derivatives, functional analogues and homologues of the PTK-like molecules. The present invention also provides these genetic sequences in vector and expression vector systems either in vitro or in a biological system (i.e. eukaryotic or prokaryotic cells) transformed with such vectors or genetic sequences. In a most preferred embodiment the present invention provides cDNA encoding JAK1 and JAK2 as set forth in FIGS. 2 and 8, respectively. A range of mutants can be obtained using standard techniques such as an oligonucleotide mutagenesis and chemical mutagenesis, and all such mutants and derivatives are encompassed by the present invention.

The present invention also provides antibodies to a PTK-like molecule. Such antibodies may be monoclonal or polyclonal.

The PTK-like molecule of the present invention have varying utility such as in the phosphorylation of proteins, incorporation of labels and in the design of analogues, antagonists and agonists of JAKs.

Accordingly, another aspect of the present invention contemplates a method for phosphorylating a protein comprising contacting said protein with a phosphorylating effective amount of a PTK-like molecule, said molecule comprising a polypeptide having multiple protein kinase catalytic domains but no SH2 domain for a time and under conditions sufficient for said first protein to be phosphorylated. Preferably, the polypeptide has the protein kinase catalytic domains and most preferably is JAK1 and/or JAK2 and/or their derivatives.

The present invention is further described by reference to the following non-limiting Figures and Examples.

Figure 1B:
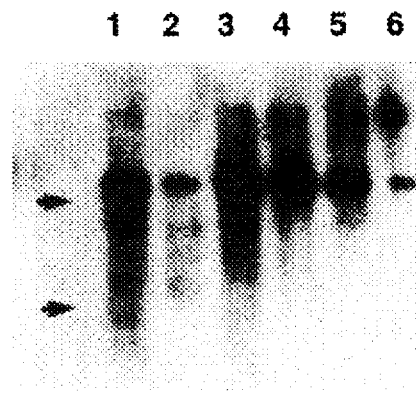

In the Figures:

FIGS. 1A and 1B are a photographic representation of a Northern analysis of murine and human JAK1.

A. 2 μg aliquots of poly(A)+ mRNA from murine tissues: lane 1, lung: lane 2, liver: lane 3, kidney: lane 4, intestine: lane 5, brain: lane 6, skeletal muscle: lane 7, spleen: lane 8, salivary grand: lane 9, placenta: lane 10, mammary gland, were fractionated on a 1.0% agarose/formaldehyde (Moran et al, 1988) gel and the RNA transferred onto a Genescreen plus (Dupont) membrane. The transferred RNA was hybridized with a 1.8 kb $^{32}$P-labelled murine JAK1 probe and the filter autoradiographed for 16 hr. at −70° C. with two intensifying screens. The relative mobilities of 28S rRNA (upper arrow) and 18S rRNA (lower arrow) are shown.

B. 2 μg aliquots of poly(A)+ mRNA from the human haemopoietic cell lines: lane 1, HL60 (myelomonocytic); lane 2, U937 (monocytic): lane 3, LK63 (pre-B): lane 4, RAJI (B-cell): lane 5, CEM (T-cell): lane 6, K562 (erythroleukaemia) were fractionated on a 1.0% agarose/formaldehyde (Moran et al, 1988) gel and the RNA transferred onto a Genescreen plus (Dupont) membrane. The transferred RNA was hybridized with a full-length $^{32}$P-labelled human JAK1 probe and the filter autoradiographed for 16 hr. at −70° C. with two intensifying screens. The relative mobilities of 28S rRNA (upper arrow) and 18S rRNA (lower arrow) are shown.

FIGS. 2A–2M is a representation showing nucleotide sequence and predicted amino acid sequence of human JAK1. The DNA sequence is numbered at the end of each line of sequence from the first nucleotide of the largest clone (pHJ7.3), the amino acid sequence (in one letter code) is numbered from the putative AUG and appears above the line to which it refers. The two kinase catalytic domains are boxed with arrows, and kinase consensus motifs are enumerated according to the nomenclature of Hanks et al (1988). The suffix a (e.g. IIa) denotes the kinase related motifs present in the first kinase-related domain (designated domain-1 in FIG. 3a) also numbered according to the same nomenclature. The tyrosine residue in an analogous position to the autophosphorylation site of a number of other protein tyrosine kinases is marked with an inverted triangle. (SEQ ID NO: 1).

Figure 3B:
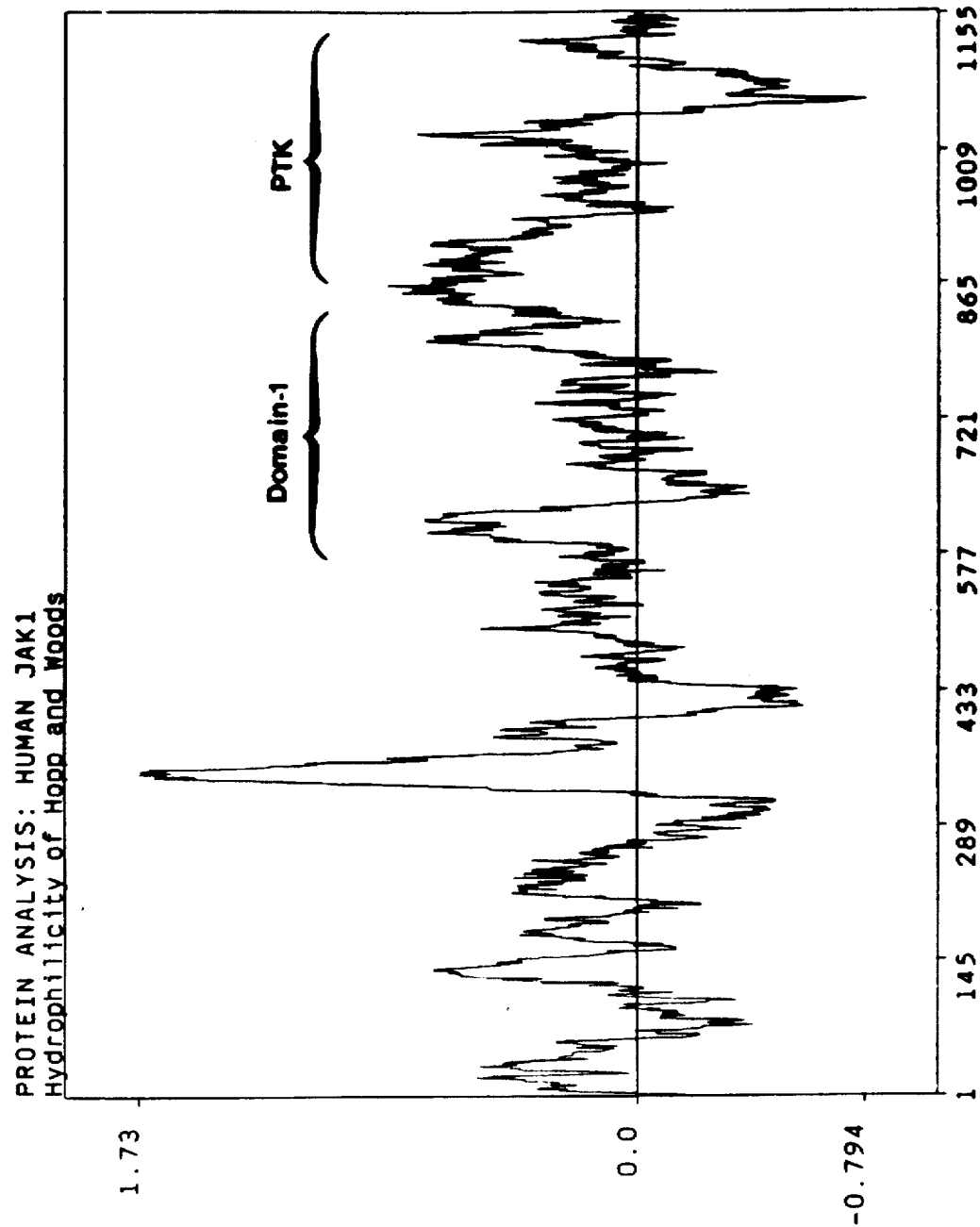

FIGS. 3A and 3B are representations showing:

Panel A. Amino-acid sequence comparison of the two kinase-related domains of JAK1. The amino-acid sequences (expressed in one letter amino acid code) of the two kinase-related domains (domain-1 amino-acids 576–825; domain-2 (PTK-domain) amino-acids 868–1130) of JAK1 and the human threonine/serine-specific kinase CDC2 (24) (amino acids 9–272) are aligned in order to maximize identity. The kinase-related domains have been divided into three segments and the number of amino acid residues separating each segment appears at the end of each line. Motifs held in common between at least two of these domains are both bolded and boxed. Roman numerals above the alignment correspond to the conserved domain nomenclature devised by Hanks et al (1988).

Panel B. Hydropathy plot of the human JAK1 protein. The protein sequence of human JAK1 (including the 10 extra amino acids which precede the most likely initiation codon) were analyzed by the hydrophilicity algorithm of Kyte and Doolittle (1982) using a span length of 25 amino acids. The relative locations of the two kinase related domains are marked as Domain-1 and PTK. The absence of a hydrophobic transmembrane domain is clearly seen, as can the presence of a highly hydrophilic region between amino acids 323 and 350.

Figure 4A:
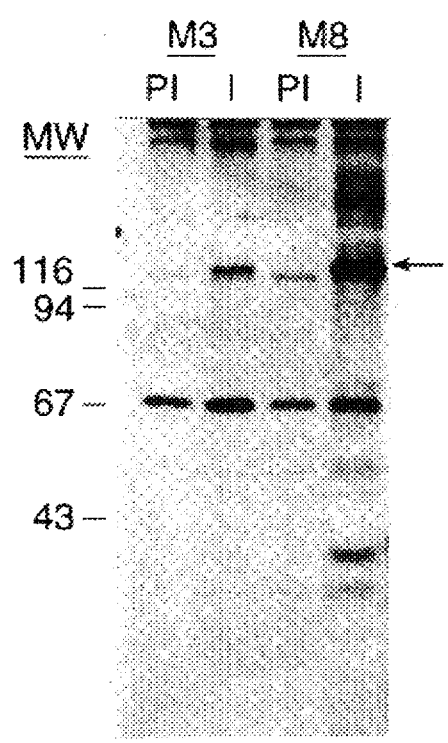

FIGS. 4A, 4B and 4C are representations of an analysis of the JAK1 protein.

Panel A. Cellular proteins of the murine mammary fibroblast cell line (17) were labelled with $^{35}$S-methionine (panel A) and immunoprecipitated with either preimmune (PI) or immune (I) anti-JAK rabbit antiserum (raised in rabbit M8 against the pGEX/JAK1/1 fusion protein or the C-terminal peptide [M3]) and fractionated on a 9.5% SDS-PAGE gel (Laemmli, 1970). Both rabbit antisera specifically immunopreciptated an $^{35}$S-labelled protein of apparent molecular weight 130,000D.

Panel B. Demonstration of tyrosine kinase activity in JAK1 bacterial fusion proteins. JAK1 fusion proteins were generated using pGEX2 (Smith and Johnson, 1988). The entire domain-1 region was included in construct pGEX/JAK1/1. The PTK domain portion of the fusion protein extended to the BamHI site 15 nucleotides 5' of the first glycine codon of the GXGXXG motif of the ATP binding site. An empty vector control was also performed. The bacteria were induced by the addition of 1mM IPTG as described by Smith and Johnson (1988) and two 1ml aliquots of the bacteria were removed at 60 minutes and 120 minutes post-induction and lysed with SDS sample buffer. Western analysis of the samples was performed using anti-phosphotyrosine antisera (PY-20[ICN]). The arrow heads mark the positions of the GEX-JAK fusion proteins, in each induction.

Panel C. Construction of the pGEX/JAK fusion proteins. The locations of the two kinase related domains of JAK1 are shown, and below, the structure of the fusion proteins with the glutathione S-transferase gene.

FIG. 5 is a representation of a sequence comparison between JAK1 and JAK2 kinase-related domains. The deduced amino acid sequence of murine JAK2 was compared to the human JAK1 amino acid sequence by application of an alignment program of the Staden VAX-based suite of Sequence analysis programs. Asterisks (*) denote identity, dollar signs ($) denote conservative substitutions. Sequences are numbered with respect to the JAK1 sequence. The extent of the domain-1 and PTK domains is shown by arrows above the amino acid sequence.

Figure 6:
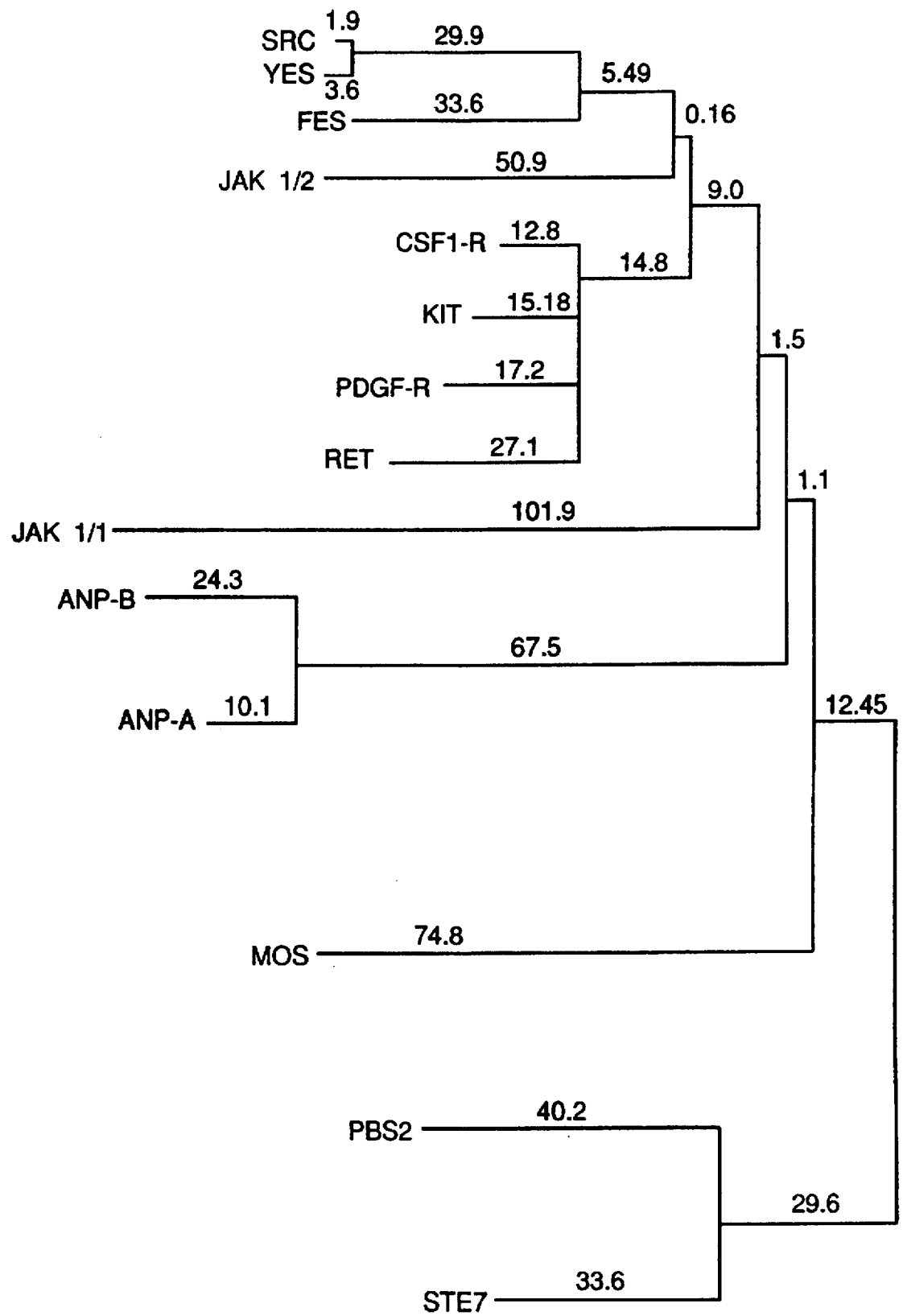

FIG. 6 is a graphical representation of a phylogenetic analysis of the two JAK1 Kinase-like domains. The tree building concept of Fitch and Margoliash (1967) as implemented by Feng and Doolittle (1987) and Hanks et al (1988) was used to generate a phylogenetic tree as described in Example 1. In each case the catalytic domain alone was used for comparison. The two kinase related domains of the JAK1 protein were compared independently. Branch order is a function of structural similarity, branch length a function of sequence identity. The abbreviations used are: SRC= c-src; YES= c-Yes; FES= c-fes; CSF1-R= Colony stimulating factor-1 receptor; KIT= c-kit; PDGF-R= Platelet derived growth factor receptor-A; RET= c-RET; ANP-A= Atrial naturetic peptide receptor-A; ANP-B= Atrial naturetic peptide receptor-B; MOS= c-mos; PBS2=polyxin B antibiotic resistance gene product; STE7= sterile mutant wild-type allele gene product; JAK1/= Domain-1 of Human JAK1; JAK1 /2= PTX domain of Human JAK1.

Figure 7B:
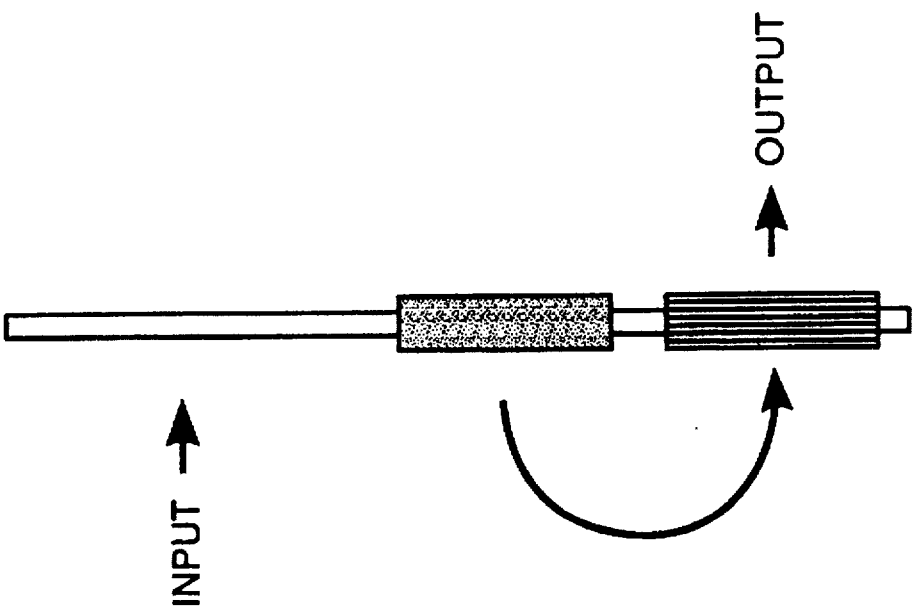
Figure 7A:
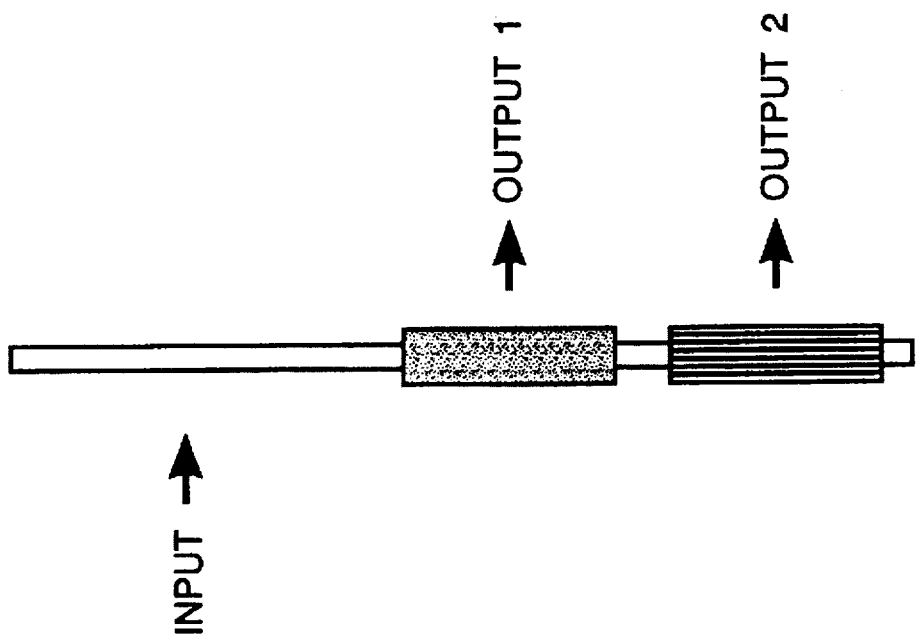

FIG. 7A and 7B are diagrammatic representations showing models for the role of members of the JAK family of PTKs in signal transduction. Two possible scenarios are considered based on an extrapolation of the current notions of the role of PTKs in signal transduction. In panel A the N-terminal domain of the JAK protein serves to sense a particular metabolic cue and convert this input into two distinct outputs. Presumably the output of the second PTK-related domain is tyrosine kinase activity; the activity of Domain-1 remains unknown. In panel B an alternative scenario is considered. In this case the function of Domain-1 is the regulation of the PTK domain. In this scenario the sole output of the JAK protein is the PTK activity.

FIG. 8A–8G are a representation of a nucleotide sequence and predicted amino acid sequence of murine JAK2. The nucleotide sequence is numbered beneath each line of sequence, from the first nucleotide of the most 5' clone. The predicted amino acid sequence, in one letter code, is numbered at the end of each line of sequence. The two putative kinase domains are shown boxed with arrows, and the kinase consensus motifs are enumerated according to the nomenclature of Hanks et al (1988). The subscript a denotes the kinase-related motifs present in the first kinase-related domain, which are numbered according to the same nomenclature. (SEQ ID NO: 2)

Figure 9:
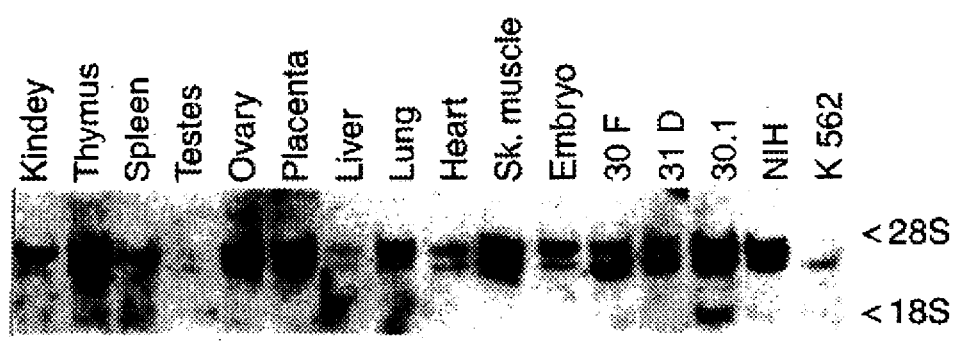

FIG. 9 is a photographic representation showing expression of JAK2 in murine tissues. Northern blot analysis of 5 μg of mRNA from each of the tissues shown on top of the figure and from various murine (30F: mammary fibroblasts; 31A: mammary epithelial cells; 30.1: factor independent subline of the hemopoietic cell line FDC.P1; NIH: fibroblasts) and human (K562: chronic myelogenous leukaemic cells) cell line. The blots were hybridized with a $^{32}$P-labelled 2.2 kb JAK2 probe and autoradiography was for 4 days. The relative mobilities of the 28S and the 18S rRNA are indicated.

Figure 10:
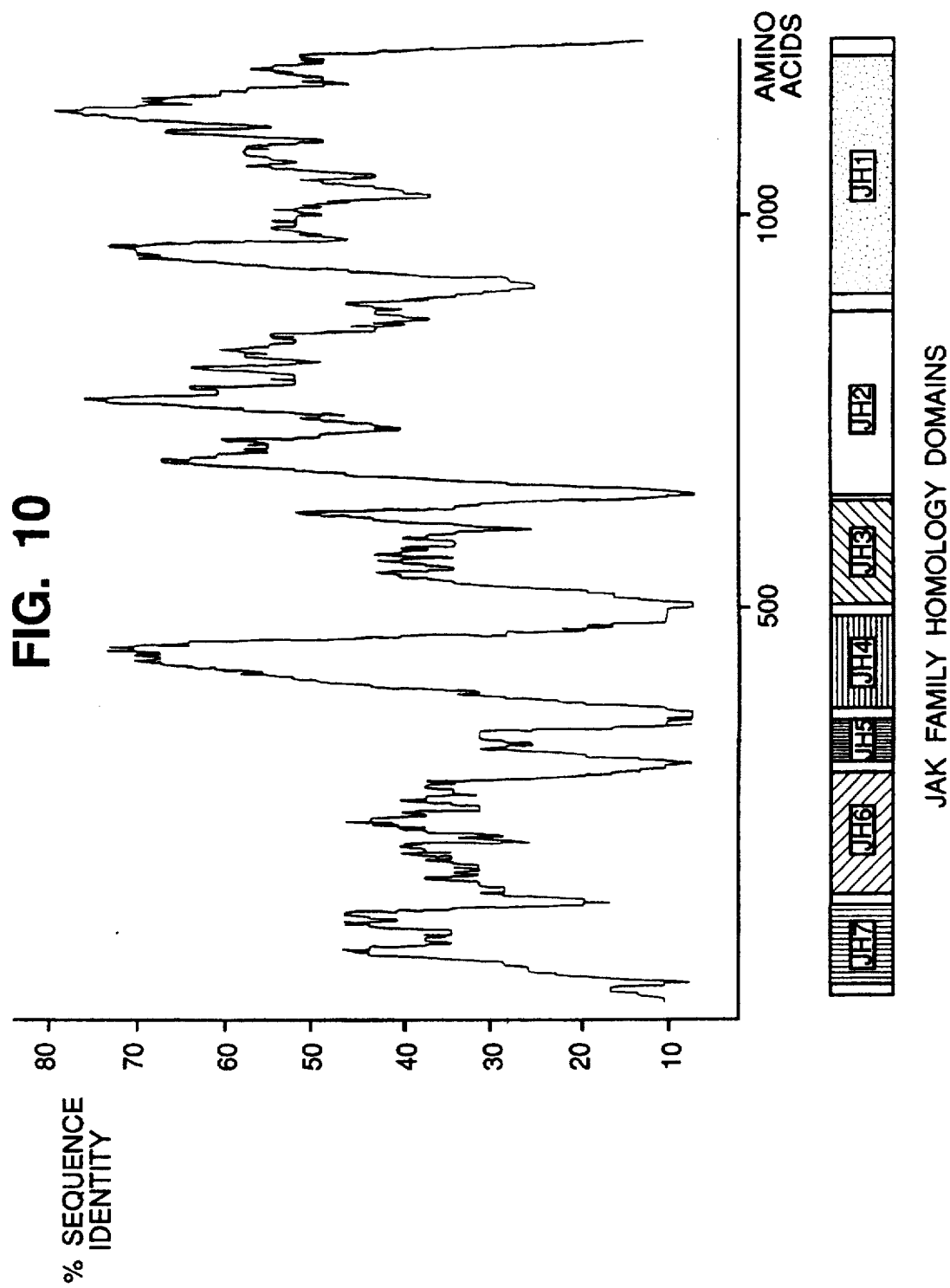

FIG. 10 is a graphical representation showing comparison of JAK1 and TYK2 amino acid sequences. The amino acid sequences of JAK1 (Wilks et al, 1991) and TYK2 (Firmbach-Kraft et al, 1990) were compared using the HOMOLOGY option in the program SEQMATCH, using a window length of 21 amino acids. The ordinate of the graph represents the percentage identity between the two sequences, the abscissa represents the amino acid position in JAK1 at which the particular level of identity was calculated. The shaded boxes below the graph represent arbitrarily ascribed JAK homology domains as discussed in the text and further demonstrated in FIG. 11.

FIG. 11A, 11B and 11C are representations showing amino acid sequence comparison of members of the JAK family of PTKs. The amino acid sequences of JAK1 (Wilks et al, 1991) (designated J1 in this figure), JAK2 (J2 in this figure), and TYK2 (Firmbach-Kraft et al, 1990) (T2 in this figure) were aligned using the CLUSTAL program (Higgins and Sharp, 1988). The numbering system is relative only to the first amino acid of JAK1, and does not take into account the insertion of gaps into this sequence, it is therefore useful only as a relative measure of location. The extent of each of the JAK homology domains was determined with reference to the homology plot shown in FIG. 10. Amino acid positions conserved in at least 2 out of the 3 sequences presented are bolded and presented below the TYK2 sequence as a consensus sequence.

Figure 12:
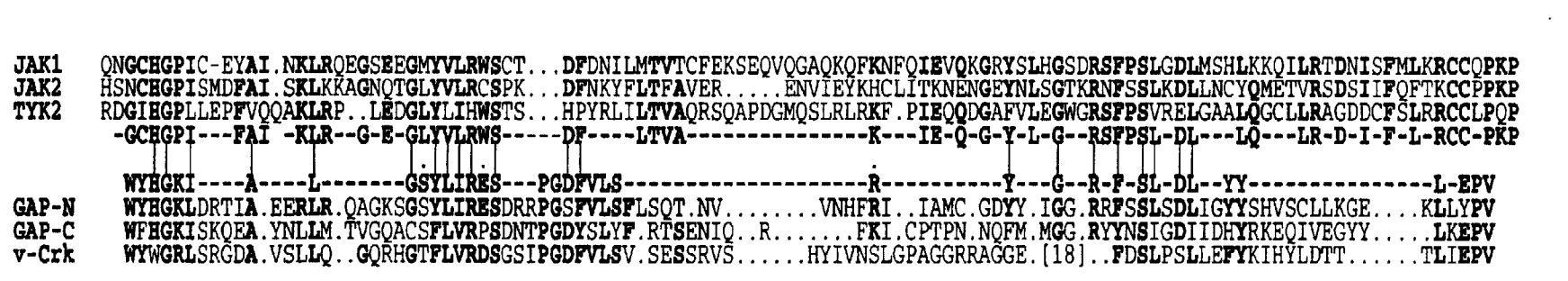

FIG. 12 is a representation showing a comparison of the JH3/JH4 domain region with SH2 domains. The two SH2 domains of GAP (the more N-terminal domain denominated GAP-N (residues 178–269), the more C-terminal, GAP-C, (residues 348–438) (Trahey et al, 1988), and the SH2 domain of v-crk (residues 248–354) (Mayer et al, 1988) were compared with the JH3/JH4 of JAK1 (residues 425–536) (Wilks et al, 1991), JAK2 (residues 252–359) (this manuscript) and TYK2 (residues 449–555) (Firmbach-Kraft et al, 1990). Amino acids held in common between the two classes of sequence are denoted by vertical lines between the two sets of sequences. Conserved residues held in common by members of the same class of domain are bolded.

EXAMPLE 1

MATERIALS AND METHODS
Screening of cDNA libraries

Several cDNA libraries were screened according to the protocols outlined in Maniatis et al, (1982). cDNA libraries from Murine NFS TPA activated spleen (Clontech cat.# ML1018), murine swiss-albino 3T3 fibroblast (Clontech cat.# 1023b), murine balb/c bone marrow (Clontech cat.# ML1007), murine swiss-webster whole brain (Clontech cat.# ML1002), murine ICR linoleic acid activated pleural macrophage (Clontech cat.# ML1020b), and human 1st-trimester foetal liver (Clontech cat.# HL1005b) were all generated in λgt 11. cDNA libraries from murine Balb/c testis (Clontech cat.# ML1020b), murine day 10 embryonic neuro-epithelium (Reid et al, 1990) and human foreskin fibroblast cell line AG1518 (Claesson-Welsh et al, 1989) were generated in λgt10. Around $10^6$ recombinants of each of these libraries were screened on each occasion.

Library screening was carried out as follows. The FD22 (JAK1) PCR clone was labelled by nick-translation (Maniatis et al, 1982) and used to screen the murine libraries. A murine cDNA clone of 1.8kb was isolated amongst 3 other positives from the neuro-epithelial and bone marrow CDNA libraries. Two full-length human JAK1 cDNA clones were isolated from the unamplified human foreskin fibroblast cell-line AG1518 by using the murine CDNA as a probe. Hybridization was at 65OC in 6×SSC; 1% SDS; 0.5% Blotto; 200 µg/ml sonicated and denatured herring sperm DNA. After hybridization, the stringency of the final wash was 0.2×SSC; 0.1% SDS at 65OC. Filters were autoradiographed overnight using Kodak XAR-5 X-ray film.

For JAK2, the murine macrophage was screened first with the FD 17 (JAK2) PCR clone, yielding 5 positives, and a portion of the longest cDNA clone isolated and used to screen the remaining cDNA libraries. Hybridization conditions were as above for JAK1.

DNA sequencing

Two strategies were employed for the sequencing of JAK1 and JAK2 cDNA clones. In the case of the human JAK1 sequence, the Erase-a-Base kit (PROMEGA) was employed to generate nested deletions of the largest EcoRI fragment. All of the murine JAK2 sequence data, and the remainder of the human JAK1 sequence, was determined using oligonucleotide primers based on previously determined DNA sequence. In each case the sequence information was generated using the dideoxynucleotide chain termination method (Sanger el al. 1977). All sequence information was determined on both strands.

Northern Analysis

Poly A + mRNA samples were prepared as elsewhere described elsewhere (Wilks and Kurban, 1988). Aliquots (1µg) were analyzed by electrophoresis on a 1% agarose gel containing 2.2M formaldehyde; 20 mM MOPS,pH 6.8; 1mM EDTA; 5 mM sodium acetate, and transferred to Hybond (Amersham, cat #RPN303N) or nitrocellulose (Schleicher & Schuell,BA85, cat #401196) membranes. Filters were prehybridized for 4hr in 50% formamide containing 3×SSC; 5×Denhardts; 10 mM HEPES pH 7.0; 100 µg.ml 1; poly C;100 µg/ml denatured herring sperm DNA; 10 µg/ml E coli DNA; 0.1% SDS, and hybridized in the same solution with nick-translated $^{32}$P-labelled murine or human JAK1 or JAK2 insert, for 18hr. at 42° C. Filters were washed to a final stringency of 0.2×SSC; 0.1% SDS at 65° C., before exposure to Kodak XAR-5 X-ray film, with two intensifying screens.

Antibody Reagents and Protein Analysis

Polyclonal rabbit antisera M7 and M8 were raised against affinity purified pGEX/JAK1/1 bacterial fusion protein (see section on kinase assays). Polyclonal antibodies M3 and M4 against the C-terminal peptide (-TSFQNLIECFEALLKC-) (SEQ ID NO: 4) of JAK1 were raised in rabbits. Peptide was coupled to Keyhole Limpet Heamocyanin with 0.05% gluteraldehyde, emulsified in Freunds' complete adjuvant and injected intradermally at several sites. The animals were boosted four and seven weeks later with coupled peptide emulsified in Freunds' incomplete adjuvant and bled ten days after the last injection.

Cells were metabolically labelled with either $^{35}$S-methionine or $^{32}$P-orthophosphate in methionine or phosphate-free medium containing 100 µCi/ml and 1mCi/ml isotope respectively. RIPA-buffer (20 mM Tris, pH7.5 containing 1% Triton X100, 1% Na deoxycholate, 0.1% SDS, 1mM EDTA, 1mM PMSF) extracts were incubated on ice with antiserum and immune-complexes isolated using Protein A bearing Staphylococus aureus bacteria. Proteins were resolved by SDS-PAGE (Lammli, 1970) and radioactively labelled bands detected by exposure to X-ray film (Kodak XAR-5). The RIPA buffer for $^{32}$P-labelled cells contained in addition 20 mM EDTA, 10 mM NaF, 100 µM orothovanadate as phosphatase inhibitors.

Phosphoamino-acid analysis of excised $^{32}$P-labelled bands was carried out exactly as described by Hunter and Sefton (1980) Western blot analysis was performed as described by Towbin et al. (1979) as modified in Ziemiecki et al (1990) using either alkaline phosphatase or $^{125}$I-labelled protein-A as a detection system.

Protein Kinase Assays

A variety of protocols have been tried in order to reveal the PTK activity of the JAK1 protein. First, extraction of murine mammary fibroblasts, Reichmann et al (1989) has been performed in a range of buffers, containing Triton-X100 or Nonidet P40 (1.0%) alone, or with added Sodium Deoxycholate (0.5% or 1.0%) or in RIPA buffer (containing 1.0% Triton-X100; 1.0% Sodium Deoxycholate; 0.1% Sodium Dodecylsulphate). Cells have been extracted in the presence or absence of phosphatase inhibitors, such as 20 mM EDTA, 10 mM NaF and 100 µM Na2VO4.

After immunoprecipitation, kinase assays have been performed in a range of ATP concentrations (100nM–10 mM) or with carrier-free γ-32P-ATP (Amersham cat #10169) in either 20 mM Tris, pH 7.4 or 50 mMM HEPES pH 7.4, with either 10 mM $Mn^{++}$, $Mg^{++}$ or $Zn^{++}$ as divalent cation. Incubations have been performed on ice (15 min), at 25° C. (15 min), at 30° C. (15 min) or at 37° C. (2 min) in the presence or absence of the phosphatase inhibitor Na2VO4.

Finally, γ-32P-GTP was employed as phosphate donor in lieu of γ-32P-ATP, with no success.

In order to generate the JAK1/glutathione transferase fusion proteins shown in FIG. 4, domain-1 (from nucleotides 1770–2672 in FIG. 2) and the PTK domain (from nucleotides 2672-end in FIG. 2, thus including 5 extra amino acids beyond the ATP binding glycine motif) were each fused into the BamHI site of pGEX2. The fusion protein was induced by the addition of lmM IPTG as described elsewhere (Smith and Johnson, 1983) and Western blot analysis performed on an induction time course with the M3 anti-JAK1 serum, and the anti-phosphotyrosine antiserum (Kamps and Sefton, 1988). Several sources of anti-phosphotyrosine antisera were tried. The data in FIG. 4b were obtained using a commercially available monoclonal antibody preparation PY-20 (ICN). In control experiments, induction of the insert-less pGEX or pGEX/JAK1 fusion protein produced no detectable tyrosine phosphorylation of bacterial substrates and the reactivity of the anti-phosphotyrosine antiserum could be completely abolished by the additional of phenyl phosphate.

Computer Aided Sequence Analysis

Amino acid sequence comparisons were performed using an alignment program from the Staden-based suite of programs on a VAX VMS 5.2. The phylogenetic analysis of the two kinase-like domains of JAK1 was performed using the tree-building concept of Fitch and Margoliash (1967) as implemented by Feng and Doolittle (1987). The SCORE program used to construct the difference matrices from which the trees were derived using the BORD and BLEN programs, were all the gift of Dr R Doolittle of the University of California, San Diego.

The sequence alignment shown in FIG. 11 was assembled using the CLUSTRAL program (Higgins and Sharp, 1988) on a VAX VMS 5.2 minocomputer. The homology plot shown in FIG. 10 was assembled using the HOMOLOGY option of the program SEQMATCH. Database searches with each of the JAK homolgoy domains was reformed using the FASTA program, based on the Pearson/Lippman algorithm (Pearson and Lippman, 1988).

RACE/Anchor PCR

RACE/Anchor PCR (Frohman et al, 1990; Loh et al, 1990) was performed by a modification of the original protocol. Briefly, 2 μg of poly(A+) mRNA is converted to cDNA using an Amersham cDNA synthesis kit (cat No. RPN 1256) and 40 ng. of a JAK2 specific oligonucleotide primer (5'-TACACCTTTAAATATTTTTGT-3') (SEQ ID NO: 5). Prior to the addition of the reverse transcriptase, the reaction mixture was heated to 65° C. cDNA synthesis was initiated by the addition of 20 units of reverse transcriptase, and the reaction incubated at 55° C. for 75 minutes. The newly sunthesised cDNA was recovered by passage through a spun sephadex column (Maniatis et al, 1982) followed by ethanol precipitation. The mRNA/cDNA heteroduplex was G-Tailed in 30 μl containing 140 mM potassium cacodylate, 30 mM Tris, (pH7.2), 1 mM CoCl$_2$, 0.1 mM DTT, 6 mM dGTP and 15 units of TdT (IBI), for 10 minutes at 37° C. The reaction was terminated by heating to 65° C. for 15 minutes and then diluted to 500 μl with 10 mM Tris. HCl (pH7.5). 1 mM EDTA. For the RACE/Anchor PCR, 10 μl of the tailed cDNA was reconstituted into 100 μl PCR buffer (50 mM KCl, 10 mM Tris. HCl[pH8.3], 1.5 mM MgCl$_2$, 0.01% gelatin, 200 μM of each dNTP) to this was added 50ng of "poly-C" oligonucleotide primer (5'-CTCGAGTCGACGAATTC$_{14}$-3') and 2.5 units of TAO polymerase (Cetus). The complementary strand of the cDNA was synthesized with one cycle of 95° C. (5 minutes), 52° C. (5 minutes) and 68° C. (40 minutes), whereupon 500 ng of the "RACE/Anchor" primer (5'-CTCGAGTCGACGAATTC-3') (SEQ ID NO: 6) and a nested JAK2 specific primer (5'-CTTGCTTAATACTGACATCA-3') (SEQ ID NO: 7 were added and the reaction mix subjected to 30 cycles of 95° C. (1 minute), 52° C. (2 minutes) and 68° C. (5 minutes). The PCR product was phenol/chloroform extracted, precipitated and resuspended in 100 μl of water. The amplified material was then kinased, size fractionated on a low-melting temperature agarose gel and cloned into Smal cleaved M13mp8. Plaques were screened by hybridization with a JAK2 cDNA and positives sequenced.

EXAMPLE 2

Isolation and DNA sequencing of cDNA clones encoding JAK1

JAK1 cDNA was cloned using PCR. Northern analysis (FIG. 1a and b) demonstrated that in both mouse and human tissues and cell lines FD22 (JAK1) was encoded by a single widely expressed 5.4kb mRNA. Human cDNA clones of FD22 (JAK1) were isolated from a human foreskin fibroblast cell line (AG 1518) cDNA library (Claesson-Welsh et al, 1989). Two of the 8 primary isolates cloned contained inserts which were candidates for being full-length cDNAs (~5.3kb).

The nucleotide sequence of human JAK1 is shown in FIG. 2. The 5' end of the clone has stop codons in all 3 reading frames prior to the putative initiation ATG. Two ATG start codons in frame with the longest open reading frame were found at positions 40 and 76 in the nucleotide sequence shown in FIG. 2. The first of these is embedded in a particularly poor "Kozak" consensus sequence (Kozak, 1984) (-TAAATGCAG-) (SEQ ID NO: 9, whereas the second matches strongly with the optimal consensus sequence defined by Kozak, namely -GCCATGGCT- (SEQ ID NO: 10. The second ATG is considered to be the initiation codon for this protein, since the first one transgresses one of the strongest correlations found in the sequences which precede initiation codons, namely the presence of a T residue (in lieu of an A residue) 3 nucleotides before the ATG sequence. At the 3'end, an in-frame stop codon at position 3502 defines the C-terminus of the protein. A large (1.405 kb) 3' untranslated region containing a polyadenylation signal completes the mRNA sequence.

The JAK1 coding region of 3426bp encodes a protein of 1142 amino-acids with a calculated molecular mass of 132,000 daltons. The PTK catalytic comain is located towards the C-terminus of the JAK1 protein (FIG. 2). In describing the structural features of this domain we have chosen to adopt the nomenclature of Hanks et al (1988). The putative ATP binding site composed of the motif GLY-X-GLY-X-X-GLY- (SEQ ID NO: 3) (subdomain 1) followed by an invariant lysine residue (subdomain II) is located between amino acid residues 871 and 896 of the JAK1 protein. The core motifs of the PTK catalytic domain (sub-domains VI to IX) are also in their appropriate locations, and are well conserved with respect to their primary sequence and their relationship to each other. The presence of a tyrosine residue at position 1022 in the JAK1 protein, 11 residues C-terminal to sub-domain VII (a similarly placed tyrosine is a site of tyrosine autophosphorylation in v-fps; Weinmaster et al, 1984) is a consistent feature of members of the PTK family and is considered diagnostic of membership of this class of kinases. The arginine residue at position 1126 (domain XI) marks the end of the highly conserved regions of the PTK catalytic domain and the entire catalytic domain of 255 amino acids is approximately 28% (with c-fes; Wilks and Kurbon, 1988) to 37% (with TRK; Kozman et al, 1988) identical to other functionally defined PTKs. Finally, there is a rare variant of the highly conserved subdomain VII motif (residues 1032–1039), which is believed to lie close to the active site (Hanks et al, 1988). The presence of phenylalanine and tyrosine flanking the conserved tryptophan in this motif is unique to JAK1 and JAK2.

A second protein kinase-related domain (designated here Domain-1) is located between amino acids 578 and 824, 47 amino acids N-terminal to the putative PTK domain. All of the conserved elements of protein kinases are preserved spatially in this domain. In FIG. 2 these elements are numbered with respect to their similarity to the subdomains of protein kinases described by Hanks et al. (1988) (with the suffix$_a$, e.g. III$_a$) and the amino acid sequences of the two kinases-related domains of JAK1 are compared to each other and to human CDC2 (Lee and Nurse, 1987) in FIG. 3a. The overall structural similarity of this domain to the kinase domains of both the PTK and threonine/serine kinase families strongly suggest that this region of the protein also functions as a protein kinase. There are, however, significant differences in the sequences of key motifs within this domain which suggest that Domain-1 may confer a catalytic activity other than serine/threonine or tyrosine phosphorylation. For example, sub-domain VI$_a$ is poorly conserved with respect to the equivalent motifs in the other kinase families, and the normally invariant -ASP-PHE-GLY- sequence of the PTK and threonine/serine kinase families (sub-domain VII$_a$) is replaced by the motif ASP-PRO-GLY- in Domain-1 of JAK1. As has been noted elsewhere, the conservation of the precise sequence of sub-domain VI in the PTK and threonine/serin kinase families appears to correlate with the substrate specificity of the kinase. Thus, it is possible that Domain-1 of the JAK1 kinase has a substrate specificity other than that exhibited by the PTK and threonine/serin kinase has a substrate specificity other than that exhibited by the PTK and threonine/serine kinases. In support of this notion there are subtle differences in the normally consistent spacing between certain key motifs in Domain-1 of JAK1. The components of the ATP binding site (sub-domains I$_a$ and II$_a$) are some 7 amino acids further apart in this domain that they are in both the PTK family and the threonine/serine kinase family. Moreover, the spacing between sub-domains VI$_a$ and VII$_a$ in this region is also longer by 9 amino acids. Conversely, the distance between sub-domains VII$_a$ and IX$_a$ is 7 amino acids shorter than the corresponding region in the PTK catalytic domain. The overall structure of this domain can be expected to be somewhat different to the catalytic domains of the members of the PTK and threonine/serine kinase families.

The sequences N-terminal to Domain-1 bear no homology to any other portion of a previously described protein kinase. Specifically, no homology was detected to the SH2 domain described for the cytoplasmic PTKs such as c-fes/fps (Sadowski et al, 1986) GAP (Trahey et al, 1988) and the phospholipase-C family of proteins (Suh et al, 1988). This is a particularly interesting observation since no other non-receptor PTK has been described which lacks this feature. A hydrophilicity plot failed to demonstrate the present of a hydrophobic domain characteristic of the growth factor receptor type of PTK (FIG. 3b) suggesting that this protein is wholly intracellular like other members of the non-receptor class of PTKs. The one outstanding feature of the JAK1 hydropathy plot is the highly hydrophilic sequence between residues 320–350. This sequence is not conserved in the murine JAK2 protein, however, its remarkable nature suggests that it may well be involved in some function of the JAK1 protein.

Expression of JAK1 protein

Several antisera were geneated against the human JAK1 protein. Polyclonal antisera directed against the hexadecamer -TSFQNLIECFEALLKC- (SEQ ID NO: 4) (the C-terminal 15 amino acids of JAK1) were raised in rabbits and used to investigate the nature of the JAK1 protein. A second rabbit antiserum was generated using a pGEX bacterial fusion protein containing the entire Domain-1 region of the human JAK1 protein (see Example 1). Preliminary sequence analysis of cDNA clones of murine JAK1 demonstrated that the C-terminus of the human and murine versions of this protein were identical whereas the murine and human Domain-1 regions exhibited a very high degree of identity. Both systems have thus been used interchangeably in the investigation of the properties of the JAX1 protein.

Both antisera have been used for Western blot analyses and immunoprecipitation studies and the data confirm the mRNA expression studies shown in FIG. 1. For example, antisera M3 and M8 both immunoprecipitate a protein of the same apparent molecular weight (130 kDaltons) from $^{35}$S-methionine labelled murine breast fibroblasts (FIG. 4a). From the same source, $^{32}$P-orthophosphate labelled JAK1 was immunoprecipitated as a phosphothreonine and phosphoserine containing phosphoprotein. It is a feature characteristic of members of the protein tyrosine kinase family that they are able to accomplish an act of self phosphorylation in vitro. Intriguingly, despite the high degree of sequence similarity held by the PTK-related sequence of JAK1 to the PTK family in general, it was not possible to demonstrate tyrosine kinase catalytic activity in immunoprecipitates of this protein from any of the murine or human sources tested. A wide range of possibilities has been tested in search of suitable conditions for the demonstration of this activity. These are listed in Example 1. The reason for the lack of activity may lie with a steric effect of the antibody in the active site of the enzyme.

In order to determine whether domain-1 or the PTK domain, in isolation, bore catalytic activity, bacterial fusion proteins of each were generated with the glutathione transferase protein of Schistosoma japonicum (Smith and Johnson, 1988) and an attempt was made to demonstrate with the aid of anti-phosphotyrosine antibodies (Kamps and Sefton, 1988) the co-ordinate induction of the fusion protein and tyrosine phosphorylated protein. In this system there is no cross-reactive background of the anti-phosphotyrosine antiserum, since there are no tyrosine kinases in bacteria (FIG. 4b). The phosphorylation of bacterial proteins on tyrosine is thus easily detectable with such a serum. In this series of experiments neither pGEX without insert nor pGEX bearing Domain-1 (pGEX/JAK/1/1) demonstrated any tyrosine kinase activity. The pGEX/JAK/1 fusion protein was further purified by affinity chromatography on a reduced glutathione column and have failed to detect any kinase activity using either histones, casein or enolase as an exogenous substrate. The pattern of inducible tyrosine phosphorylation exhibited by the pGEX PTK fusion protein (pGEX/JAK/2) (FIG. 4b) is usually simple for an ectopically expressed PTK fusion protein. Remarkably, the autophosphorylation of the fusion protein itself does not seem to occur, an observation which may go some way toward explaining why we have had difficulty in demonstrating PTK actiniry in the intact protein.

cDNA clones covering the coding region of the PCR clone FD17 (JAK2) have been isolated from a range of murine cDNA libraries. The predicted amino acid sequences of JAK2 and JAX1 show several regions of significant similarity to each other (FIG. 5, see also Example 3).

Phylogenetic analysis

The phylogenetic relationship of the catalytic domains of most of the protein kinases has been determined using the tree-building program of Feng and Doolittle (1987). FIG. 6 shows the phylogenetic relationship of the two kinase-related domains of the JAK1 protein to the rest of the kinase family. It is concluded from this family tree that these two domains had a common ancestor which pre-dated the development of the PTX sub-family. It is of interest to note that the kinase-related domains of the ANP-receptor/guanylate cyclase family diverge at a point close by.

EXAMPLE 3

Cloning and sequencing of JAK2

Sequence of Murine JAK2

The PCR clone FD17 was used as a basis to begin the cloning of longer cDNA clones of murine JAK2. cDNAs were isolated from a range of cDNA libraries, and by RACE (Frohman et al, 1989, Loh et al, 1989). The sequence of murine JAK2 is presented in FIG. 8. The predicted amino acid sequence indicates that this protein is highly related to JAK1. At the C-terminus, and extending approximately 270 amino acids towards the N-terminus (AA 715–980), are sequences bearing all the hall marks of a PTK catalytic domain. These are labelled in FIG. 8 according to the Hanks nomenclature. Immediately N-terminal to this (AA 400–660) lies the kinase-related domain characteristic of this class of PTKs (Wilks et al, 1991). The approach outlined in Example 2 in relation to JAK1 was followed and assigned these kinase related domains according to the Hanks nomenclature, appending the suffix Na to denote their origin. One unusual feature of this domain is an apparent insertion of seven amino acids between elements VIIa and VIIIa (Hanks nomenclature; Hanks and Quinn, 1991) with respect to other members of this family. This feature appeared in only one clone of the four sequenced which covered this region, and it remains possible that its presence is due to an infrequent splicing abberation, rather than being of functional significance.

Distribution of JAK2

Northern analysis of the expression of JAK2 in the mouse demonstrated two mRNA transcripts (4.8 and 4.4 kb) hybridizing to the JAK2 probe under low and high stringency hybridization conditions (FIG. 9). It is intriguing to note that the levels of these transcripts alter with respect to one another in different tissues. For example, the kidney, spleen and lung appear to express predominantly the larger form, whereas ovary, placenta, skeletal (sk) muscle and all murine cell lines analyzed express both forms at about equal levels.

Under low stringency hybridization conditions the murine JAK2 probe recognizes human JAK2 RNA (K562), however, only the smaller transcript of 4.4 kb could be detected. At this point, the origins of either of the two transcripts are unclear and no differential splicing events which could account for the differences between them could be detected. However, the major source of size differential in these transcripts may lie in the use of different polyadenylation signals. JAK2 is widely expressed in mouse organs, albeit to different levels. High expression was found in thymus, skeletal muscle, ovary and placenta, but JAK2 transcripts were barely detectable in testes or liver. In addition, JAK2 expression was detected in murine cell lines of fibroblastic (30F, NIH), epithelial (31D) and hemopoietic (30.1) origin.

JAK Family Homology Domains.

The cloning of JAK1 and JAK2 has facilitated the identification of JAK family homology domains. FIG. 10 shows a comparison of the amino acid sequences of JAK1. Sequence identity between these two proteins manifests itself as seven clearly defined homology domains. These seven domains are defined at a primary sequence level in FIG. 11. The PTK domain is classified as the JAK-homology Domain 1 (JH1), the second kinase related domain as the JH2 Domain, and so on to JH7. The boundaries of the JAK homology domains are arbitrary, and may or may not define functional domains. However, their delineation is a useful device to aid the consideration of the overall structural similarity of this class of proteins. The structure of the JH1 and JH2 Domains are described in Example 2. The JH3 is one of the least highly conserved of the JAK homology domains, each family member bearing between 35% (JAK2) to 50% (JAK1) of the deduced consensus sequence. The JH4 domain bears the sequence -GLYVLRWS- (SEQ ID NO: 11) close to its C-terminal boundary, which has some degree of homology to the SH2 domain core sequence (see below). In addition, the most highly conserved sub-domain of this region bears a potential tyrosine phosphorylation site, namely, -VDGYFRI- (SEQ ID NO: 12). Overall, the JH4 domain has between 51% (JAK2) and 64% (JAY1) of the deduced consensus sequence for this domain. Each of the remaining JAK homology domains has been independently screened against the NBRL and EMBL databases using the FASTA program. There were no compelling homologies found with anything in these databases. It is concluded that these domains are structurally and functionally conserved in members of the JAK family of PTKs, but may not, in contradistinction to the SH2 and SH3 domains of the sic family of PTKs, have a role to play in other signal transduction molecules.

The apparent absence of an SH2 domain in any of the JAK family of PTKs is intriguing. Subtle sequence similarities have been detected between SH2 consensus sequences and portions of the JH3 and JH4 domains (H. Hanafusa and A. Bernards, personal communication). FIG. 12 shows an alignment of these two domains. Whilst the similarity of the JH3 domain to SH2 domains is most evident in the region surrounding the SH2 core sequence (FLVRES), the homology does not extend far in either direction beyond this region, and only reappears again close to the C-terminal boundary of the SH2 domain. This lack of extensive homology, particularly in many of those elements most highly conserved between SH2 domains (Koch et al, 1991) (presumably indicating those residues most intimately involved in the conserved function of this domain), suggests that the homology detected is either happenstance, or the product of considerable sequence divergence in evolution. The SH2 domain is currently believed to interact with phosphorylated tyrosine residues on the substrates of PTKs (reviewed in Pawson, 1989; Koch et al, 1991). Whether the JH3/JH4 domains play a similar functional role remains to be determined.

EXAMPLE 4

To show that JAKs are represented in a range of animals, oligonucleotide probes were prepared and used to amplify and screen genomes from a variety of animals. JAK DNA was detected in Drosophila, xenopus, mouse and human genomes. The main conserved sequence was DPG common to all animals tested.

REFERENCES

Claesson-Welsh, L, Eriksson, A, Westermark, B. and Heldin, C. H., *Proc. Nat Acad. Sci. U.S.A.* 86; 4917–4921, 1989.

Feng, D. F. and Doolittle, R. F. *Jour. Mol. Evolution* 25; 351–360, 1987.
Fitch, W. M. and Margoliash, E., *Science* 12; 279–284, 1967.
Hunter, T., and Sefton, B. M. *Proc. Nat. Acd. Sci.* 77; 1311–1315, 1980.
Kamps, M. P., and Sefton, B. M. *Oncogene* 2; 305–315, 1988.
Kozak, M. *Nucleic Acids Res.* 12; 857–872, 1984.
Kozma, S. C. Redmond, S.M.S., Xiano-Chang, F., Saurer, S. M. Groner, B., and Hynes, N. E. *EMBO J.* 7; 147–154, 1988.
Kyte, J. and Doolittle, R. F. *J. Mol. Biol.* 157; 105–132, 1982.
Laemmli, U.K. *Nature* (London) 227; 680–685, 1970.
Lee, M. G. and Nurse, P. *Nature* (London) 327; 31–35, 1987.
Maniatis, T., Fritsch, E. F, and Sambrook, J., in *Molecular Cloning; A. Laboratory Manual* Cold Spring Harbor, N.Y. 1982.
Moran, M. F., Koch, C. A., Sadowski, I., and Pawson, T. *Oncogene* 3; 665–672, 1988.
Reichmann, E., Ball, R., Groner, B., and Friis, R. R. *J. Cell Biol.* 108; 1127–1138, 1989.
Smith, D. B. and Johnson, K. S. *Gene* 67; 31–40, 1988.
Suh, P., Ryu, S. H., Moon, K. H., Suh, H. W., and Rhee, S. G. *Cell* 54; 161–169, 1988.
Towbin, H., Stehelin, T., and Gordon, J., *Proc. Nat. Acad. Sci. U.S.A.* 76; 4350–4354, 1979.
Weinmaster, G., Zoller, M. M., Smith, M., Hinze, E., and Pawson, T. *Cell* 37; 559–568, 1984.
Wilks, A. F. and Kurban, R. R. *Oncogene* 3; 289–294, 1988.
Ziemiecki, A., Mueller, R. G., Xiao-Chang, F., Hynes, N. E. and Kozma, S., *EMBO J.* 9; 191–196, 1990.
Dymecki, S. M., Neiderhuber, J. E., and Desiderio, S. v. *Science* 247; 332–336, 1990.
Firmbach-Kraft, I., Byers, M., Showes, T., Dalla-Favera, R., and Krolewski, J.J., *Oncogene* 5; 1329–1336, 1990.
Frohman, M. A., Dush, M. K. and Matin, G., *Proc. Nat. Acad. Sci. U.S.A.* 85; 8998–9002, 1988.
Hanks, S. K. and Quinn, A. M. *Methods in Enzymology* 200; 38–62, 1991.
Hanks, S. K., Quinn, A. M. and Hunter, T. *Science* 241; 42–52, 1988.
Higgins, D. G. and Sharp, P. M. *Gene* 73; 237–244, 1988.
Holzman, D. A., Cook, W. D. and Dunn, A. R. *Proc. Natl. Acad. Sci. U.S.A.* 84; 8325–8329, 1987.
Koch, C. A., Anderson, D., Moran, M. F., Ellis, C., and Pawsorn, T., 252; 668–674, 1991.
Loh, E. Y., Elliot, J. f., Cwirla, S., Lanier, L. L. and Davis, M. M. *Science* 243; 217–220, 1989.
Martin J. D., Peet, R., Krebs, E. G., and Perimutter, R. M. *Cell* 43; 393–404, 1985.
Martinez, R., Mathey-Prevot, B., Bernads, A. and Baltimore, D. *Science* 237; 411–414, 1987.
Mayer, B. J., Hamaguchi, H., and Hanasfusa, H., *Nature* 332; 272–274, 1988.
Nishizawa, M., Semba, K., Yoshida, M. C. Yamamoto, T., Sasaki, M., and Toyoshima, K. *Mol. Cell. Biol.* 6; 511–517, 1986.
Pawson, T., *Oncogene* 3; 491–495, 1988.
Pearson, W. R. and Lippman, D. J. *Proc. Natl. Acad. Sci.* 85; 2444–2448, 1988.
Reid, H. H., Wilks, A. F., and Bernard, O., *Proc. Nat. Acad. Sci.* 87; 1596–1600, 1990.
Sadowski, I., Stone, J. C., and Pawson, T. *Mol. Cell. Biol.* 6; 4396–4408, 1986.
Sanger, F., Nicklen, S., and Couson, A. R., *Proc. Nat. Acad. Sci. U.S.A.* 74; 5463–5467, 1977.
Semba, K., Nishizawa, M., Myajima, N., Yoshida, M. C., Sukagawa, J., Yamanishi, Y., Sasaki, M., Yamamoto, T., and Toyoshima, K., *Proc. Natl. Acad. Sci.* 83; 5459–5463, 1986.
Sukegawa, J., Semba, K., Yamanashi, Y., Nishizawa, M., Myajima, N., Kamamoto, T., and Toyoshima, K., *Mol. Cell. Biol.* 7; 41–47, 1987.
Trahey, M., Wong, G., Halenbeck, R., Rubinfeld, B., Martin, G. A., Ladner, M., Long, C. M., Crosier, W. J., Watt, K., Koths, K., and McCormick, F., *Science* 243; 1697–1700, 1988.
Wilks, A. F., *Process in Growth Factor Research* 2; 97–111, 1990.
Wilks, A., Harpur, A., Kurban, R. R., Ralph, S. J., Zuercher, G., and Ziemiecki, A. *Molecular and Cellular Biology* 11; 2057–2065, 1991.
Yamamishi, Y., Fukushige, S. I., Semba, K., Sukegawa, J., Miyajima, N., Matsubara, K. I., Yamamoto, T., and toyoshima, K., *Molec. Cell. Biol.* 7; 237–243, 1987.

---

We claim:

1. Method for determining presence of a tyrosine kinase in a sample, comprising contacting said sample with an antibody which specifically binds to a protein encoded by SEQ ID NO: 1 or SEQ ID NO: 2, and determining said binding as a determination of said tyrosine kinase in said sample.

2. The method of claim 1, wherein said protein is encoded by SEQ ID NO: 1.

3. The method of claim 1, wherein said protein is encoded by SEQ ID NO: 2.

4. The method of claim 1, wherein said antibody binds to a peptide whose amino acid sequence consists of SEQ ID NO: 4.

5. The method of claim 1, wherein said antibody binds to a peptide whose amino acid sequence consists of SEQ ID NO: 11.

6. The method of claim 1, wherein said antibody is a monoclonal antibody.

* * * * *

UNITED STATES PATENT AND TRADEMARK OFFICE
CERTIFICATE OF CORRECTION

PATENT NO. : 5,821,069
DATED : October 13, 1998
INVENTOR(S) : Wilks, et al

It is certified that error appears in the above-identified patent and that said Letters Patent is hereby corrected as shown below:

In column 1, line 16, change "pith" to --with--.

In column 1, line 20, change "sic" to --src--.

In column 1, line 52, change "Encyclopedia" to --Encyclopaedia--.

In column 2. line 1, change "eight" to --weight--.

In column 2, line 26, after "modification" add -- . --.

In column 2, line 44, change "phenylgyoxal" to --phenylglyoxal--.

In column 2, line 46, change "carboxy" to --carboxyl--.

In column 2, line 53, after "maleimide" add -- , --.

In column 3, line 5, change "t-burtylglycine" to --butylglycine--.

UNITED STATES PATENT AND TRADEMARK OFFICE
CERTIFICATE OF CORRECTION

PATENT NO. : 5,821,069
DATED : October 13, 1998
INVENTOR(S) : Wilks, et al

It is certified that error appears in the above-identified patent and that said Letters Patent is hereby corrected as shown below:

In column 3, line 8, after "used" add -- , --.

In column 3, line 18, change "$C_b$" to --$C_\beta$--.

In column 4, line 6, change "the" to --two--.

In column 4, line 17, change "grand" to --gland--.

In column 7, line 30, change "ML1020b" to --ML1005b--.

In column 8, line 38, change "Lammli" to --Laemmli--.

In column 10, line 5, after "NO:7" add -- ) --.

In column 10, line 11, change "SmaI" to --SmaI--.

In column 10, line 35, between "9" and "," add -- ) --.

UNITED STATES PATENT AND TRADEMARK OFFICE
CERTIFICATE OF CORRECTION

PATENT NO. : 5,821,069
DATED : October 13, 1998
INVENTOR(S) : Wilks, et al

It is certified that error appears in the above-identified patent and that said Letters Patent is hereby corrected as shown below:

In column 10, line 38, between "10" and "." add -- ) --.

In column 11, line 5, change "VII" to --VIII--.

In column 11, line 38, change "serin" to --serine--.

In column 12, line 17, change "JAX1" to --JAK1--.

In column 12, line 65, change "actiniry" to --activity--.

In column 13, line 2, change "JAX1" to --JAK1--.

In column 13, line 12, change "PTX" to --PTK--.

In column 14, line 24, change "(JAY1)" to --JAK1--.

In column 14, line 32, change "sic" to --src--.

UNITED STATES PATENT AND TRADEMARK OFFICE
CERTIFICATE OF CORRECTION

PATENT NO. : 5,821,069
DATED : October 13, 1998
INVENTOR(S) : Wilks, et al

It is certified that error appears in the above-identified patent and that said Letters Patent is hereby corrected as shown below:

In column 15, line 17, after "A" delete -- . --.

In column 15, line 37, change "Matin" to --Martin--.

In column 16, line 4, change "Pawsorn" to --Pawson--.

In column 16, line 9, change "Bernads" to --Bernards--.

In column 16, line 11, change "Hanasfusa" to --Hanafusa--.

Signed and Sealed this

Seventeenth Day of August, 1999

Attest:

Q. TODD DICKINSON

*Attesting Officer*  *Acting Commissioner of Patents and Trademarks*